US011216936B2

(12) United States Patent
Sakuyama et al.

(10) Patent No.: US 11,216,936 B2
(45) Date of Patent: Jan. 4, 2022

(54) DEFECT DETECTION DEVICE, DEFECT DETECTION METHOD, AND PROGRAM

(71) Applicant: SCREEN HOLDINGS CO., LTD., Kyoto (JP)

(72) Inventors: Tsutomu Sakuyama, Kyoto (JP); Yasushi Nagata, Kyoto (JP); Hiroyuki Onishi, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 557 days.

(21) Appl. No.: 15/998,664

(22) PCT Filed: Jan. 18, 2017

(86) PCT No.: PCT/JP2017/001604
§ 371 (c)(1),
(2) Date: Aug. 16, 2018

(87) PCT Pub. No.: WO2017/141611
PCT Pub. Date: Aug. 24, 2017

(65) Prior Publication Data
US 2021/0027440 A1    Jan. 28, 2021

(30) Foreign Application Priority Data

Feb. 19, 2016  (JP) .............................. JP2016-029422
Mar. 16, 2016  (JP) .............................. JP2016-052074
Mar. 16, 2016  (JP) .............................. JP2016-052075

(51) Int. Cl.
*G06K 9/00*     (2006.01)
*G06T 7/00*     (2017.01)
(Continued)

(52) U.S. Cl.
CPC ......... *G06T 7/001* (2013.01); *G01N 21/8851* (2013.01); *G01N 33/2045* (2019.01);
(Continued)

(58) Field of Classification Search
CPC .......... G06T 2207/30148; G06T 7/001; G06T 2207/10061; G06T 7/0004; G06T 7/0008;
(Continued)

(56) References Cited

U.S. PATENT DOCUMENTS 4,803,734 A    2/1989  Onishi et al.
5,214,712 A    5/1993  Yamamoto et al.
(Continued)

FOREIGN PATENT DOCUMENTS

JP    62-140009 A    6/1987
JP    63-056761 A    3/1988
(Continued)

OTHER PUBLICATIONS

Japanese Office Action issued in corresponding Japanese Application No. 2016-052074, dated Nov. 26, 2019, with English translation.
(Continued)

*Primary Examiner* — Alex Kok S Liew
(74) *Attorney, Agent, or Firm* — McDermott Will & Emery LLP

(57) ABSTRACT

A plurality of captured images is acquired while changing a light illumination state. Each captured image is compared with a corresponding reference image to acquire a region where the captured image is darker than the reference image as a dark defect candidate region. From each of a plurality of captured images, a region where the captured image is lighter than the reference image is acquired as a lightness/darkness inverted region. Among the dark defect candidate regions, those that do not overlap by a prescribed criterion or more with any of the lightness/darkness inverted regions are excluded from defect candidates, and then the presence of a defect is acquired on the basis of the defect candidate regions. This suppresses over-detection of defects arising (Continued)

from, for example, grime on the surface during external appearance inspection.

6 Claims, 31 Drawing Sheets

(51) Int. Cl.
  *G01N 33/2045* (2019.01)
  *G01N 21/88* (2006.01)
  *G06T 3/40* (2006.01)
(52) U.S. Cl.
  CPC ........ *G06T 3/40* (2013.01); *G01N 2021/8887* (2013.01); *G06T 2207/30136* (2013.01)
(58) Field of Classification Search
  CPC ................ G06T 7/0006; G06T 7/0002; G06T 2207/10024; G06T 2207/10056; G06T 2200/24; G06T 2207/10004; G06T 2207/10152; G06T 2207/20224; G06T 2207/30141; G06T 2207/20076; G06T 2207/20081; G06T 2207/30121; G06T 2207/30168; G06T 7/13; G06T 1/0007; G06T 2207/10048; G06T 2207/30152; G06T 5/50; G06T 7/33; G01N 21/9501; G01N 21/95607; G01N 21/956; G01N 2021/95676; G01N 21/8851; G01N 21/8806; G01N 202/8887; G01N 2021/8822; G01N 2021/8848; G01N 2021/8854; G01N 2021/8861; G01N 2021/8867
  USPC ................................................. 382/141–152
  See application file for complete search history.

(56) References Cited

U.S. PATENT DOCUMENTS

| | | | |
|---|---|---|---|
| 5,848,189 | A | 12/1998 | Pearson et al. |
| 6,396,945 | B1 | 5/2002 | Ishii |
| 6,445,452 | B1 | 9/2002 | Kondou et al. |
| 2003/0076989 | A1* | 4/2003 | Maayah ................ G06T 7/0004 382/145 |
| 2013/0294677 | A1 | 11/2013 | Urano et al. |
| 2013/0336575 | A1* | 12/2013 | Dalla-Torre ............ G06T 7/001 382/149 |
| 2017/0122878 | A1 | 5/2017 | Ono et al. |

FOREIGN PATENT DOCUMENTS

| | | | |
|---|---|---|---|
| JP | 63-124945 | A | 5/1988 |
| JP | 64-041977 | | 2/1989 |
| JP | 02-156144 | A | 6/1990 |
| JP | 04-319649 | A | 11/1992 |
| JP | 08-033342 | B2 | 3/1996 |
| JP | 11-224892 | A | 8/1999 |
| JP | H11-242746 | A | 9/1999 |
| JP | 2001-041900 | A | 2/2001 |
| JP | 2002-116153 | A | 4/2002 |
| JP | 2002-140695 | A | 5/2002 |
| JP | 2002-250700 | A | 9/2002 |
| JP | 2005-037203 | A | 2/2005 |
| JP | 2007-310162 | A | 11/2007 |
| JP | 2010-223621 | A | 10/2010 |
| JP | 2012-027810 | A | 2/2012 |
| JP | 2012-112915 | A | 6/2012 |
| JP | 2013-242256 | A | 12/2013 |
| JP | 2015-137921 | A | 7/2015 |
| JP | 2015-161622 | A | 9/2015 |
| JP | 2015-210150 | A | 11/2015 |
| TW | 201604536 | A | 2/2016 |
| WO | 2014/034526 | A1 | 3/2014 |

OTHER PUBLICATIONS

Japanese Notice of Reasons for Refusal issued in corresponding Japanese Patent Application No. 2016-029422, dated Aug. 22, 2019, with English translation.
International Search Report issued in corresponding International Patent Application No. PCT/JP2017/001604, dated Apr. 4, 2017, with English Translation.
G. Heygster, "Rank Filters in Digital Image Processing", Computer Graphics and Image Processing, vol. 19, (1982), pp. 148-164.
Extended European Search Report issued in corresponding European Patent Application No. 17752875.9, dated Feb. 18, 2019.
Notification Concerning Transmittal of International Preliminary Report on Patentability dated Aug. 30, 2018 in corresponding International Application No. PCT/JP2017/001604 (7 pages).
Notification of Transmittal of Translation of the International Preliminary Report on Patentability, dated Aug. 30, 2018 in corresponding International Application No. PCT/JP2017/001604 (10 pages).
European Office Action issued in corresponding European Application No. 17 752 875.9, dated Sep. 30, 2021.
Hodgson R. et al. "Properties, implementations and applications of rank filters," Image and Vision Computing, Elsevier, Guildford, GB, vol. 3, No. 1, Feb. 1, 1985, pp. 3-14.

* cited by examiner

DEFECT DETECTION DEVICE, DEFECT DETECTION METHOD, AND PROGRAM

CROSS REFERENCE

This application is the U.S. National Phase under 35 U.S.C. § 371 of International Application No. PCT/JP2017/001604, filed on Jan. 18, 2017, which claims the benefit of Japanese Application No. 2016-029422, filed on Feb. 19, 2016, Japanese Application No 2016-052075, filed on Mar. 16, 2016 and Japanese Patent Application No. 2016-052074, filed on Mar. 16, 2016, the entire contents of each are hereby incorporated by reference.

TECHNICAL FIELD

The present invention relates to a technique for detecting a surface defect in an object.

BACKGROUND ART

Metal components used in the actuators of automobiles have conventionally been manufactured by forging or casting. After the manufacture of the metal components, a so-called external appearance inspection is conducted to check the presence or absence of defects such as scratches in the obtained metal components. Such external appearance inspections of the metal components have conventionally been conducted by visual inspections by operators. However, such dependence on visual inspections by operators causes variations in the time required for inspection and the result of inspection among a plurality of operators. Also, even one and the same operator may take longer time for inspection or overlook defects due to physical deconditioning or a lapse in concentration. Thus, there has been demand for the development of devices that can conduct external appearance inspections of metal components automatically and at high speed.

With this in view, devices that capture images of an object by irradiation with light and inspect the external appearance of the object on the basis of the captured images have conventionally been used. In particular, a technique (so-called self-comparison technique) for extracting defect candidates by performing difference processing on captured images before and after expansion and reduction processing is known.

For example, the external appearance inspection device for inspecting the external appearance of an electronic component, disclosed in Japanese Patent Application Laid-Open No. 2015-137921, performs binarization processing on a captured image, then generates a reduced image by performing expansion processing and reduction processing on the captured image to cause small-size defects to disappear, and extracts small-size defects by obtaining a difference between the reduced image and the captured image. Japanese Patent Application Laid-Open No. 2015-137921 also discloses that large-size defects are also extracted through difference processing between captured images and reference images, and if even one difference image is determined to be NG (defective), a determination result indicating that the captured image is defective is output (see paragraphs 0061 to 0074 and FIGS. 5 and 6).

The inspections by self-comparison as described above can extract various types of defects existing in captured images from only the captured images without requiring to prepare images that are used as references in inspection (hereinafter, referred to as "reference images"). However, it is necessary to suppress over-detection because thin lines and minute asperities that are not defects are also detected as defects in the surface of an object included in the captured images.

There is also known a technique for preparing an image that is used as a reference in inspection (hereinafter referred to as a "reference image") for a captured image and extracting defect candidates included in the captured image by comparison between the captured image and the reference image.

For example, Japanese Patent Application Laid-Open No. 62-140009 discloses, as a pattern defect detection technique, a so-called "shifting comparison" technique in which a plurality of master patterns is set for an object pattern zone by shifting each pixel two-dimensionally by a predetermined amount across an extended zone that centers on a master pattern zone corresponding in position to the object pattern zone and that is obtained by extending this master pattern zone by the required number of pixels, and defects are detected for each master pattern zone by comparing binarized signals of the master pattern zone and binarized signals of the object pattern.

If an image that includes a defect in an object is selected as a reference image, that defect part causes a difference between a captured image and the reference image even if an object appearing in the captured image has no defects. Thus, such reference images will become the cause of so-called over-detection, i.e., a non-defective captured image is detected as a "defective" image. In view of this, with the conventional techniques, an inspection involving the comparison between a captured image and a reference image as described above is based on the prerequisite that a non-defective image is prepared as a reference image.

Accordingly, as pre-processing for defect detection, a selection step of selecting an object with no defects, i.e., a so-called non-defective object, is required for obtaining reference images, and eventually a need arises to detect some defects by visual inspections by operators. This inhibits shortening of the operating time.

Also, such inspection devices need to prevent surface colors caused by, for example, grime from being detected as defects when detecting defects in the form of depressions or projections.

For example, the defect inspection device for sheet-like objects, disclosed in Japanese Patent Application Laid-Open No. H2-156144, irradiates a sheet-like object with light from an oblique direction and classifies depressions, projections, and grime parts according to positional relationships between dark shadow regions and light bright-point regions. The external appearance inspection device disclosed in Japanese Patent Application Laid-Open No. 2002-116153 changes the illumination of a surface to be inspected and detects flaws with accuracy by using the fact that the change in illumination causes flaws and oil to show different changes in density in images. The inspection device for rod-like objects, disclosed in Japanese Patent Application Laid-Open No. 2005-37203, irradiates a rod-like object with red light and blue light from opposite directions so as to decompose a color image into a red image and a blue image and to detect projecting defects and grime according to positional relationships between light and dark regions in each image.

However, there are cases in which dark regions and light regions appear intricately in images due to surface asperities of an object, and therefore defects in the form of depressions and projections and grime cannot precisely be separated as in the case of conventional techniques.

SUMMARY OF INVENTION

It is an object of the present invention to suppress over-detection of defects by excluding defect candidates (false defects) that in actuality do not correspond to defects from defect candidates extracted by self-comparison with high accuracy.

The present invention is intended for a defect detection device for detecting a surface defect in an object. A defect detection device according to a preferable mode of the present invention includes an image capturing part for capturing an image of an object to acquire a captured image, a storage for storing a reference image that corresponds to the captured image, and a defect acquisition part for detecting a defect candidate region on the basis of at least one of a difference and a ratio between each pixel value in the captured image and a pixel value corresponding to the pixel value of the captured image in an image that is obtained by performing one processing out of expansion processing and reduction processing on the captured image and then performing the other processing out of the expansion processing and the reduction processing, different from the one processing, on the captured image, detecting a mask region on the basis of at least one of a difference and a ratio between each pixel value in the reference image and a pixel value corresponding to the pixel value of the reference image in an image that is obtained by performing the one processing on the reference image and then performing the other processing on the reference image, excluding a region of the defect candidate region that overlaps with the mask region from a defect candidate, and acquiring presence of a defect in the captured image on the basis of the defect candidate region.

According to the present invention, out of the defect candidate extracted by the self-comparison of the captured image, a region that overlaps with the self-comparison result obtained from the reference image can be excluded from defect candidates. As a result, a portion that is not a defect included in the captured image but that is lighter or darker than the surroundings can be removed from defect candidates, and over-detection can be suppressed.

Preferably, the defect acquisition part acquires presence of a first defect and a second defect different from the first defect in the captured image. The defect acquisition part includes a first defect acquisition part for detecting a first defect candidate region on the basis of at least one of a difference and a ratio between each pixel value in the captured image and a pixel value corresponding to the pixel value of the captured image in an image that is obtained by performing expansion processing on the captured image and then performing reduction processing on the captured image, detecting a first mask region on the basis of at least one of a difference and a ratio between each pixel value in the reference image and a pixel value corresponding to the pixel value of the reference image in an image that is obtained by performing expansion processing on the reference image and then performing reduction processing on the reference image, excluding a region of the first defect candidate region that overlaps with the first mask region from a first defect candidate, and acquiring presence of a first defect in the captured image on the basis of the first defect candidate region, and a second defect acquisition part for detecting a second defect candidate region on the basis of at least one of a difference and a ratio between each pixel value in the captured image and a pixel value corresponding to the pixel value of the captured image in an image that is obtained by performing reduction processing on the captured image and then performing expansion processing on the captured image, detecting a second mask region on the basis of at least one of a difference and a ratio between each pixel value in the reference image and a pixel value corresponding to the pixel value of the reference image in an image that is obtained by performing reduction processing on the reference image and then performing expansion processing on the reference image, excluding a region of the second defect candidate region that overlaps with the second mask region from a second defect candidate, and acquiring presence of a second defect in the captured image on the basis of the second defect candidate region.

The defect acquisition part is capable of acquiring the first defect and the second defect different from the first defect, i.e., different types of defects, by changing the sequence of the expansion processing and the reduction processing. This more reliability prevents omissions of a defect included in the captured image in detection.

Preferably, the first defect acquisition part acquires the presence of a first defect in the captured image on the basis of the first defect candidate region by, after aligning the captured image and the reference image, acquiring a region where the captured image is darker than the reference image as a third defect candidate region on the basis of the difference image between the captured image and the reference image and excluding a region of the first defect candidate region that does not overlap with the third defect candidate region from the first defect candidate. The second defect acquisition part acquires the presence of a second defect in the captured image on the basis of the second defect candidate region by, after aligning the captured image and the reference image, acquiring a region where the captured image is lighter than the reference image as a fourth defect candidate region on the basis of the difference image between the captured image and the reference image and excluding a region of the second defect candidate region that does not overlap with the fourth defect candidate region from the second defect candidate.

Out of the defect candidate detected by so-called self-comparison, a region that does not overlap with the defect candidate detected from the difference image between the captured image and the reference image (defect candidate detected by so-called other-related comparison) are excluded from defect candidates. This more reliably suppresses over-detection.

The present invention is also intended for a defect detection method of detecting a surface defect in an object. A defect detection method according to a preferable mode of the present invention includes a) an image capturing step of capturing an image of an object with an image capturing part to acquire a captured image, b) a defect candidate region detection step of detecting a defect candidate region on the basis of at least one of a difference and a ratio between each pixel value in the captured image and a pixel value corresponding to the pixel value of the captured image in an image that is obtained by performing one processing out of expansion processing and reduction processing on the captured image and then performing the other processing out of the expansion processing and the reduction processing, different from the one processing, on the captured image, c) a mask region detection step of, after a reference image corresponding to the captured image is prepared, detecting a mask region on the basis of at least one of a difference and a ratio between each pixel value in the reference image and a pixel value corresponding to the pixel value of the reference image in an image that is obtained by performing the one processing on the reference image and then performing the other processing on the reference image, and d) a defect candidate excluding step of excluding a region of the defect candidate region that overlaps with the mask region from a defect candidate and then acquiring presence of a defect in the captured image on the basis of the defect candidate region.

According to the present invention, out of the defect candidate extracted by the self-comparison of the captured image, a region that overlaps with the self-comparison result obtained from the reference image can be excluded from defect candidates. As a result, a portion that is not a defect included in the captured image but that is lighter or darker than the surroundings can be removed from defect candidates, and over-detection can be suppressed.

The present invention is also intended for a program for causing a computer to detect a defect in a target region of a surface of an object from a plurality of images of the target region. Execution of a program according to a preferable mode of the present invention by a computer causes the computer to execute a) a step of preparing a captured image acquired by capturing an image of the target region, and a corresponding reference image, b) a defect candidate region detection step of detecting a defect candidate region on the basis of at least one of a difference and a ratio between each pixel value in the captured image and a pixel value corresponding to the pixel value of the captured image in an image that is obtained by performing one processing out of expansion processing and reduction processing on the captured image and then performing the other processing out of the expansion processing and the reduction processing, different from the one processing, on the captured image, c) a mask region detection step of, after a reference image corresponding to the captured image is prepared, detecting a mask region on the basis of at least one of a difference and a ratio between each pixel value in the reference image and a pixel value corresponding to the pixel value of the reference image in an image that is obtained by performing the one processing on the reference image and then performing the other processing on the reference image, and d) a defect candidate excluding step of excluding a region of the defect candidate region that overlaps with the mask region from a defect candidate and then acquiring presence of a defect in the captured image on the basis of the defect candidate region.

By installing the program on the computer, it is possible to obtain a defect detection device that excludes, out of the defect candidate detected by the self-comparison of the captured image, a region that overlaps with the self-comparison result obtained from the reference image from defect candidates. As a result, a portion that is not a defect included in the captured image but that is lighter or darker than the surroundings can be removed from defect candidates, and over-detection can be suppressed.

Another object of the present invention is to suppress over-detection of defects even if an image that includes a defect is used as a reference image.

A defect detection device according to another preferable mode of the present invention includes an image capturing part for capturing an image of an object to acquire a captured image, a storage for storing a reference image that corresponds to the captured image, and a defect acquisition part for acquiring presence of a defect in the captured image. The defect acquisition part includes a self-comparison defect candidate acquisition part for acquiring a self-comparison defect candidate region on the basis of at least one of a difference and a ratio between each pixel value in the captured image and a pixel value corresponding to the pixel value of the captured image in an image that is obtained by performing one processing out of expansion processing and reduction processing on the captured image and then performing the other processing out of the expansion processing and the reduction processing, different from the one processing, on the captured image, an other-image-related comparison defect candidate acquisition part for, after aligning the captured image and the reference image, in a case where the one processing is the expansion processing, acquiring a region where the captured image is darker than the reference image as an other-image-related comparison defect candidate region on the basis of at least one of a difference image and a ratio image between the captured image and the reference image, and in a case where the one processing is the reduction processing, acquiring a region where the captured image is lighter than the reference image as the other-image-related comparison defect candidate region on the basis of at least one of the difference image and the ratio image between the captured image and the reference image, and a defect candidate narrowing part for acquiring, as a defect candidate region, a region of overlap between the self-comparison defect candidate region output from the self-comparison defect candidate acquisition part and the other-image-related comparison defect candidate region output from the other-image-related comparison defect candidate acquisition part.

According to the present invention, a region of overlap between the self-comparison defect candidate detected on the basis of the self-comparison of the captured image (comparison between the captured image itself and the image obtained by performing expansion and reduction processing or reduction and expansion processing on the captured image) and the other image-related comparison defect candidate detected on the basis of the other image-related comparison between the captured image and the reference image is acquired as a defect candidate region. As a result, noise included in at least one of the self-comparison defect candidate and the other image-related comparison defect candidate can be removed, and over-detection can be suppressed.

Preferably, the self-comparison defect candidate acquisition part is configured to further detect a self-comparison mask region on the basis of at least one of a difference and a ratio between each pixel value in the reference image and a pixel value corresponding to the pixel value of the reference image in an image that is obtained by performing the one processing on the reference image and then performing the other processing on the reference image, exclude a region of the self-comparison defect candidate region that overlaps with the self-comparison mask region from the self-comparison defect candidate region, and then output the self-comparison defect candidate region to the defect candidate narrowing part.

The self-comparison defect candidate acquisition part excludes a region that is not a defect included in the self-comparison defect candidate detected by the so-called self-comparison of the captured image, on the basis of the self-comparison mask region obtained as a self-comparison result from the reference image. This more reliably suppresses over-detection.

The present invention is also intended for a defect detection method of detecting a surface defect in an object. A defect detection method according to another preferable mode of the present invention includes a) an image capturing step of capturing an image of an object with an image capturing part to acquire a captured image, b) a self-comparison defect candidate acquisition step of acquiring a self-comparison defect candidate region on the basis of at least one of a difference and a ratio between each pixel value in the captured image and a pixel value corresponding to the pixel value of the captured image in an image that is obtained by performing one processing out of expansion processing and reduction processing on the captured image and then performing the other processing out of the expansion processing and the reduction processing, different from the one processing, on the captured image, c) an other-image-related comparison defect candidate acquisition step of, after a reference image corresponding to the captured image has been prepared and after aligning the captured image and the reference image, in a case where the one processing is the expansion processing, acquiring a region where the captured image is darker than the reference image as an other-image-related comparison defect candidate region on the basis of at least one of a difference image and a ratio image between the captured image and the reference image, and in a case where the one processing is the reduction processing, acquiring a region where the captured image is lighter than the reference image as the other-image-related comparison defect candidate region on the basis of at least one of the difference image and the ratio image between the captured image and the reference image, and d) a defect candidate narrowing step of acquiring, as a defect candidate region, a region of overlap between the self-comparison defect candidate region acquired in the self-comparison defect candidate acquisition step and the other-image-related comparison defect candidate region acquired in the other-image-related comparison defect candidate acquisition step.

According to the present invention, a region of overlap between the self-comparison defect candidate detected on the basis of the self-comparison of the captured image and the other image-related comparison defect candidate detected on the basis of the other image-related comparison between the captured image and the reference image is acquired as a defect candidate region. As a result, noise included in at least one of the self-comparison defect candidate and the other image-related comparison defect candidate can be removed, and over-detection can be suppressed.

The present invention is also intended for a program for causing a computer to detect a defect in a target region of a surface of an object from a plurality of images of the target object. Execution of a program according to a preferable mode of the present invention by a computer causes the computer to execute a) a step of preparing a captured image acquired by capturing an image of the target region, and a corresponding reference image, b) a self-comparison defect candidate acquisition step of acquiring a self-comparison defect candidate region on the basis of at least one of a difference and a ratio between each pixel value in the captured image and a pixel value corresponding to the pixel value of the captured image in an image that is obtained by performing one processing out of expansion processing and reduction processing on the captured image and then performing the other processing out of the expansion processing and the reduction processing, different from the one processing, on the captured image, c) an other-image-related comparison defect candidate acquisition step of, after aligning the captured image and the reference image, in a case where the one processing is the expansion processing, acquiring a region where the captured image is darker than the reference image as an other-image-related comparison defect candidate region on the basis of at least one of a difference image and a ratio image between the captured image and the reference image, and in a case where the one processing is the reduction processing, acquiring a region where the captured image is lighter than the reference image as the other-image-related comparison defect candidate region on the basis of at least one of the difference image and the ratio image between the captured image and the reference image, and d) a defect candidate narrowing step of acquiring, as a defect candidate region, a region of overlap between the self-comparison defect candidate region acquired in the self-comparison defect candidate acquisition step and the other-image-related comparison defect candidate region acquired in the other-image-related comparison defect candidate acquisition step.

By installing the program on the computer, it is possible to obtain a defect detection device that acquires a region of overlap between the self-comparison defect candidate detected on the basis of the self-comparison of the captured image and the other image-related comparison defect candidate detected on the basis of the other image-related comparison between the captured image and the reference image as a defect candidate region. As a result, noise included in at least one of the self-comparison defect candidate and the other image-related comparison defect candidate can be removed, and over-detection can be suppressed.

Yet another object of the present invention is to suppress over-detection of defects by excluding a defect candidate derived from a surface color of the object from defect candidates with high accuracy.

A defect detection device according to another preferable mode of the present invention includes a light emission part capable of emitting light to an object in a plurality of directional illumination states that are different from one another, an image capturing part for acquiring an image of a target region of a surface of the object as a captured image, an image capture controller for controlling an illumination state of the light emission part and acquisition of an image by the image capturing part, and a defect acquisition part for acquiring, from at least one captured image used in defect detection, one of a dark region and a light region that are respectively darker and lighter than in a corresponding reference image as a defect candidate region while referencing the reference image, acquiring, from each of a plurality of captured images acquired in a plurality of illumination states, the other of a dark region and a light region that are respectively darker and lighter than in a corresponding reference image as a lightness/darkness inverted region while referencing the reference image, and excluding, among the defect candidate regions, a defect candidate region that does not overlap by a prescribed criterion or more with any of the lightness/darkness inverted regions from a defect candidate and then acquiring presence of a defect on the basis of the defect candidate regions.

According to the present invention, over-detection of defects can be suppressed.

Preferably, the at least one captured image used in defect detection is included in the plurality of captured images acquired in the plurality of illumination states.

Preferably, the defect acquisition part acquires, from the at least one captured image used in defect detection, the other of the dark region and the light region that are respectively darker and lighter than in the corresponding reference image as another defect candidate region while referencing the reference image, and acquires the lightness/darkness inverted region that corresponds to the defect candidate region when acquiring the another defect candidate region.

Preferably, the defect acquisition part acquires a first defect candidate region by a first method and a second defect candidate region by a second method different from the first method from the at least one captured image used in defect detection, and acquires the defect candidate region on the basis of the first defect candidate region and the second defect candidate region.

More preferably, the first method is a method of aligning a captured image and a reference image and then acquiring the first defect candidate region from a difference image between the captured image and the reference image, and the second method is a method of performing minute region removal processing on a captured image and a reference image and then acquiring the second defect candidate region from a difference image between the captured image and the reference image.

The present invention is also intended for a defect detection method of detecting a surface defect in an object. A defect detection method according to a preferable mode of the present invention includes the steps of a) acquiring a plurality of captured images by acquiring an image of a target region of a surface of an object with an image capturing part while the object is irradiated with light in each of a plurality of directional illumination states that are different from one another, b) acquiring, from at least one captured image used in defect detection, one of a dark region and a light region that are respectively darker and lighter than in a corresponding reference image as a defect candidate region while referencing the reference image, c) acquiring, from each of a plurality of captured images, the other of a dark region and a light region that are respectively darker and lighter than in a corresponding reference image as a lightness/darkness inverted region while referencing the reference image, and d) excluding, among the defect candidate regions, a defect candidate region that does not overlap by a prescribed criterion or more with any of the lightness/darkness inverted regions from a defect candidate and then acquiring presence of a defect on the basis of the defect candidate regions.

Preferably, the at least one captured image used in defect detection is included in the plurality of captured images acquired in the plurality of illumination states.

Preferably, the defect detection method further comprising the step of e) acquiring, from the at least one captured image used in defect detection, the other of the dark region and the light region that are respectively darker and lighter than in the corresponding reference image as another defect candidate region while referencing the reference image. The step c) is included in the step e).

The present invention is also intended for a program for causing a computer to detect a defect in a target region of a surface of an object from a plurality of images of the target region. Execution of a program according to a preferable mode of the present invention by a computer causes the computer to execute the steps of a) preparing a plurality of captured images of the target region acquired in a plurality of directional illumination states that are different from one another, and a plurality of corresponding reference images, b) acquiring, from at least one captured image used in defect detection, one of a dark region and a light region that are respectively darker and lighter than in a corresponding reference image as a defect candidate region while referencing the reference image, c) acquiring, from each of a plurality of captured images, the other of a dark region and a light region that are respectively darker and lighter than in a corresponding reference image as a lightness/darkness inverted region while referencing the reference image, and d) excluding, among the defect candidate regions, a defect candidate region that does not overlap by a prescribed criterion or more with any of the lightness/darkness inverted regions from a defect candidate and then acquiring presence of a defect on the basis of the defect candidate regions.

These and other objects, features, aspects and advantages will become more apparent from said following detailed description when taken in conjunction with said accompanying drawings.

MODES FOR CARRYING OUT INVENTION

Figure 1:
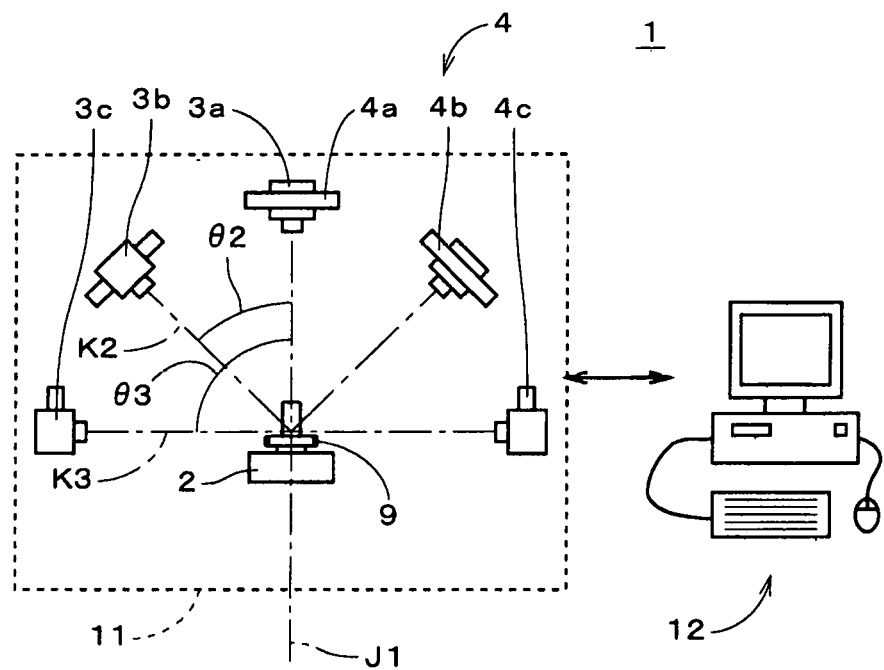
FIG. 1 illustrates a configuration of a defect detection device.
Figure 2:
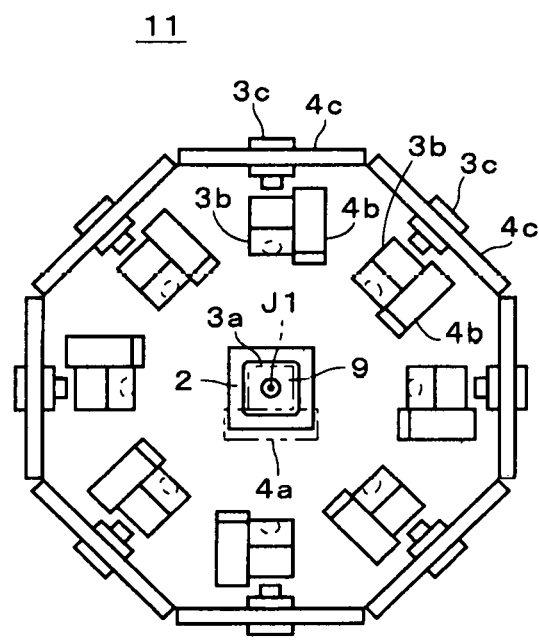
FIG. 2 is a plan view illustrating a main body of the defect detection device.

FIG. 1 illustrates a configuration of a defect detection device 1 according to an embodiment of the present invention. FIG. 2 is a plan view of a main body 11 of the defect detection device 1. The defect detection device 1 is a device for detecting the external appearance of a three-dimensional object 9 that has a non-mirror finish surface, and detects a surface defect in the object 9.

The object 9 is, for example, a metal component formed by forging or casting. The object 9 has a satin-finish surface with microscope asperities, i.e., a matte-finish surface. In other words, the surface of the object 9 has a luster while irregularly reflecting light. The glossiness of the surface of the object 9 is preferably in the range of approximately 20 to approximately 60. The glossiness as used herein is an indicator that represents the degree of glossiness of an object surface one-dimensionally while focusing on, for example, the ratio of regularly reflected light and the directional distribution of diffused and reflected light. The glossiness is measured with a glossmeter that is compliant with a glossiness measurement method according to industrial standards such as JIS.

The surface of the object 9 is processed by shot blasting such as sandblasting or steel shot blasting using a predetermined projecting material, and has a shape (so-called R-shape) obtained by removing sharp edges at the boundaries and edges of upper and lower surfaces and side surfaces or fins formed by molding. The object 9 is, for example, any of various components used in a universal joint and is, for example, a metal component used in the actuator of a vehicle, an aircraft, or a power generator.

Defects on the surface of the object 9 are sites where there are depressions or projections in contrast to the ideal shape thereof. Examples of the defects include dents, scratches, and machining defects and so on. Defects may also be foreign materials adhering to the surface.

The defect detection device 1 includes the main body 11 and a computer 12 as illustrated in FIG. 1. The main body 11 includes a holder 2, a plurality of image capturing parts 3 (which are given reference signs 3a, 3b, and 3c in FIG. 1, but may be indicated by reference sign 3 when there is no need to distinguish therebetween), and a light emission part 4. The object 9 is held by the holder 2. The main body 11 is provided with a light-shielding cover (not shown) that prevents external light from reaching the holder 2, and the holder 2, the image capturing parts 3, and the light emission part 4 are provided in the light-shielding cover.

In the case of automatically inspecting the entire surface of the object 9, another main body 11 is provided, and a mechanism for turning the object 9 upside down and transporting the object 9 is provided between the two main bodies 11.

As illustrated in FIGS. 1 and 2, the image capturing parts 3 include one upper image capturing part 3a, eight oblique image capturing parts 3b, and eight lateral image capturing parts 3c. The upper image capturing part 3a is disposed above the holder 2. The upper image capturing part 3a enables the acquisition of an image of the object 9 on the holder 2 captured from directly above.

As illustrated in FIG. 2, the eight oblique image capturing parts 3b are disposed around the holder 2 when the main body 11 is viewed vertically from above (i.e., when the main body 11 is viewed in plan view). The eight oblique image capturing parts 3b are arranged at an angular interval (angular pitch) of 45° in the circumferential direction about a central axis J1 that passes through the center of the holder 2 and points in the up-down direction. As illustrated in FIG. 1, an angle θ2 formed by an optical axis K2 of each oblique image capturing part 3 and the central axis J1 in a plane that contains the optical axis K2 and the central axis J1 is approximately 45°. Each oblique image capturing part 3b enables the acquisition of an image of the object 9 on the holder 2 captured from obliquely above. The angle θ2 is not limited to 45° as long as the image of the object 9 is captured from obliquely above, and it may preferably be set to any angle in the range of 15 to 75°.

Similarly to the eight oblique image capturing parts 3b, the eight lateral image capturing parts 3c are also disposed around the holder 2 when the main body 11 is viewed in plan view. The eight lateral image capturing parts 3c are arranged at an angular interval of 45° in the circumferential direction. An angle θ3 formed by an optical axis K3 of each lateral image capturing part 3c and the central axis J1 in a plane that contains the optical axis K3 and the central axis J1 is approximately 90°. Each lateral image capturing part 3c enables the acquisition of an image of the object 9 on the holder 2 captured from the side.

The upper image capturing part 3a, the oblique image capturing parts 3b, and the lateral image capturing parts 3c include two-dimensional image sensors such as CCDs (charge coupled devices) or CMOSs (complementary metal-oxide semiconductors) and acquire multitone images. The upper image capturing part 3a, the oblique image capturing parts 3b, and the lateral image capturing parts 3c are supported by supporters (not shown).

The light emission part 4 includes one upper light source 4a, eight oblique light sources 4b, and eight lateral light sources 4c. The upper light source 4a is adjacent to the upper image capturing part 3a. The upper light source 4a has a plurality of LEDs (light-emitting diodes) aligned perpendicular to the central axis J1, i.e., aligned horizontally. The upper light source 4a emits light to the object 9 on the holder 2 from approximately directly above.

The eight oblique light sources 4b are disposed around the holder 2 when the main body 11 is viewed in plan view. The oblique light sources 4b are respectively adjacent to the oblique image capturing parts 3b. The eight oblique light sources 4b are arranged at an angular interval of 45° in the circumferential direction. Each oblique light source 4b has a plurality of LEDs aligned approximately perpendicular to the optical axis K2. Each oblique light source 4b is capable of emitting light to the object 9 on the holder 2 from obliquely above.

The eight lateral light sources 4c are disposed around the holder 2 when the main body 11 is viewed in plan view. The lateral light sources 4c are respectively adjacent to the lateral image capturing parts 3c. The eight lateral light sources 4c are arranged at an angular interval of 45° in the circumferential direction. Each lateral light source 4c has a plurality of LEDs aligned approximately perpendicular to the optical axis K3 and in the horizontal direction. Thus, the eight lateral light sources 4c form a generally octagonal shape in plan view. Each lateral light source 4c is capable of emitting light to the object 9 on the holder 2 from the side. The upper light source 4a, the oblique light sources 4b, and the lateral light sources 4c may use light sources of other types different from LEDs. Although in the present embodiment, the color of the light is white, the color and wavelength range of the light may be changed in various ways. The light emission part 4 is capable of irradiating the object 9 with diffused light from various directions. Each state in which light is emitted from at least one specific light source and the object 9 is irradiated with directional light is hereinafter referred to as an "illumination state." The light emission part 4 is capable of irradiating the object 9 with light in a plurality of directional illumination states that are different from one another.

Figure 3:
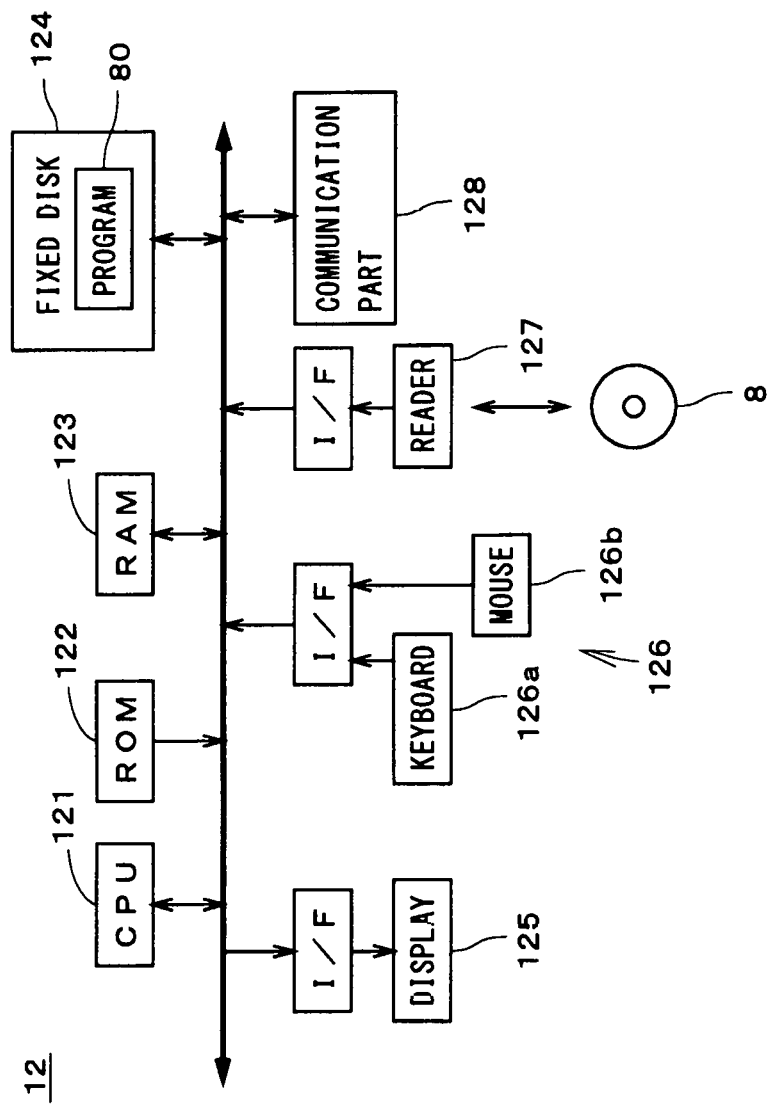
FIG. 3 illustrates a configuration of a computer.

FIG. 3 illustrates a configuration of the computer 12. The computer 12 is configured as a general computer system that includes a CPU 121 that performs various types of arithmetic processing, a ROM 122 that stores master programs, and a RAM 123 that stores various types of information. The computer 12 further includes a fixed disk 124 that stores information, a display 125 that displays various types of information such as images, a keyboard 126a and a mouse 126b (hereinafter, collectively referred to as an "input part 126") that receive input from an operator, a reader 127 that reads information from a computer-readable recording medium 8 such as an optical disk, a magnetic disk, or a magneto-optical disk, and a communication part 128 that transmits and receives signals to and from other components of the defect detection device 1.

In the computer 12, a program 80 is read out in advance from the recording medium 8 via the reader 127 and stored in the fixed disk 124. In accordance with the program 80, the CPU 121 executes arithmetic processing using the RAM 123 and the fixed disk 124. The CPU 121 functions as an operation part in the computer 12. Instead of the CPU 121, a different component that functions as an operation part may be employed.

Figure 4:
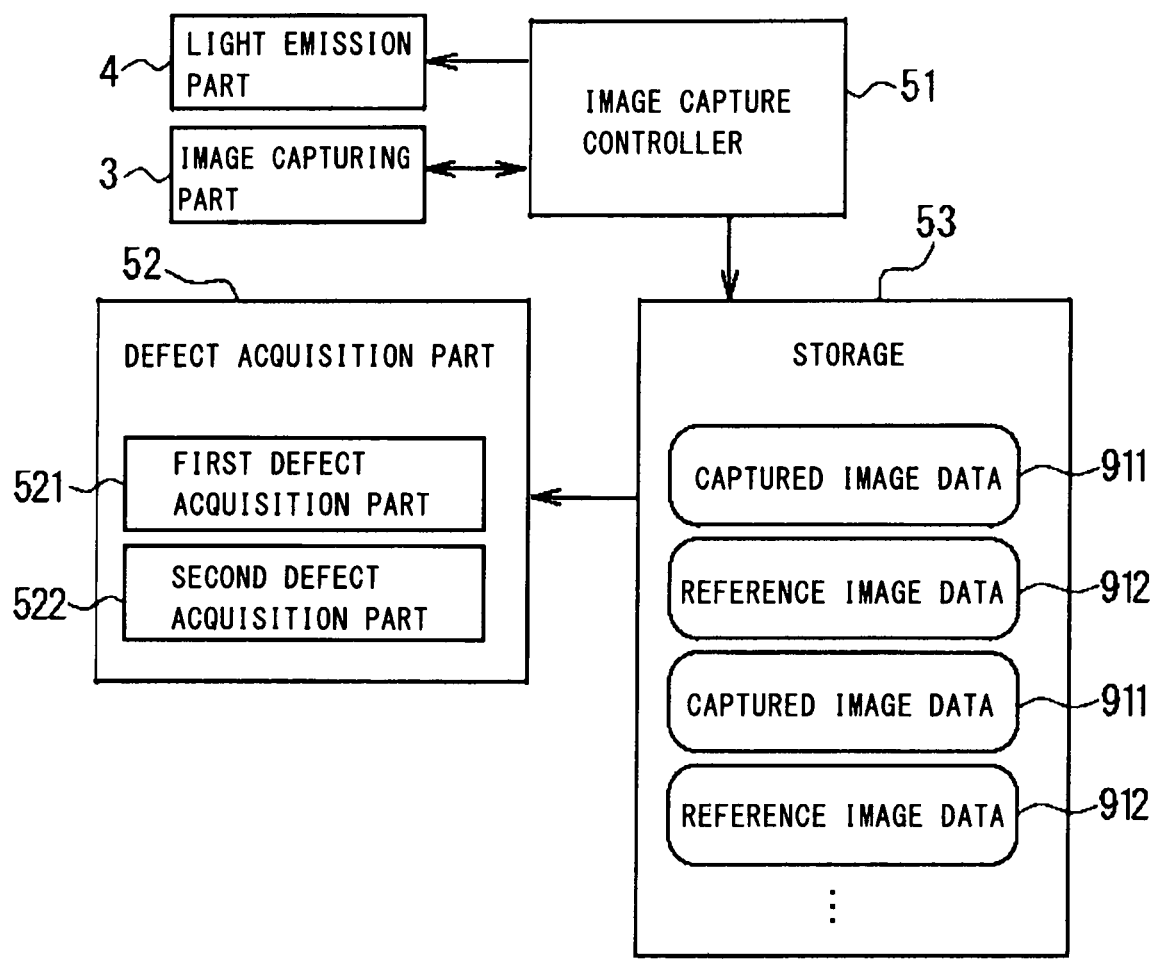
FIG. 4 is a block diagram illustrating a functional configuration implemented by the computer.

FIG. 4 illustrates functions implemented by the computer 12 executing arithmetic processing in accordance with the program 80. In FIG. 4, an image capture controller 51, a defect acquisition part 52, and a storage 53 correspond to the functions implemented by the computer 12. All or some of these functions may be implemented by a dedicated electric circuit. These functions may be implemented by a plurality of computers.

The image capture controller 51 controls the image capturing parts 3 and the light emission part 4 and acquires images of the object 9 (to be precise, data of the images). The image data is stored in the storage 53. Although the image capturing parts 3 are illustrated as one block in FIG. 4, in actuality the upper image capturing part 3a, the oblique image capturing parts 3b, and the lateral image capturing parts 3c are connected to the image capture controller 51.

As will be described later, at least one of the 17 image capturing parts 3 acquires image data every time the image capture controller 51 controls each light source of the light emission part 4 to change the illumination state. Hereinafter, the image acquired by image capture is referred to as a "captured image" and data of the image is referred to as "captured image data." Captured image data 911 is stored in the storage 53. The storage 53 stores data of images of the ideal object 9 in each illumination state as reference image data 912. That is, ideal image data that corresponds to each illumination state of each image capturing part 3 is prepared as the reference image data 912 in the storage 53.

The light illumination state provided by the light emission part 4 refers to a state in which the object 9 is irradiated with light from a specific emission direction. The emission direction is not defined strictly and refers roughly to the direction of light emission. The emission direction is also not intended to limit light to parallel light in the case where light is emitted from only that direction. Emitting light from a certain direction means emitting light from directions deviating from that direction. The number of light emission directions during a single image capture is not limited to one. For example, light may be emitted simultaneously from a plurality of light sources that are spaced from one another.

The defect acquisition part 52 includes a first defect acquisition part 521 and a second defect acquisition part 522. Note that "first defects" according to the present embodiment mean defects that appear dark in images, i.e., "dark defects." "Second defects" according to the present embodiment mean defects that appear light in images, i.e., "light defects."

Various components of the first defect acquisition part 521 will be described hereinafter with reference to FIGS. 5 to 8.

Figure 5:
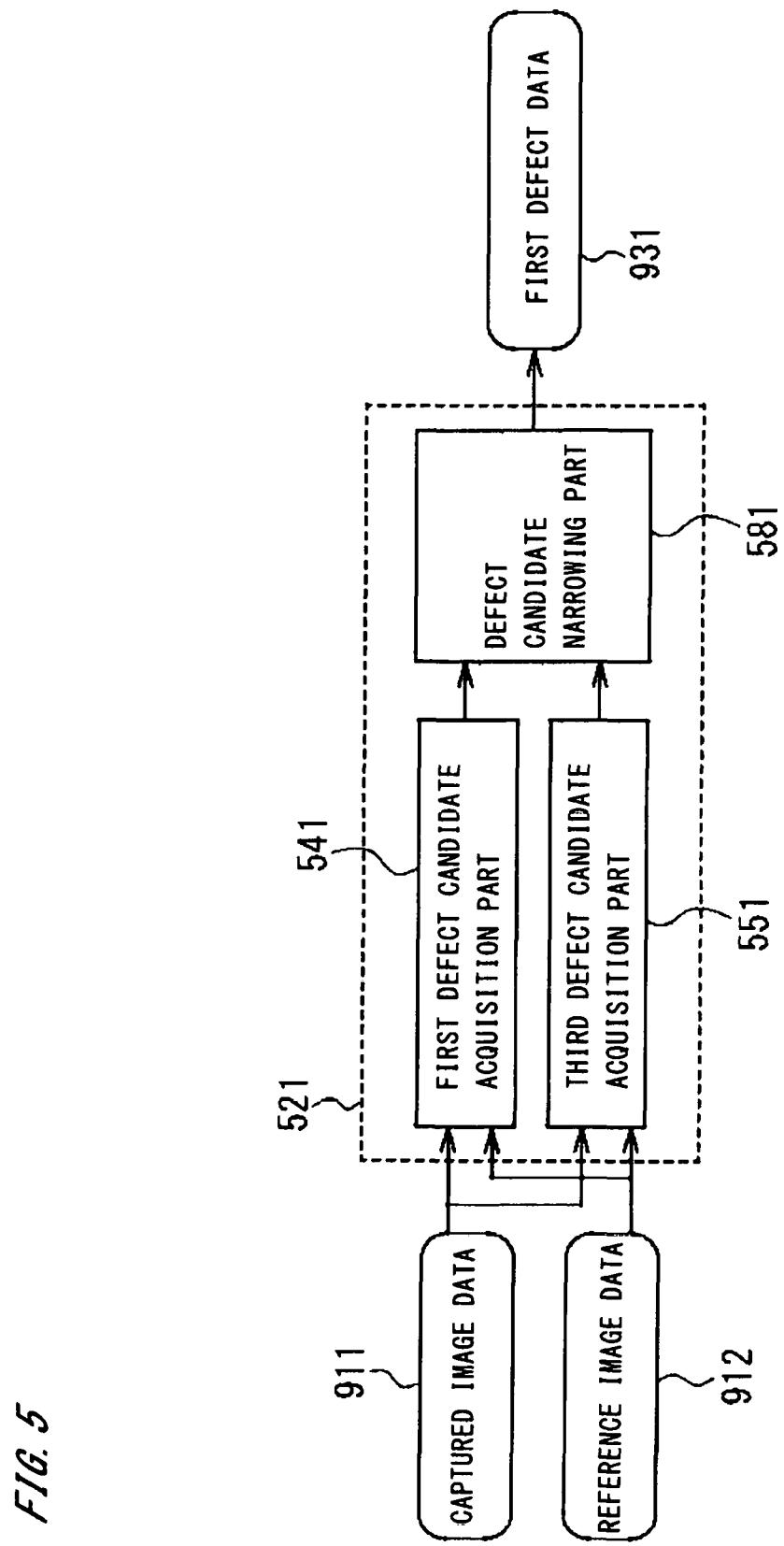
FIG. 5 illustrates a configuration of a first defect acquisition part.
Figure 6:
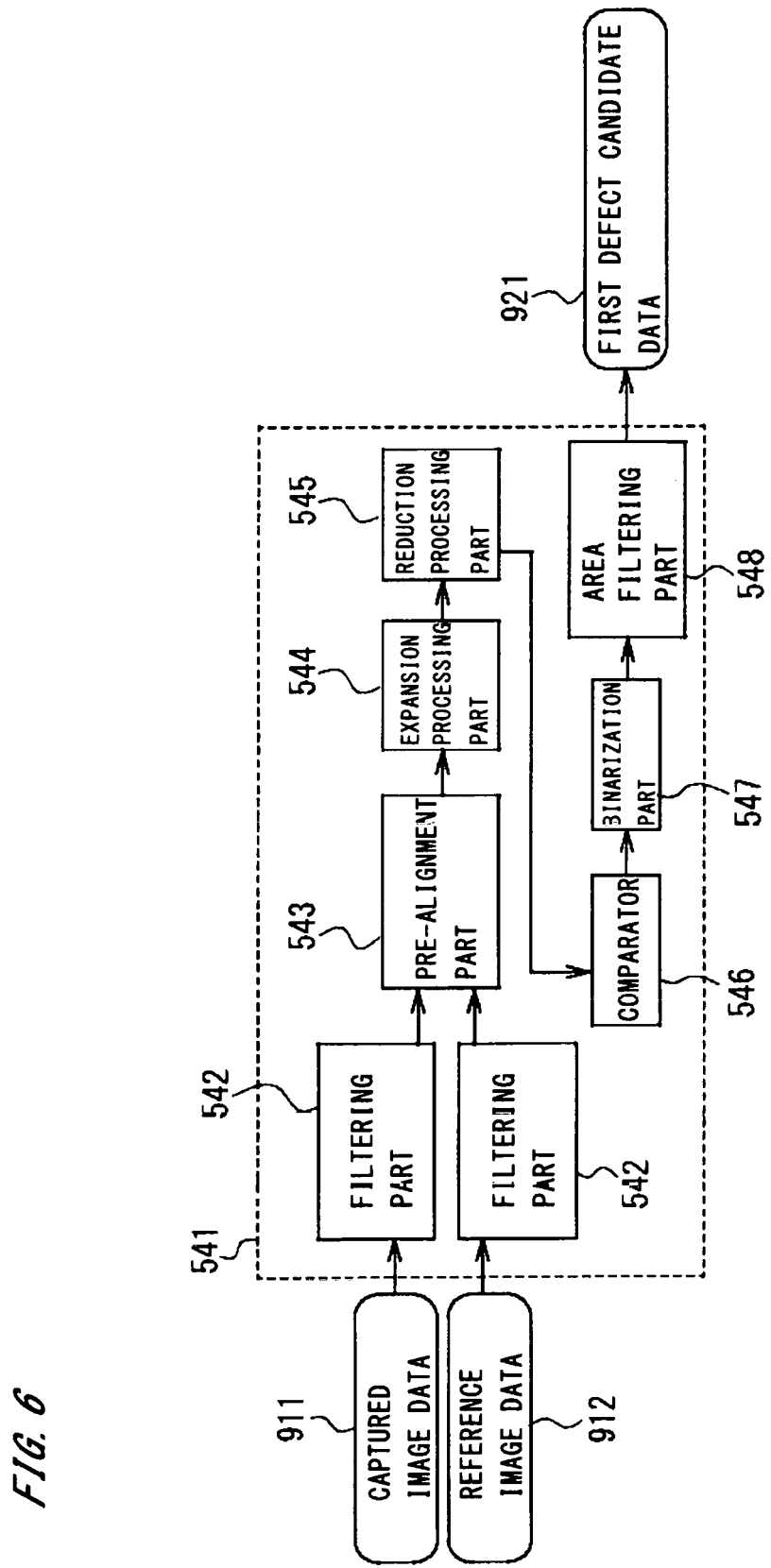
FIG. 6 illustrates a configuration of a first defect candidate acquisition part.

FIG. 5 illustrates a configuration of the first defect acquisition part 521. The first defect acquisition part 521 includes a first defect candidate acquisition part 541, a third defect candidate acquisition part 551, and a defect candidate narrowing part 581. The first defect acquisition part 521 performs processing on the basis of the captured image data 911 and the reference image data 912 that are input, so as to acquire first defect data 931 that is image data indicating first defect regions. The first defect regions are, among regions where the captured image is darker than the reference image, regions that are obtained by removing noise (in the captured image, regions that are essentially not first defects and are detected as first defect candidate regions described later) through various types of processing, which will be described later:

FIG. 6 illustrates a configuration of the first defect candidate acquisition part 541. The first defect candidate acquisition part 541 includes two filtering parts 542, a pre-alignment part 543, an expansion processing part 544, a reduction processing part 545, a comparator 546, a binarization part 547, and an area filtering part 548. The first defect candidate acquisition part 541 performs processing on the basis of the captured image data 911 and the reference image data 912 that are input, so as to acquire first defect candidate data 921 that is image data indicating first defect candidate regions. The first defect candidate regions are regions where the captured image is darker than the reference image.

Figure 7:
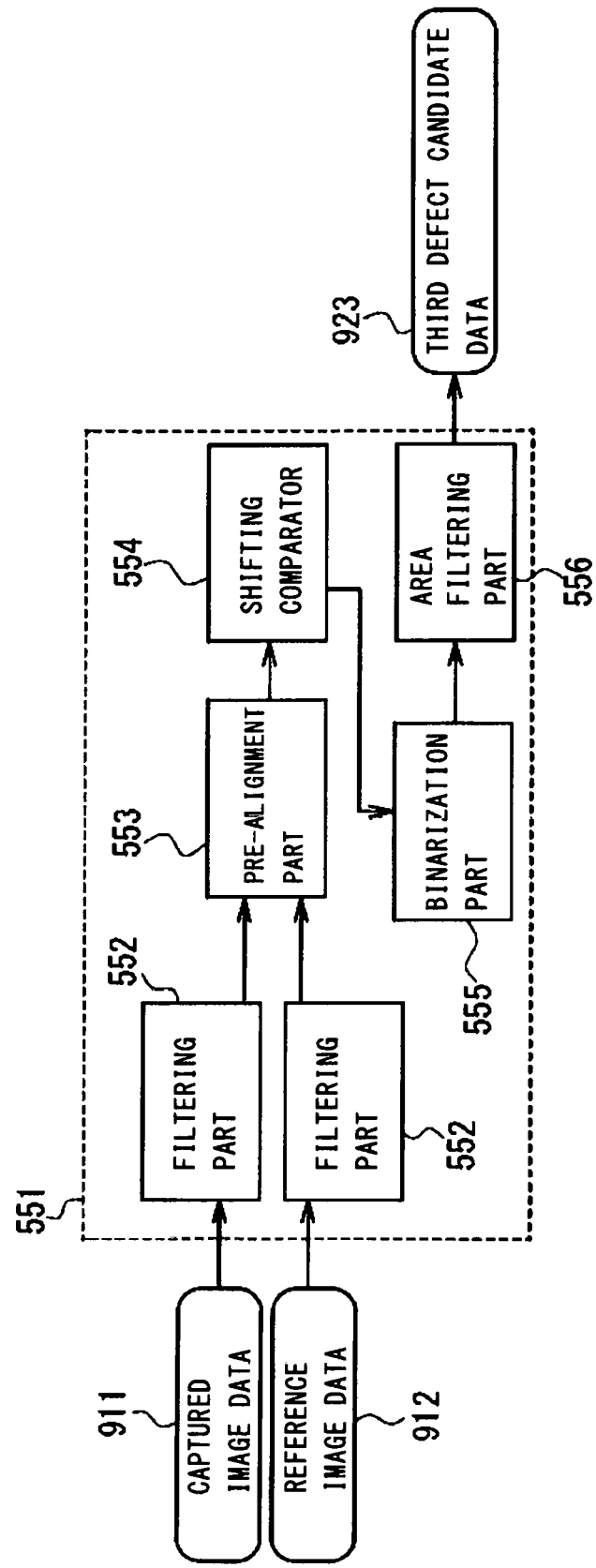
FIG. 7 illustrates a configuration of a third defect candidate acquisition part.

FIG. 7 illustrates a configuration of the third defect candidate acquisition part 551. The third defect candidate acquisition part 551 includes two filtering parts 552, a pre-alignment part 553, a shifting comparator 554, a binarization part 555, and an area filtering part 556. The third defect candidate acquisition part 551 performs processing on the basis of the captured image data 911 and the reference image data 912 that are input, so as to acquire third defect candidate data 923 that is image data indicating third defect candidate regions. The third defect candidate regions are regions where the captured image is darker than the reference image. As will be described later, the method of acquiring the third defect candidate regions differs from the method of acquiring the first defect candidate regions.

Figure 8:
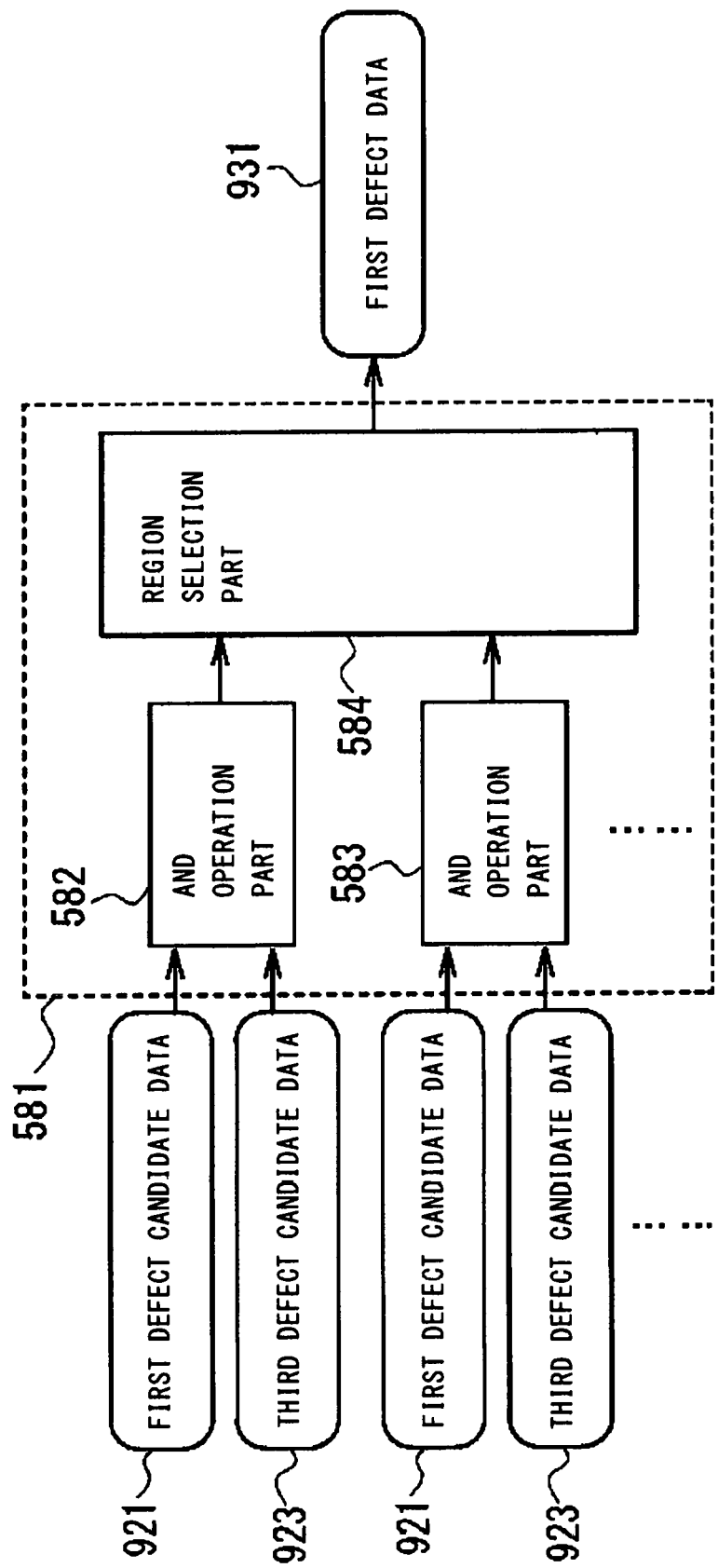
FIG. 8 illustrates a configuration of a defect candidate narrowing part in FIG. 5.

FIG. 8 illustrates a configuration of the defect candidate narrowing part 581. The defect candidate narrowing part 581 includes two or more AND operation parts 582 and 583 and a region selection part 584. The defect candidate narrowing part 581 performs processing on the basis of the first defect candidate data 921 and the third defect candidate data 923 that are input, so as to acquire the first defect data 931.

Next, various components of the second defect acquisition part 522 will be described with reference to FIGS. 9 to 12.

Figure 9:
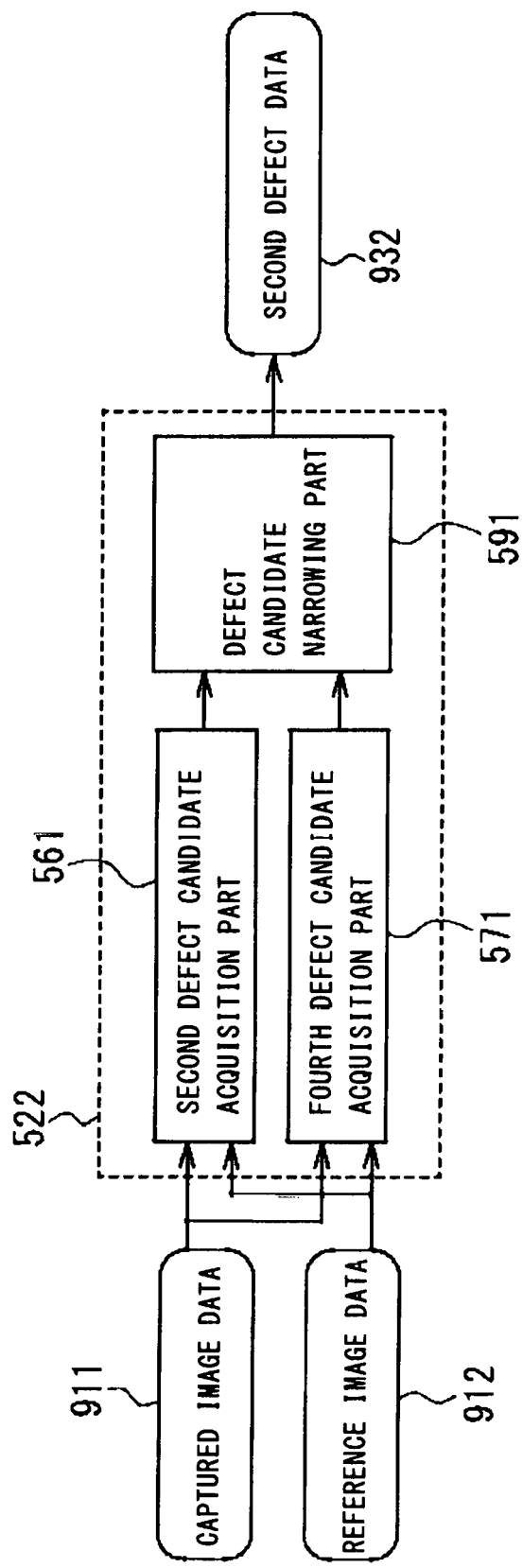
FIG. 9 illustrates a configuration of a second defect acquisition part.

FIG. 9 illustrates a configuration of the second defect acquisition part 522. The second defect acquisition part 522 includes a second defect candidate acquisition part 561, a fourth defect candidate acquisition part 571, and a defect candidate narrowing part 591. The second defect acquisition part 522 performs processing on the basis of the captured image data 911 and the reference image data 912 that are input, so as to acquire second defect data 932 that is image data indicating second defect regions. The second defect regions are, among regions where the captured image is lighter than the reference image, regions that are obtained by removing noise (in the captured image, regions that are essentially not second defects and that are detected as second defect candidate regions described later) through various types of processing, which will be described later.

Figure 10:
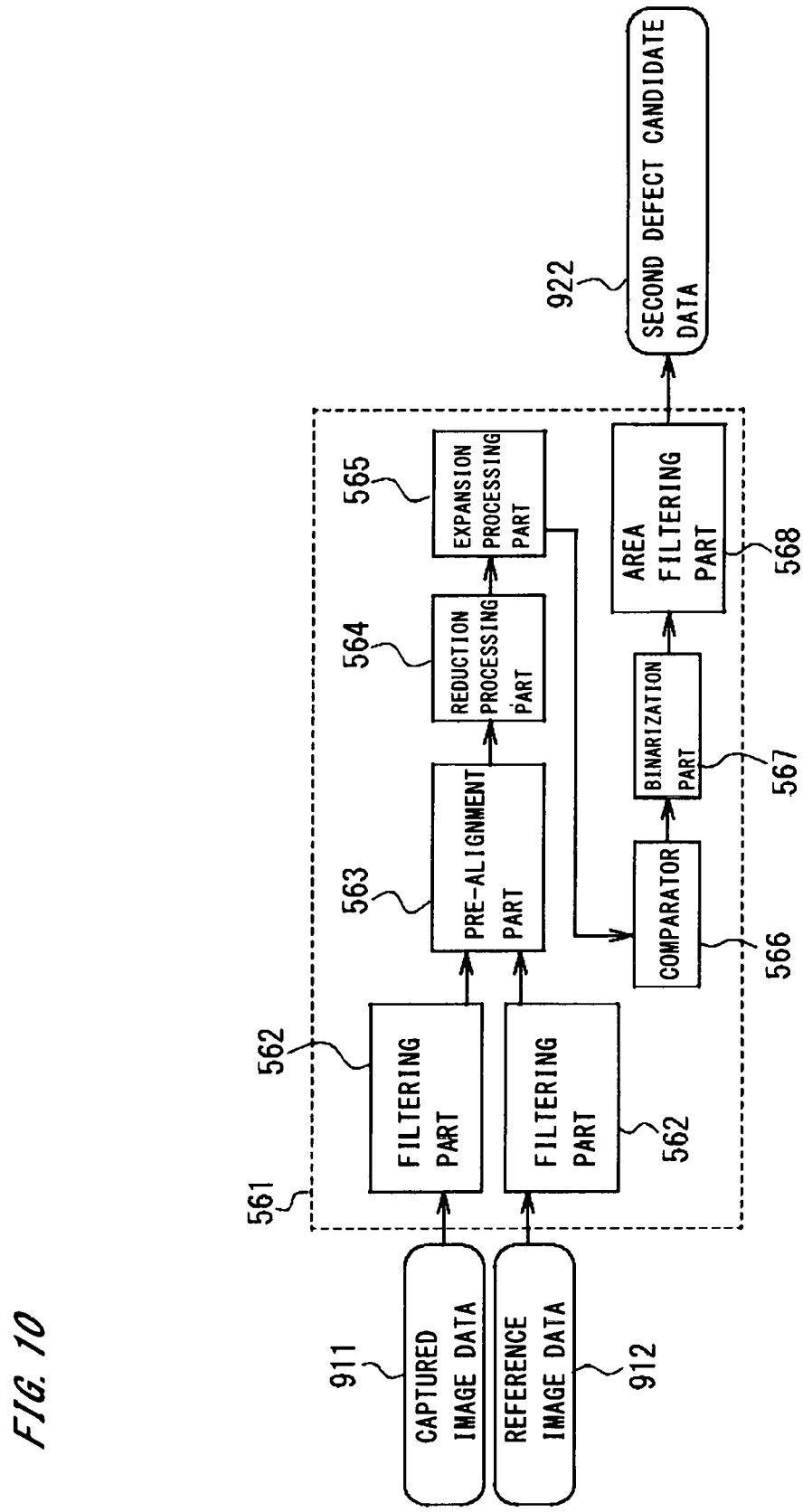
FIG. 10 illustrates a configuration of a second defect candidate acquisition part.

FIG. 10 illustrates a configuration of the second defect candidate acquisition part 561. The second defect candidate acquisition part 561 includes two filtering parts 562, a pre-alignment part 563, a reduction processing part 564, an expansion processing part 565, a comparator 566, a binarization part 567, and an area filtering part 568. The second defect candidate acquisition part 561 performs processing on the basis of the captured image data 911 and the reference image data 912 that are input, so as to acquire second defect candidate data 922 that is image data indicating second defect candidate regions. The second defect candidate regions are regions where the captured image is lighter than the reference image.

Figure 11:
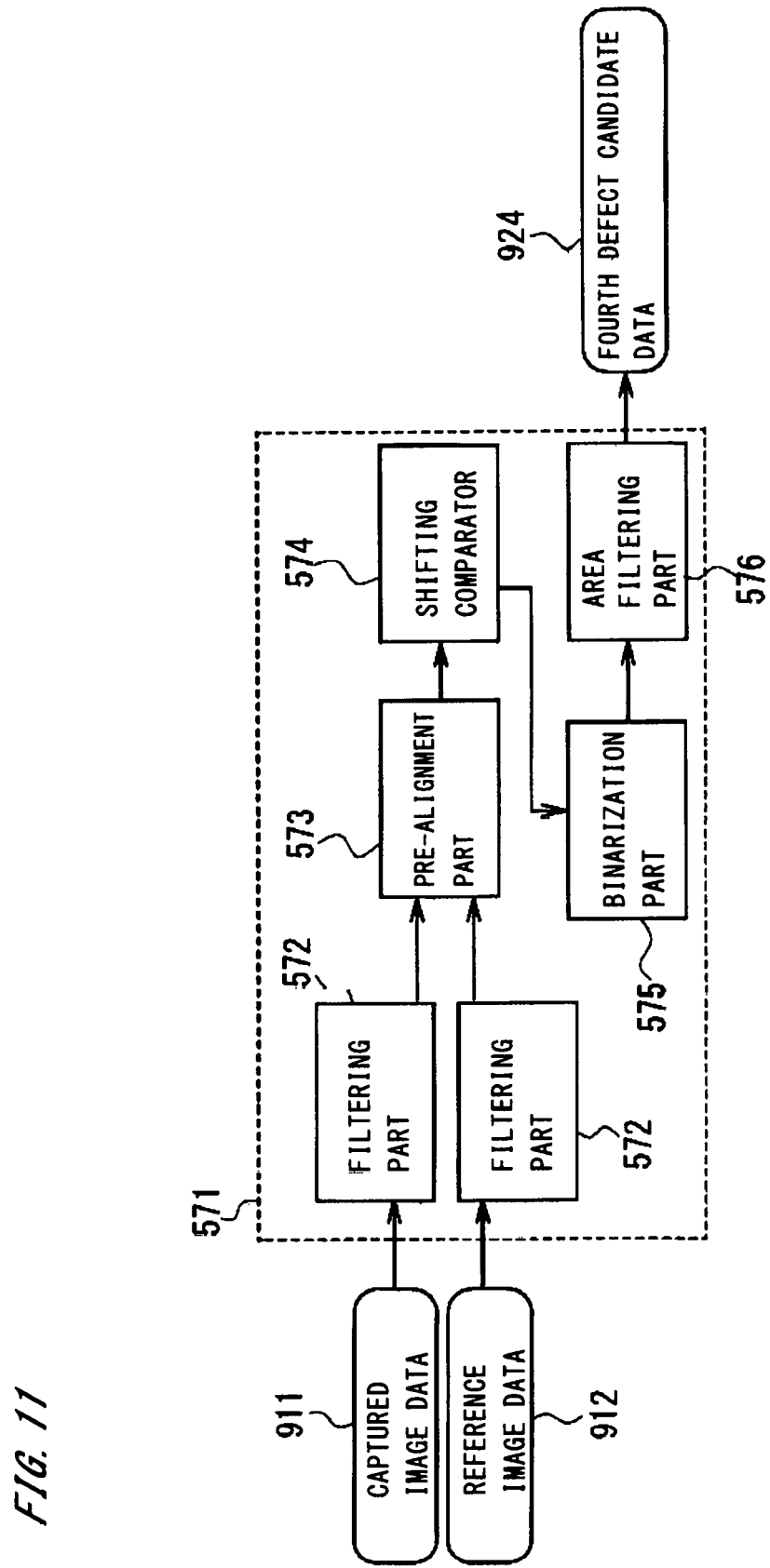
FIG. 11 illustrates a configuration of a fourth defect candidate acquisition part.

FIG. 11 illustrates a configuration of the fourth defect candidate acquisition part 571. The fourth defect candidate acquisition part 571 includes two filtering parts 572, a pre-alignment part 573, a shifting comparator 574, a binarization part 575, and an area filtering part 576. The fourth defect candidate acquisition part 571 performs processing on the basis of the captured image data 911 and the reference image data 912 that are input, so as to acquire fourth defect candidate data 924 that is image data indicating fourth defect candidate regions. The fourth defect candidate regions are regions where the captured image is lighter than the reference image. As will be described later, the method of acquiring the fourth defect candidate regions differs from the method of acquiring the second defect candidate regions.

Figure 12:
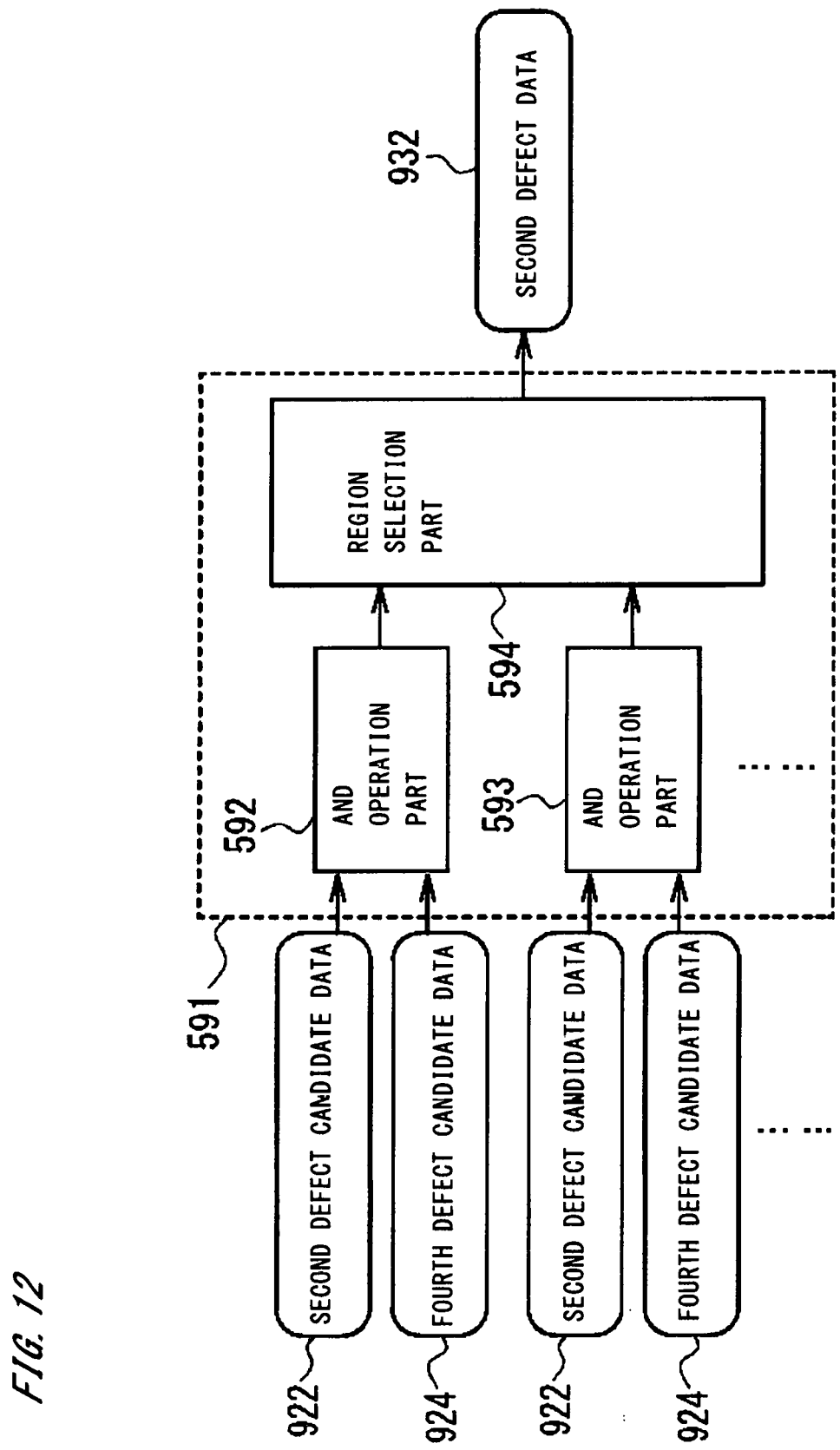
FIG. 12 illustrates a configuration of a defect candidate narrowing part in FIG. 9.

FIG. 12 illustrates a configuration of the defect candidate narrowing part 591. The defect candidate narrowing part 591 includes two or more AND operation parts 592 and 593 and a region selection part 594. The defect candidate narrowing part 591 performs processing on the basis of the second defect candidate data 922 and the fourth defect candidate data 924 that are input, so as to acquire the second defect data 932.

In the case where processing is performed at high speed, a large number of first defect candidate acquisition parts 541 and third defect candidate acquisition parts 551 are provided in the first defect acquisition part 521, and a large number of second defect candidate acquisition parts 561 and fourth defect candidate acquisition parts 571 are provided in the second defect acquisition part 522, so that processing is performed in parallel on a plurality of captured images.

Figure 13:
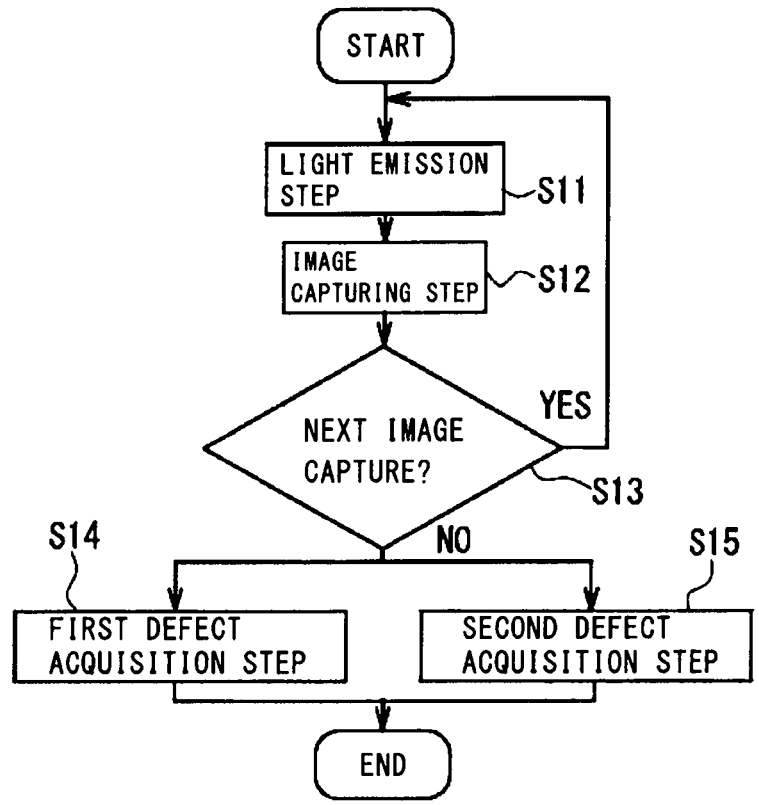
FIG. 13 illustrates a flow of operations of the defect detection device.

FIG. 13 illustrates a flow of operations of the defect detection device 1. First, an object 9 to be inspected is held on the holder 2. The holder 2 is provided with, for example, an abutment part for alignment so that the object 9 is arranged in a predetermined orientation at a predetermined position when a predetermined part of the object 9 comes into contact with the abutment part. The holder 2 may be a stage provided with positioning pins.

Next, the image capture controller 51 changes the illumination state by changing the light source that is turned on, and a selected image capturing part 3 captures an image (steps S11 to S13). That is, a light emission step (step S11) in which the image capture controller 51 issues a lighting instruction to the light emission part 4 and a selected light emission part 4 is turned on, an image capturing step (step S12) in which the image capturing part 3 selected by the image capture controller 51 captures an image of the object 9 to acquire a captured image while the light emission part 4 is on, and a continuation-of-image-capture determination step (step S13) in which, after the image capturing step, the image capture controller 51 determines whether or not to perform the next image capture are executed.

Specifically, one of the lateral image capturing parts 3c is selected, then one of five lateral light sources 4c that are disposed continuously in the horizontal direction and centered on the selected lateral image capturing part 3c is selected and turned on in order, and the lateral image capturing part 3c captures an image every time each lateral light source 4c is turned on. The above-described operations are repeated while changing the lateral image capturing part 3c. In actuality, multiple lateral image capturing parts 3c capture images in each illumination state in order to shorten the operating time. Moreover, all of the lateral light sources 4c are turned on and all of the lateral image capturing parts 3c capture images. Accordingly, each lateral image capturing part 3c acquires six images.

In the case of the oblique image capturing parts 3b, one of the oblique image capturing parts 3b is selected, then one of the eight oblique light sources 4b is selected and turned on in order, and the oblique image capturing part 3b captures an image every time each oblique light source 4b is turned on. The above-described operations are repeated while changing the oblique image capturing part 3b. In actuality, all of the oblique image capturing parts 3b capture images in each illumination state in order to shorten the operating time. Moreover, all of the oblique light sources 4b are turned on and all of the oblique image capturing parts 3b capture images. All of the oblique image capturing parts 3b also capture images when only the upper light source 4a is turned on. Accordingly, each oblique image capturing part 3b acquires 10 images.

In the case of the upper image capturing part 3a, 10 images are acquired while changing the illumination state as in the case of the oblique image capturing parts 3b. In the actual operation, the upper image capturing part 3a captures an image when the oblique image capturing parts 3*b* capture image. This shortens the operating time.

Data of captured images is stored as the captured image data 911 in the storage 53. In the storage 53, data of reference images that correspond to each captured image is prepared as the reference image data 912, as described previously. The reference images indicate the object 9 (so-called non-defective object) that is extracted as a reference for defect inspection in the same illumination states as those of the captured images. The reference image data 912 may be acquired by capturing images of the object 9 that has no defects, or may be acquired as data that indicates an average image of a large number of images of the object 9.

When the image capture controller 51 has completed all the scheduled image capturing steps, then the defect acquisition part 52 executes a first defect acquisition step (step S14) and a second defect acquisition step (step S15). The first defect acquisition step S14 is a step of acquiring first defects included in the captured image. The second defect acquisition step S15 is a step of acquiring second defects included in the captured image. Although in the present embodiment, the first defect acquisition step S14 and the second defect acquisition step S15 are executed in parallel by the defect acquisition part 52, the implementation of the present invention is not limited to this example, and the first defect acquisition step S14 may be executed prior to the second defect acquisition step S15, and vice versa.

In order to simplify the description, processing that is performed on the image data may hereinafter simply be expressed as processing that is performed on images. Description is given on only processing that focuses on one of the image capturing parts 3. The same processing is also performed for the other image capturing parts 3. Although the defect detection device 1 is capable of detecting the presence of first defects (dark defects) and the presence of second defects (light defects), the following description focuses on the first defects, and description of common points of the processing for detecting second defects with the processing for detecting first defects has appropriately been omitted.

Figure 14:
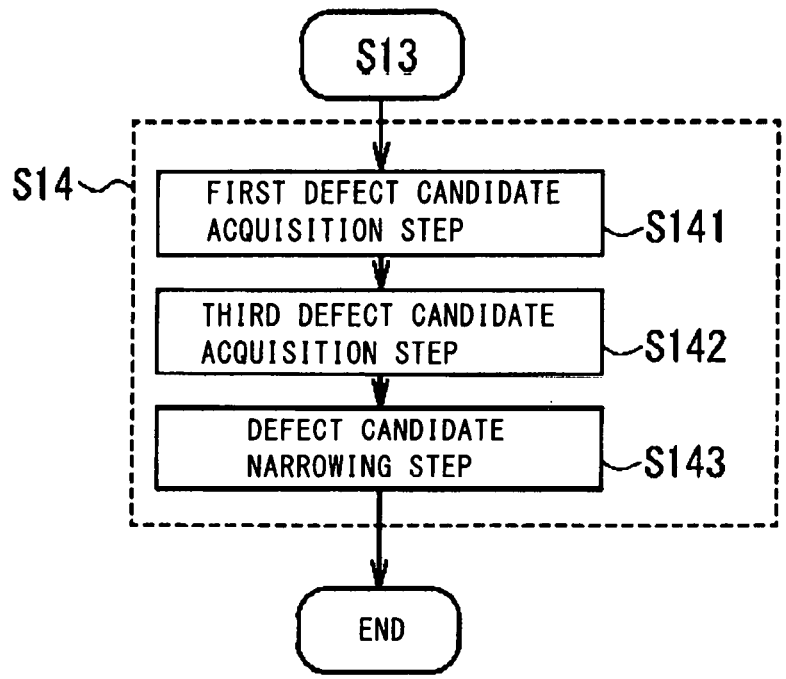
FIG. 14 illustrates a flow of a first defect acquisition step in FIG. 13.

FIG. 14 illustrates the details of the first defect acquisition step S14. The first defect acquisition step S14 includes a first defect candidate acquisition step S141, a third defect candidate acquisition step S142, and a defect candidate narrowing step S143.

Figure 15:
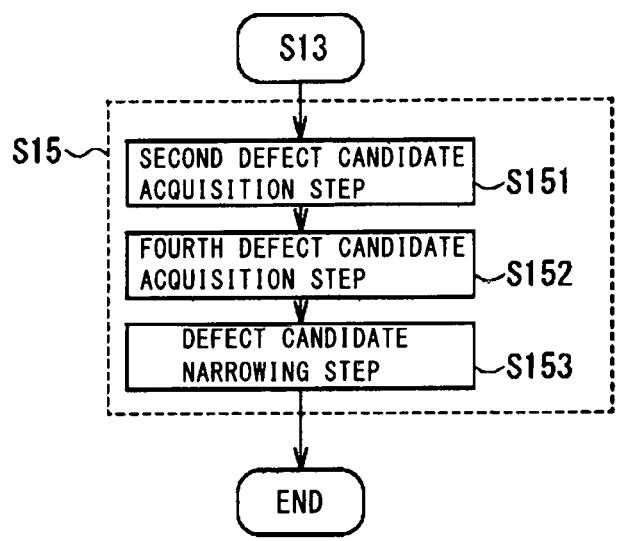
FIG. 15 illustrates a flow of a second defect acquisition step in FIG. 13.

FIG. 15 illustrates the details of the second defect acquisition step S15. The second defect acquisition step S15 includes a second defect candidate acquisition step S151, a fourth defect candidate acquisition step S152, and a defect candidate narrowing step S153.

Figure 16:
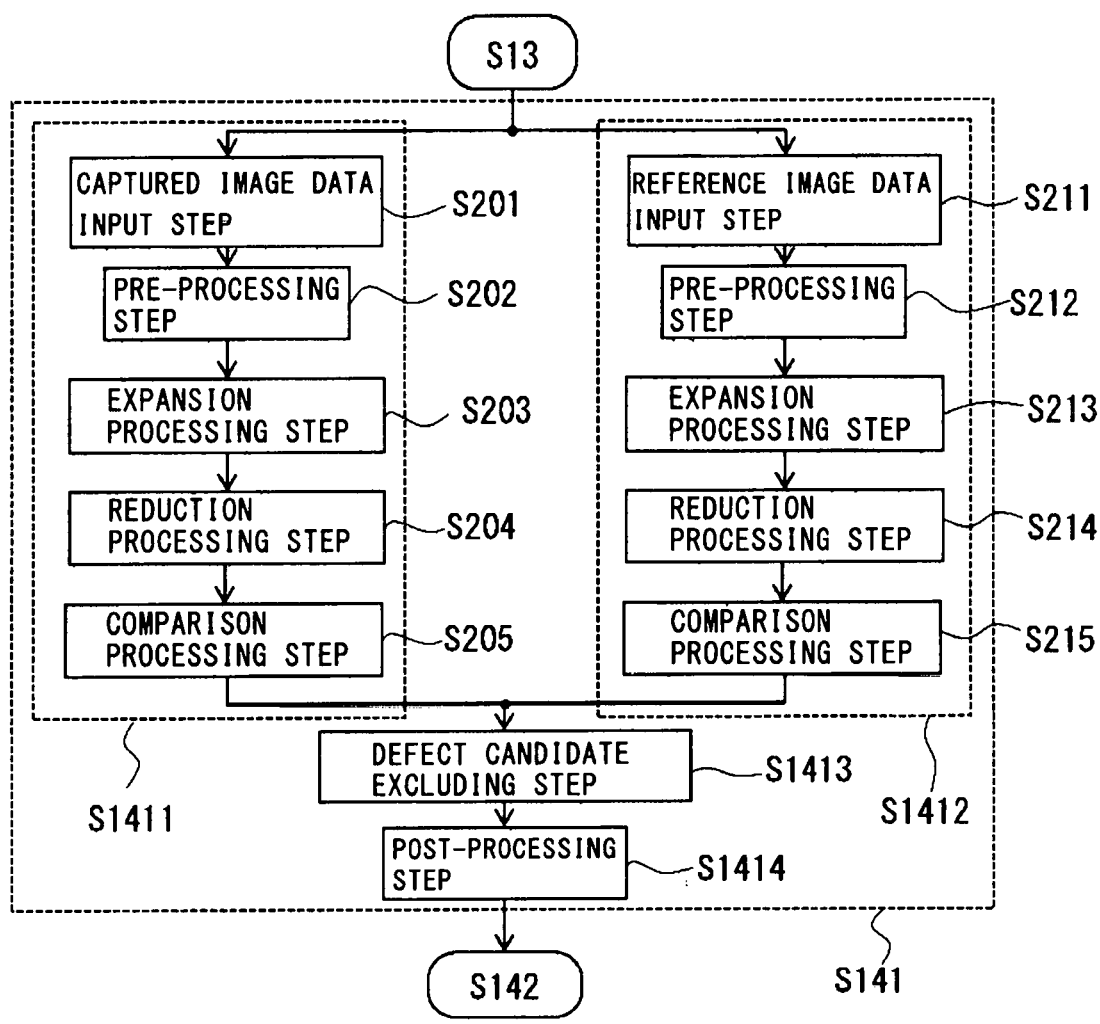
FIG. 16 illustrates a flow of a first defect candidate acquisition step in FIG. 14.

FIG. 16 illustrates the details of the first defect candidate acquisition step S141. The first defect candidate acquisition step S141 includes a first defect candidate region detection step S1411 of detecting first defect candidate regions, a first mask region detection step S1412 of detecting first mask regions, a defect candidate excluding step S1413 of excluding those of the first defect candidate regions that overlap by a prescribed criterion or more with the first mask regions from first defect candidates, and a post-processing step S1414.

Figure 17:
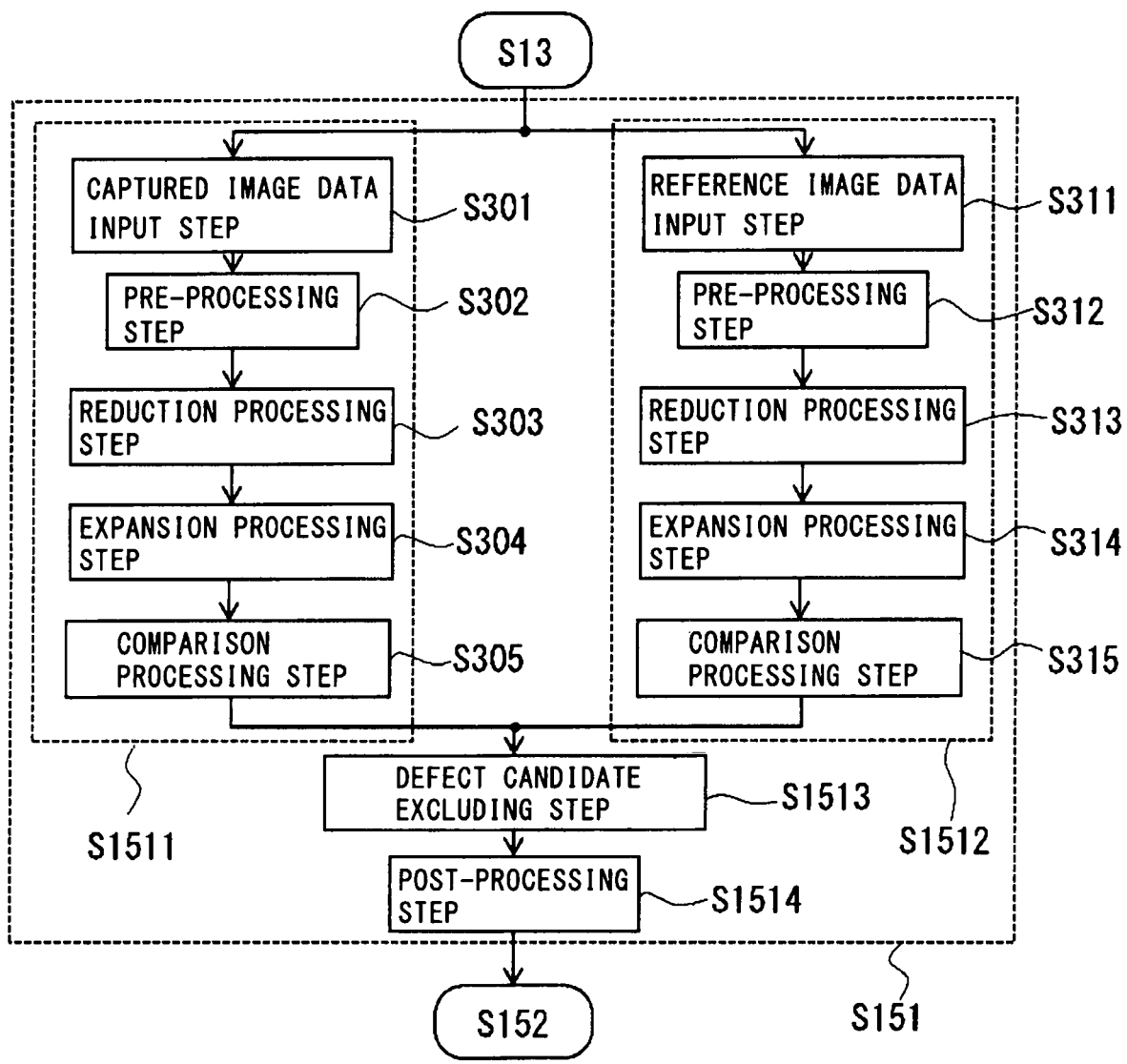
FIG. 17 illustrates a flow of a second defect candidate acquisition step in FIG. 15.

FIG. 17 illustrates the details of the second defect candidate acquisition step S151. The second defect candidate acquisition step S151 includes a second defect candidate region detection step S1511 of detecting second defect candidate regions, a second mask region detection step S1512 of detecting second mask regions, a defect candidate excluding step S1513 of excluding those of the second defect candidate regions that overlap by a prescribed criterion or more with the second mask regions from second defect candidates, and a post-processing step S1514.

Hereinafter, the first defect acquisition step S14 will be described with appropriate reference to FIGS. 5 to 20.

When the first defect acquisition step S14 is started, the first defect candidate acquisition step S141 is first executed. In the first defect candidate acquisition step S141, first, the first defect acquisition part 521 selects one captured image and selects a reference image corresponding to that captured image. As illustrated in FIG. 6, in the first defect candidate acquisition part 541, the captured image data 911 of the captured image is input to one filtering part 542 (captured image data input step S201), and the reference image data 912 of the reference image is input to the other filtering part 542 (reference image data input step S211).

Refer to FIG. 16. Next, the filtering parts 542 and the pre-alignment part 543 execute pre-processing steps S202 and S212 of performing filtering processing and pre-alignment processing on the captured image and the reference image. The two filtering parts 542 perform filtering processing for reducing noise such as median filtering or Gaussian filtering respectively on the captured image and the reference image. The captured image and the reference image that have undergone the filtering processing are output to the pre-alignment part 543. The pre-alignment part 543 specifies the amounts of positional and angular displacements of the reference image relative to the captured image through pattern matching using a predetermined pattern. Then, the reference image is moved in parallel and rotated relative to the captured image by the amounts of positional and angular displacements between the two images, so that the position and angle of the reference image are approximately aligned with those of the captured image. In this way, the two images are pre-aligned.

Figure 18:
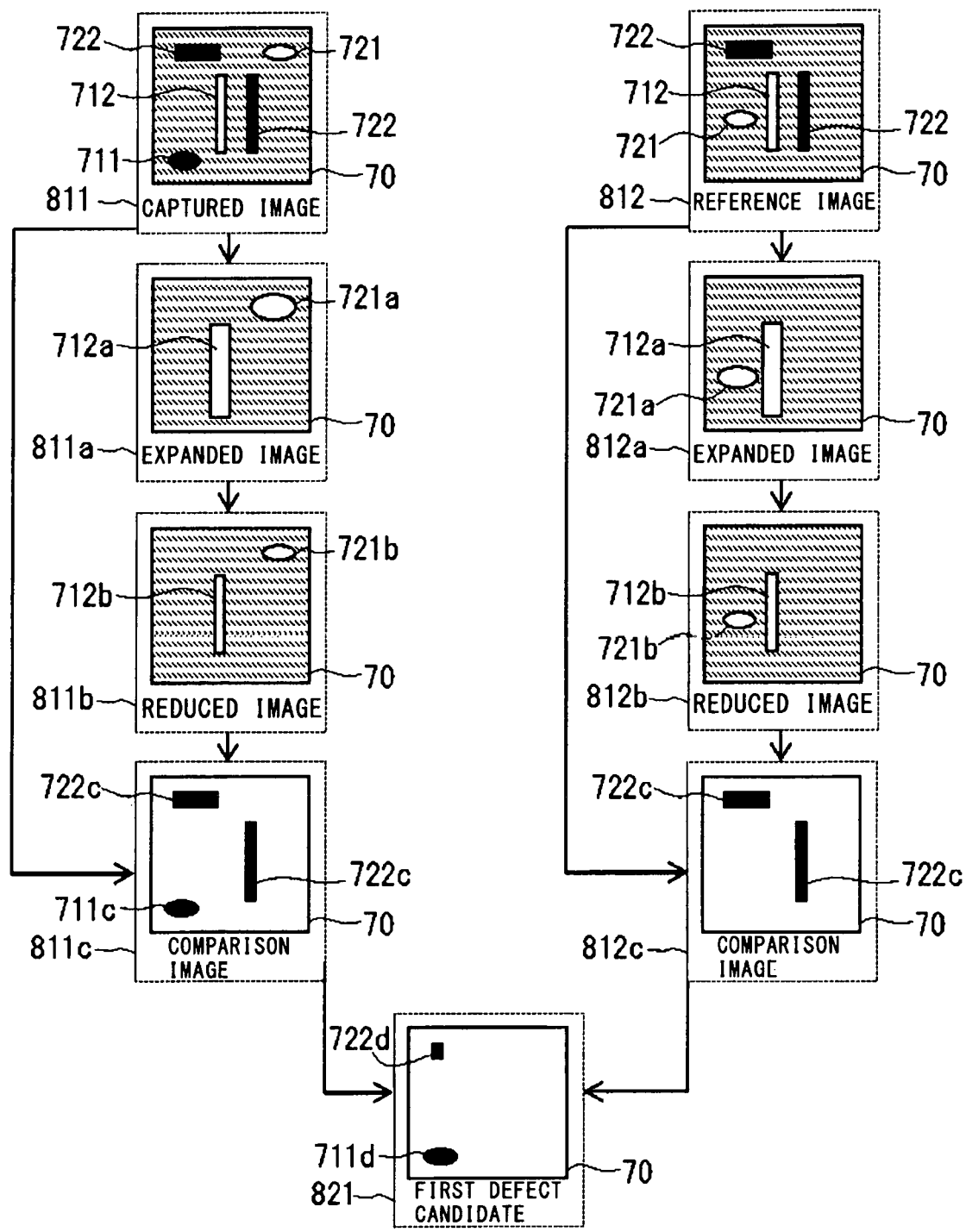
FIG. 18 illustrates an example of images for describing the content of processing in FIG. 16.

Refer to FIG. 18. FIG. 18 illustrates an example of images that indicate the content of processing in the first defect candidate acquisition step S141. A captured image that has been input in the captured image data input step S201 and has undergone the pre-processing step S202 is illustrated as a captured image 811. Also, a reference image that has been input in the reference image data input step S211 and has undergone the pre-processing step S212 is illustrated as a reference image 812. A region of the surface of the object 9 that is to be inspected and that appears in the captured image 811 and the reference image 812 is referred to as a "target region 70" and indicated by a rectangle in the captured image 811 and the reference image 812. The image capturing parts 3 and the target regions 70 are in one-to-one correspondence, and each image capturing part 3 always acquires an image of the same target region 70.

In the target region 70 of the captured image 811, a first defect 711 that appears darker than the surroundings and a second defect 721 that appears lighter than the surroundings can be recognized. These are, for example, dents or scratches. The target region 70 of the captured image 811 includes pattern portions 712 and 722. The pattern portion 712 is a depression or a projection that appears lighter than the surroundings, and the pattern portions 722 are depressions or projections that appear darker than the surroundings. These pattern portions 712 and 722 are derived from the original shape of the object 9 and are not defects.

In the target region 70 of the reference image 812, a second defect 721 that appears lighter than the surroundings can be recognized. Ordinarily, reference images are ideally acquired by extracting an object 9 with no defects, but even an object 9 that is extracted for reference images may include defects. The target region 70 of the reference image 812 includes pattern portions 712 and 722 at the same positions as in the captured image 811.

Note that the captured image 811 and the reference image 812 illustrated in FIG. 18 express first defects, second defects, and pattern portions and so on in an exaggerated manner for the purpose of description, and real defects and the like may be expressed as smaller pixels. Although the distinction between the defects and the pattern portions in the captured image 811 and the reference image 812 is mentioned for the sake of convenience, a distinction in the actual image whether a region that appears dark is a first defect or a pattern portion or whether a portion that appears light is a second defect or a pattern portion is only determined for the first time through processing described later. Thus, the distinction between defects and pattern portions is uncertain at the stage of the captured image 811 and the reference image 812.

Refer to FIG. 16. Next, the expansion processing part 544 executes expansion processing steps S203 and S213 of performing expansion processing on the captured image and the reference image that have been pre-aligned.

As illustrated in FIG. 6, in the first defect candidate acquisition part 541, the captured image data 911 and the reference image data 912 are input from the pre-alignment part 543 to the expansion processing part 544, and expansion processing is performed on the captured image and the reference image. The expansion processing as used herein refers to processing for expanding light regions in a multilevel image. The expansion processing uses a commonly known maximum value filter. The maximum value filter is a filter that extracts a pixel having a maximum pixel value from among pixels within a kernel size centered on the pixel of interest and changes the pixel value of the pixel of interest into the maximum pixel value. By passing the images through the maximum value filter, each one pixel with a high pixel value (i.e., light pixel) is expanded to 3 by 3 pixels.

In this way, an expanded image 811a and an expanded image 812a in FIG. 18 are generated. The expanded image 811a and the expanded image 812a are multilevel images. In the expanded image 811a and the expanded image 812a, second defects 721a and a pattern portion 712a that are light regions can be recognized as having been expanded, whereas small dark regions disappear.

Note that the kernel size of the maximum value filter for the implementation of the present invention is not limited to 3 by 3 pixels, and various other sizes may be employed.

Refer to FIG. 16. Next, the reduction processing part 545 executes reduction processing steps S204 and S214 of performing reduction processing on the captured image and the reference image that have undergone the expansion processing.

As illustrated in FIG. 6, data of the captured image and the reference image that have undergone the expansion processing is input to the reduction processing part 545, and reduction processing is performed on the captured image and the reference image. The reduction processing as used herein refers to processing for reducing light regions in a multilevel image. The reduction processing uses, for example, a minimum value filter of the same size as the maximum value filter used in the expansion processing and restores the light regions to almost their original sizes. The minimum value filter is a filter that extracts a pixel having a minimum pixel value from among pixels within a kernel size centered on the pixel of interest and changes the pixel value of the pixel of interest into the minimum pixel value.

In this way, a reduced image 811b and a reduced image 812b illustrated in FIG. 18 are generated. The reduced image 811b and the reduced image 812b are multilevel images. In the reduced image 811b and the reduced image 812b, second defects 721b and a pattern portion 712b that are light regions can be recognized as having been restored to almost their original sizes. Through the expansion processing and the reduction processing, large dark regions in the original captured image and the original reference image are maintained in almost their original states, and small dark regions disappear. In the example of images in FIG. 18, the dark regions are all caused to disappear by the expansion processing.

Refer to FIG. 16. Next, the comparator 546 executes comparison processing steps S205 and S215 of performing comparison processing on the captured image and the reference image that have undergone the reduction processing.

As illustrated in FIG. 6, data of the captured image and the reference image that have undergone the reduction processing is input to the comparator 546. The comparator 546 first generates a comparison image on the basis of at least one of the difference and ratio between the captured image and the reduced image obtained by performing the expansion and reduction processing on the captured image (comparison processing step S205), and in parallel with this, generates a comparison image on the basis of at least one of the difference and ratio between the reference image and the reduced image obtained by performing the expansion and reduction processing on the reference image (comparison processing step S215).

The comparison processing step S205 generates a comparison image on the basis of at least one of the difference and ratio between the captured image and the reduced image obtained by performing the expansion and reduction processing on the captured image. In the defect inspection apparatus 1 according to the present invention, whether the comparison is based on the difference or the ratio is determined on the basis of a parameter determined in advance by the program 80 or a parameter designated by the user via the input part 126. Also, various types of predetermined values, reference values, and threshold values used in the defect inspection device 1 according to the present invention are determined on the basis of parameters determined in advance by the program 80 or parameters designated by the user via the input part 126. Hereinafter, the generation of a comparison image based on the difference and the generation of a comparison image based on the ratio will be described.

As one specific example of the comparison processing step S205, a comparison image is acquired by a difference (e.g., subtraction processing). Specifically, a difference image that indicates a difference between the captured image and the reduced image, which is obtained by performing the expansion and reduction processing on the captured image, is acquired by subtracting the values of pixels in a region of the reduced image that overlap with the captured image from the values of pixels in the captured image. Then, a comparison image is acquired by extracting, in the difference image, regions where the absolute values of pixels are greater than a predetermined threshold value as first defect candidate regions.

In the present embodiment, in the difference image, the values of pixels whose absolute values are less than or equal to the predetermined threshold value are set to "0," and regions where the values of pixels are greater than zero are extracted as first defect candidate regions. Note that the method of extracting the first defect candidate regions according to the present invention is not limited to this example, and the first defect candidate regions may be extracted by executing binarization processing using a predetermined threshold value on the difference image.

In general terms, in the comparison processing step S205, in the captured image, regions whose lightness is lower than in the reduced image obtained by performing the expansion and reduction processing on the captured image and whose absolute values of the differences in lightness are greater than or equal to a first reference value are expressed as first defect candidate regions in the comparison image. The first reference value is a positive value. In yet other words, in the captured image, regions whose lightness is lower by a predetermined value than in the reduced image obtained by performing the expansion and reduction processing on the captured image are expressed as first defect candidate regions in the comparison image. In the case of a monochrome image, pixel values may be regarded as lightness, and in the case of a color image, values obtained by performing a predetermined computation on the values of pixels of each color component are treated as lightness.

As another specific example of the comparison processing step S205, the first defect candidate regions may be obtained from the ratio between the value of each pixel in the captured image and the value of the corresponding pixel in the reduced image obtained by performing the expansion and reduction processing on the captured image. Specifically, the values of pixels in a ratio image is obtained by dividing the value of each pixel in the reduced image obtained by performing the expansion and reduction processing on the captured image by the value of the corresponding pixel in the captured image. The first reference value greater than one is prepared in advance, and in the ratio image, regions each composed of pixels having values greater than or equal to the first reference value are extracted as first defect candidate regions, and a comparison image including the first defect candidate regions is acquired.

The value of pixels in the ratio image may, of course, be obtained by dividing the value of each pixel in the captured image by the value of the corresponding pixel in the reduced image obtained by performing the expansion and reduction processing on the captured image. In this case, in the ratio image, regions each composed of pixels having values less than or equal to a first reference value smaller than one are extracted as first defect candidate regions, and a comparison image including the first defect candidate regions is acquired.

The first reference value does not necessarily have to be a constant. The first reference value may be a function of the lightness or pixel values of the captured image. The first reference value may be determined using the difference and ratio in the lightness or pixel values of the captured image, or may be determined using other computations. The fact that the first reference value may be determined in various ways applies also to second, third, and fourth reference values, which will be described later. The first to fourth reference values do not necessarily have to be the same value, and may be calculated by different methods. In general terms, in the captured image, regions whose lightness is lower than the lightness of the reference image and lower than a value that satisfies a predetermined condition are acquired as first defect candidate regions. The "predetermined condition" may be set individually for each captured image. Also, a plurality of "predetermined conditions" may be used for one captured image. For example, the first reference value may be set such that defect candidate regions are unlikely to be detected at positions at which pixel values tend to change for every image capture, such as edges in the captured image. The above description applies also to the extraction of second defect candidate regions, third defect candidate regions, and fourth defect candidate regions, which will be described below.

The comparison processing step S215 generates a comparison image on the basis of at least one of the difference and ratio between the reference image and the reduced image obtained by performing the expansion and reduction processing on the reference image. In order to acquire a difference image or a ratio image, the same processing as performed in the comparison processing step S205 for the captured image is performed. In the comparison processing step S215, instead of first defect candidate regions, first mask regions are extracted from the reference image through the same processing as performed in the comparison processing step S205.

As one specific example of the comparison processing step S215, a comparison image is acquired by a difference (e.g., subtraction processing). Specifically, a difference image that indicates a difference between the reference image and the reduced image obtained by performing the expansion and reduction processing on the reference image is acquired by subtracting the values of pixels in a region of the reduced image that overlap with the reference image from the values of pixels in the reference image. Then, a comparison image is acquired by extracting, in the difference image, regions where the absolute values of pixels are greater than a predetermined threshold value as first mask regions.

As another specific example of the comparison processing step S215, the first mask regions may be obtained from the ratio between the value of each pixel in the reference image and the value of the corresponding pixel in the reduced image obtained by performing the expansion and reduction processing on the reference image. Specifically, the values of pixels in a ratio image are obtained by dividing the value of each pixel in the reduced image obtained by performing the expansion and reduction processing on the reference image by the value of the corresponding pixel in the reference image. A first reference value greater than one is prepared in advance, and in the ratio image, regions each composed of pixels having values greater than or equal to the first reference value are extracted as first mask regions, and a comparison image including the first mask regions is acquired.

At this time, the predetermined threshold value and the first reference value used in the comparison processing step S205 may be the same as or different from the predetermined threshold value and the first reference value used in the comparison processing step S215. If the same values are used, processing can be communalized, and this contributes to a reduction in processing memory and a reduction in processing time.

Through the processing described above, a comparison image 811c and a comparison image 812c illustrated in FIG. 18 are acquired. In the comparison image 811c, first defect candidate regions 711c and 722c are extracted as regions that are darker than in the captured image 811. Note that 711c corresponds to a first defect (true defect) and 722c corresponds to a pattern portion (false defect). In the comparison image 812c, first mask regions 722c are extracted as regions that are darker than in the reference image 812. Note that 722c corresponds to a pattern portion (false defect).

The captured image data input step S201, the pre-processing step S202, the expansion processing step S203, the reduction processing step S204, and the comparison processing step S205 described above constitute the first defect candidate region detection step S1411 according to the present embodiment. Note that the pre-processing step S202 can be omitted depending on the state of the captured image or inspection conditions.

Also, the reference image data input step S211, the pre-processing step S212, the expansion processing step S213, the reduction processing step S214, and the comparison processing step S215 described above constitute the first mask region detection step S1412 according to the present embodiment. Note that the pre-processing step S212 can be omitted depending on the state of the reference image or inspection conditions.

Refer to FIG. 16. Next, the comparator 546 executes the defect candidate excluding step S1413 of performing defect candidate excluding processing on the comparison images based on the captured image.

When the defect candidate excluding step S1413 is started, first, the comparator 546 executes thickening processing for thickening the first mask regions. Specifically, expansion processing using a maximum value filter is performed as the thickening processing on the comparison image 812c in the same manner as in the expansion processing step S213.

Note that the thickening processing performed for the implementation of the present invention is not limited to thickening processing using a maximum value filter, and various types of thickening processing may be employed.

Here, allowable difference may exist between the object appearing in the reference image and the object appearing in the captured image. Also, misalignment may occur between the posture of the object at the time of capturing the reference image and the posture of the object at the time of capturing the captured image. Accordingly, as will be described later, merely excluding regions of overlap between the first mask regions and the first defect candidate regions result in that, among the first defect candidate regions, regions (i.e., pattern portions) that are not defects fail to favorably overlap with the first mask regions, and in the misaligned portions, regions that are not defects remain as-is as the first defect candidate regions. In view of this, thickening processing is performed on the first mask regions in order to reduce non-overlapping portions between the first defect candidate regions and the first mask regions due to misalignment. This further suppresses over-detection.

Then, the defect candidate excluding step S1413 executes defect candidate excluding processing for generating a first defect candidate image by excluding some regions of the first defect candidate regions in the comparison image based on the captured image from first defect candidates on the basis of the first mask regions. More specifically, the first defect candidate image is generated by excluding, among the first defect candidate regions in the comparison image generated based on the captured image by the comparator 546, those that overlap by a prescribed criterion or more with the first mask regions in the comparison image based on the reference image from first defect candidates.

Here, a method of obtaining a difference or a sum between each pixel in the comparison image based on the captured image and each pixel in the comparison image based on the reference image and comparing the difference or the sum with a predetermined threshold value so as to extract first defect candidate regions is used as a method of evaluating overlaps between the first defect candidate regions and the first mask regions. Which of the extraction method using the difference and the extraction method using the sum is to be used is determined on the basis of either a parameter determined in advance by the program 80 or a parameter designated by the user via the input part 126.

In the case where the first defect candidate image is acquired on the basis of the difference, specifically, the value of each pixel in the comparison image based on the reference image is subtracted from the value of the pixel at the corresponding position in the comparison image based on the captured image so as to acquire a difference image that indicates a difference between the two images. Then, the first defect candidate image is acquired by leaving, in the difference image, regions where the values of pixels are greater than a predetermined threshold value as first defect candidates while setting the other regions to "0."

In the case where the first defect candidate image is acquired on the basis of the sum, specifically, the value of each pixel in the comparison image based on the captured image and the value of the pixel at the corresponding position in the comparison image based on the reference image are added so as to acquire a sum image that indicates the sum of the two images. Then, the first defect candidate image is acquired by setting, in the sum image, regions where the values of pixels are greater than a predetermined threshold value to a pixel value of "0" so as to exclude these regions as regions of overlap between the first mask regions and the first defect candidate regions while leaving the first defect candidate regions that do not overlap with the first mask regions.

Note that the implementation of the present invention is not limited to this example. The first defect candidate image may be acquired by performing binarization processing on the comparison image based on the captured image and the comparison image based on the reference image so that each pixel having a pixel value greater than or equal to a predetermined threshold value is set to "1" and each pixel having a pixel value less than the threshold value is to "0", then performing processing for inverting the pixel values "1" and "0" on the comparison image based on the reference image, obtaining a logical AND of the pixel value of each pixel in the comparison image based on the captured image and the pixel value of the corresponding pixel in the inverted image of the comparison image based on the reference image, and determining regions where the pixel values are "1" as first defect candidate regions. In this case, binarization processing performed by the binarization part 547 can be omitted from the post-processing step S1414, which will be described later.

Although in the present embodiment, the thickening processing is performed in the defect candidate excluding step S1413, the implementation of the present invention is not limited to this example. The thickening processing may be omitted, and only the defect candidate excluding processing may be executed in the defect candidate excluding step S1413.

Refer to FIG. 16. Next, the binarization part 547 and the area filtering part 548 execute the post-processing step S1414 of performing post-processing on the first defect candidate image.

As illustrated in FIG. 6, the first defect candidate image that is output from the comparator 546 is binarized with a predetermined threshold value by the binarization part 547. In the first defect candidate image, the first defect candidate regions are expressed as multiple values, and the other regions are expressed as "0." Through the binarization processing performed by the binarization part 547, the first defect candidate regions are set to "1," and the other regions are set to "0."

Then, the first defect candidate image that has undergone the binarization processing is input to the area filtering part 548. The area filtering part 548 deletes first defect candidate regions whose areas are smaller than a predetermined value, so that an image that indicates the remaining first defect candidate regions is acquired as a final first defect candidate image (to be precise, first defect candidate data 921 that is image data indicating first defect candidate regions).

Through the processing described above, a first defect candidate image 821 illustrated in FIG. 18 is acquired. In the first defect candidate image 821, the first defect candidate region 722c extracted in the comparison image 811c is excluded by obtaining a difference from the comparison image 812c. Accordingly, it is possible to suppress the spread of misinformation due to the pattern portion 722 that is essentially not a defect. However, in the example of images in FIG. 18, part of the first defect candidate region 722c could not be excluded by the first mask regions due to allowable difference of the object 9 between the captured image 811 and the reference image 812, and remains as a first defect candidate region 722d in the first defect candidate image 821.

The multiple captured images acquired by the image capturing parts 3 are sequentially selected as an object to be processed, so that the same number of pieces of first defect candidate data 921 as the number of captured images is acquired.

Refer to FIG. 14. Next, the third defect candidate acquisition part 551 executes the third defect candidate acquisition step S142.

As illustrated in FIG. 7, when the third defect candidate acquisition step S142 is started, first, one captured image selected in the first defect candidate acquisition step S141 and a reference image corresponding to that captured image are selected. Then, in the third defect candidate acquisition part 551, the captured image data 911 of the captured image is input to one filtering part 552, and the reference image data 912 of the reference image is input to the other filtering part 552.

Next, the filtering parts 542 and the pre-alignment part 543 respectively perform filtering processing and pre-alignment processing on the captured image and the reference image. These processing steps are the same as the pre-processing steps S202 and S212 of the first defect candidate acquisition step S141, and therefore description thereof has been omitted.

Then, the shifting comparator 554 performs shifting comparison processing using the captured image and the reference image that have undergone the pre-processing, and the binarization part 555 performs binarization processing on the images that have undergone the shifting comparison processing, so as to generate a third defect candidate image. The shifting comparator 554 obtains evaluation values that indicate a difference between the captured image and the reference image while moving the reference image little by little in the top, bottom, right, and left directions from the pre-aligned position. For example, a sum of the absolute values for (signed) differences of pixel values in a region of overlap between the two images is obtained as an evaluation value. Then, an image that indicates signed differences in pixel value between the two images at a position at which the evaluation value is a minimum is generated. The signed difference image is binarized with a predetermined value by the binarization part 555 so as to generate a third defect candidate image indicating third defect candidate regions.

In actuality, the signed difference image is not obtained, in order to simplify the processing. Specifically, the values of pixels in a difference image are obtained by subtracting the value of each pixel in the captured image from the value of the corresponding pixel in the reference image, and if the obtained value is negative, setting the value to "0." A positive value is prepared in advance, and in the difference image, regions each composed of pixels having values greater than or equal to the positive value are acquired as third defect candidate regions.

In general terms, in the captured image, regions whose lightness is lower than in the reference image and whose absolute values of the differences in lightness are greater than or equal to a second reference value are acquired as third defect candidate regions. The second reference value is a positive value. In yet other words, in the captured image, regions whose lightness is lower by a predetermined value than in the reference image are acquired as third defect candidate regions. In the case of a monochrome image, pixel values may be regarded as lightness, and in the case of a color image, values obtained by performing a predetermined computation on the values of pixels of each color component are treated as lightness.

The third defect candidate regions may be obtained from the ratio between the value of each pixel in the reference image and the value of the corresponding pixel in the captured image. Specifically, the values of pixels in a ratio image are obtained by dividing the value of each pixel in the reference image by the value of the corresponding pixel in the captured image. The second reference value greater than one is prepared in advance, and in the ratio image, regions each composed of pixels having values greater than or equal to the second reference value are acquired as third defect candidate regions. The values of pixels in the ratio image may, of course, be obtained by diving the value of each pixel in the captured image by the value of the corresponding pixel in the reference image. In this case, in the ratio image, regions each composed of pixels having values less than or equal to a second reference value smaller than one are acquired as third defect candidate regions.

The second reference value does not necessarily have to be a constant. The second reference value may be a function of the lightness or pixel values of the reference image and/or the captured image. The second reference value may be determined using the difference and ratio in lightness or pixel values between the reference image and the captured image, or may be determined using other computations.

Figure 19:
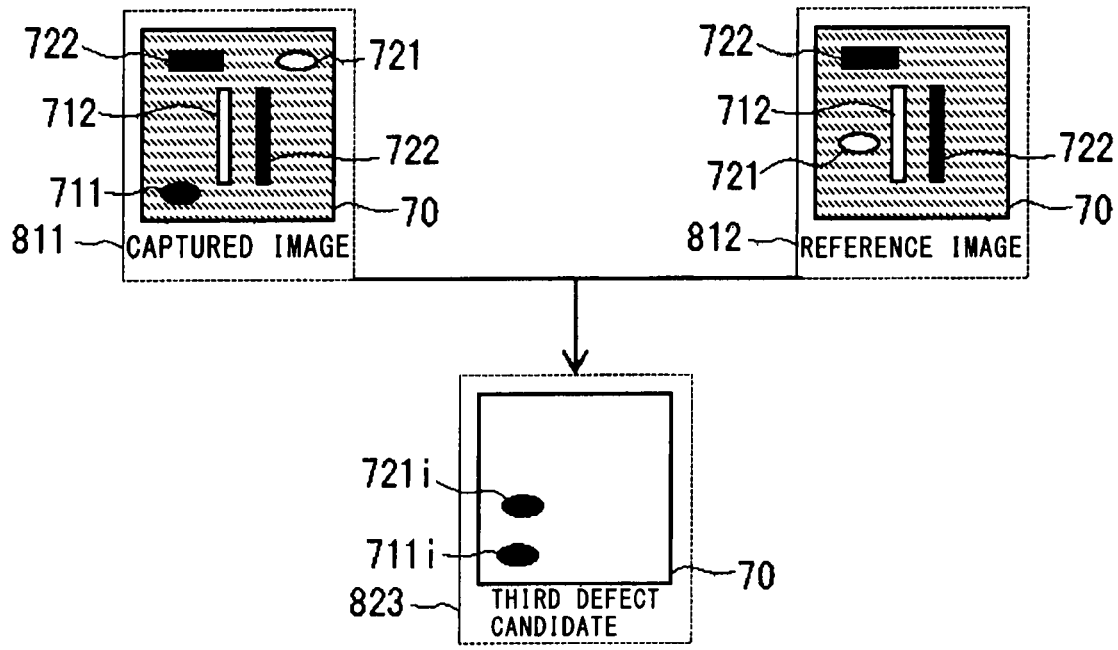
FIG. 19 illustrates an example of images for describing the content of processing in the third defect candidate acquisition step in FIG. 14.

FIG. 19 illustrates an example of images that indicate the content of processing in the third defect candidate acquisition step S142. The captured image 811 and the reference image 812 that are input are the same as the images illustrated in FIG. 18. A third defect candidate image that is generated as a result of execution of the shifting comparison processing by the shifting comparator 554 and the binarization processing by the binarization part 555 is illustrated as a third defect candidate image 823.

In the third defect candidate image 823, regions where the captured image 811 is darker than the reference image 812 are extracted as third defect candidate regions 711i and 721i by the shifting comparison processing. Out of these, the third defect candidate region 711i is a true defect that corresponds to a first defect 711 existing in the captured image 811, whereas the third defect candidate region 721i is a so-called false defect that does not exist in the captured image 811 but has been extracted as a region darker than in the reference image 812 by the shifting comparison processing due to the presence of a second defect 721 (i.e., defect that appears lighter than the surroundings) in the reference image 812. In this way, the shifting comparison processing may extract a defect region that is not included in the captured image as noise if the reference image includes a defect region.

Refer to FIG. 7. When the third defect candidate regions 711*i* and 721*i* have been acquired by the shifting comparison processing and the binarization processing, the area filtering part 556 deletes third defect candidate regions whose areas are smaller than a predetermined value, so that an image that indicates the remaining third defect candidate regions is acquired as a final third defect candidate image (to be precise, third defect candidate data 923 that is image data indicating third defect candidate regions).

The multiple captured images acquired by the image capturing parts 3 are sequentially selected as an object to be processed, so that the same number of pieces of third defect candidate data 923 as the number of captured images is acquired.

Refer to FIG. 14. When the first defect candidate data 921 and the third defect candidate data 923 have been acquired, then the defect candidate narrowing step S143 is executed so as to acquire the first defect data 931 on the basis of the first defect candidate data 921 and the third defect candidate data 923.

As illustrated in FIG. 8, when the defect candidate narrowing step S143 is started, the first defect candidate data 921 and the third defect candidate data 923 are input to the AND operation part 582. Here, the first defect candidate data 921 that is input to the AND operation part 582 is data generated from one captured image acquired by a prescribed first image capturing part 3 under a prescribed first illumination condition and a reference image corresponding to that captured image. The third defect candidate data 923 that is input to the same AND operation part 582 is data generated from the same captured image acquired by the first image capturing part 3 under the first illumination condition and the reference image corresponding to the captured image.

The AND operation part 583 different from the AND operation part 582 receives input of first defect candidate data 921 and third defect candidate data 923 that are generated from another captured image and a reference image corresponding to that captured image. Here, the first defect candidate data 921 that is input to the AND operation part 583 is data generated from one captured image acquired by the same first image capturing part 3 as used in the AND operation part 582 under a second illumination condition different from the condition for the AND operation part 582 and the reference image corresponding to that captured image. The third defect candidate data 923 that is input to the same AND operation part 583 is data generated from the captured image acquired by the first image capturing part 3 under the second illumination condition and the reference image corresponding to that captured image.

Then, the region selection part 584 receives input of data of AND images that are obtained from each combination of the first defect candidate data 921 and the third defect candidate data 923. In other words, each AND image is an image that is generated from a captured image acquired by the same image capturing part under a different illumination condition and the reference image. A first AND image acquired by the AND operation part 582 is generated on the basis of the images acquired by the first image capturing part 3 under the first illumination condition, and a second AND image acquired by the AND operation part 583 is generated on the basis of the images acquired by the first image capturing part 3 under the second illumination condition.

Each AND image is an image that indicates first defect regions generated from first defect candidate regions and third defect candidate regions.

Figure 20:
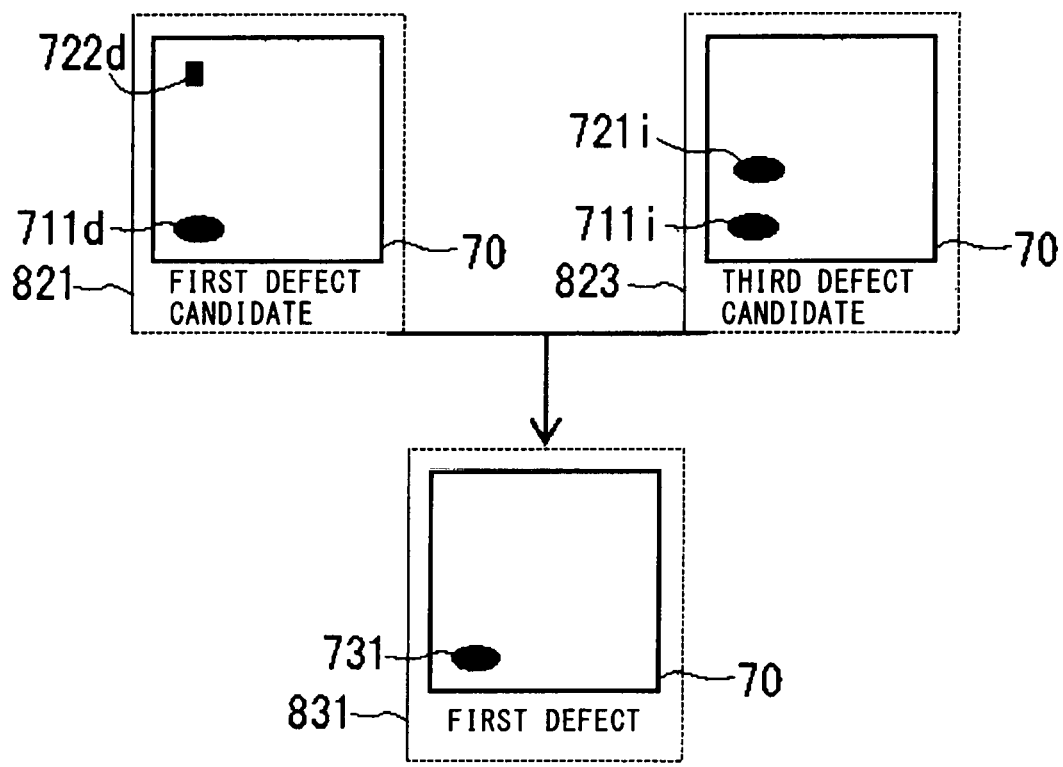
FIG. 20 illustrates an example of images for describing the content of processing in the defect candidate narrowing step in FIG. 14.

FIG. 20 illustrates an example of a first defect image 831 that indicates a first defect region 731 generated from the first defect candidate regions 711*d* and 722*d* in FIG. 18 and the third defect candidate regions 711*i* and 721*i* in FIG. 19.

The first defect candidate regions 711*d* and 722*d* are obtained by masking the first defect candidate regions 711*c* and 722*c* in the comparison image 811*c* extracted by so-called self-comparison of the captured image, with the first mask regions 722*c* in the comparison image 812*c* extracted by so-called self-comparison of the reference image. Thus, there is a low possibility of noise being detected due to defects included in the reference image 812. However, false defects (first defect candidate region 722*d* in FIG. 20) may be detected due to inaccurate alignment resulting from limited processing time.

On the other hand, the third defect candidate regions 711*i* and 721*i* are obtained from the difference image between the captured image 811 and the reference image 812 after the alignment of these images, so that the reliability of indication of the presence of defects is high. However, the third defect candidate regions may cause defects included in the reference image 812 to be detected as false defects (third defect candidate region 721*i* in FIG. 20).

In view of this, in the present embodiment, an AND image of the first defect candidate image 821 and the third defect candidate image 823 is obtained so as to acquire the first defect image 831 that indicates the more reliable first defect region 731.

In the case of overlaying a plurality of first defect images 831, the region selection part 584 maintains overlapping regions where a predetermined number or more of first defect regions overlap as first defect regions, and excludes regions where the number of first defect regions that overlap is less than the predetermined number from the first defect regions. The "overlapping region" as used herein may be a logical OR of the values of pixel in a plurality of regions that overlap, or may be a logical AND of these values of pixels. In the present embodiment, regions where the number of regions that overlap is two or more are maintained as first defect regions. The region selection part 584 acquires one first defect image that indicates narrowed first defect regions from a plurality of first defect images 831 indicating the first defect regions 731, and the first defect data 931 corresponding to this first defect image is output from the region selection part 584. Accordingly, regions that are darker than in the reference image are extracted as first defect regions from a plurality of captured images acquired in a plurality of illumination states while referencing the corresponding reference images.

The first defect data 931 that is output from the region selection part 584 is output from the defect acquisition part 52 to the storage 53 and stored in the storage 53.

The first defect acquisition step S14 of acquiring the presence of first defects in captured images is thereby completed.

In parallel with the first defect acquisition step S14, the second defect acquisition step S15 of acquiring the presence of second defects in captured images is executed. The second defects are defects that appear lighter in captured images than in reference images. The second defect acquisition step S15 differs from the first defect acquisition step S14 in that the sequence of the expansion processing step and the reduction processing step is reversed and the sequence of subtraction and division is reversed in order to detect regions where a captured image is lighter than the reference image or the other regions in the captured image. The remaining parts of the second defect acquisition step S15 are common to those of the first defect acquisition step S14, and therefore description of the common parts has appropriately been omitted.

The second defect acquisition step S15 will be described hereinafter with appropriate reference to FIGS. 9 to 23.

When the second defect acquisition step S15 is started, first, the second defect candidate acquisition step S151 is executed. In the second defect candidate acquisition step S151, first, the second defect acquisition part 522 selects one captured image and selects a reference image corresponding to that captured image. As illustrated in FIG. 9, in the second defect candidate acquisition part 561, captured image data 911 of the captured image is input to one filtering part 562 (captured image data input step S301) and reference image data 912 of the reference image is input to the other filtering part 562 (reference image data input step S311).

Refer to FIG. 17. Pre-processing steps S302 and S312 are performed in the same manner as the pre-processing steps S201 and S211 (FIG. 16). Next, the reduction processing part 564 executes reduction processing steps S303 and S313 of performing reduction processing on the captured image and the reference image that have been pre-aligned.

As illustrated in FIG. 10, in the second defect candidate acquisition part 561, the captured image data 911 and the reference image data 912 are input from the pre-alignment part 563 to the reduction processing part 564, and reduction processing is performed on the captured image and the reference image. The reduction processing as used herein refers to processing for reducing light regions in a multilevel image, and also refers to expansion processing for dark regions. This processing causes small light regions to disappear. The reduction processing uses, for example, a commonly known minimum value filter, through which each one pixel with a low pixel value (i.e., dark pixel) is expanded to 3 by 3 pixels.

Figure 21:
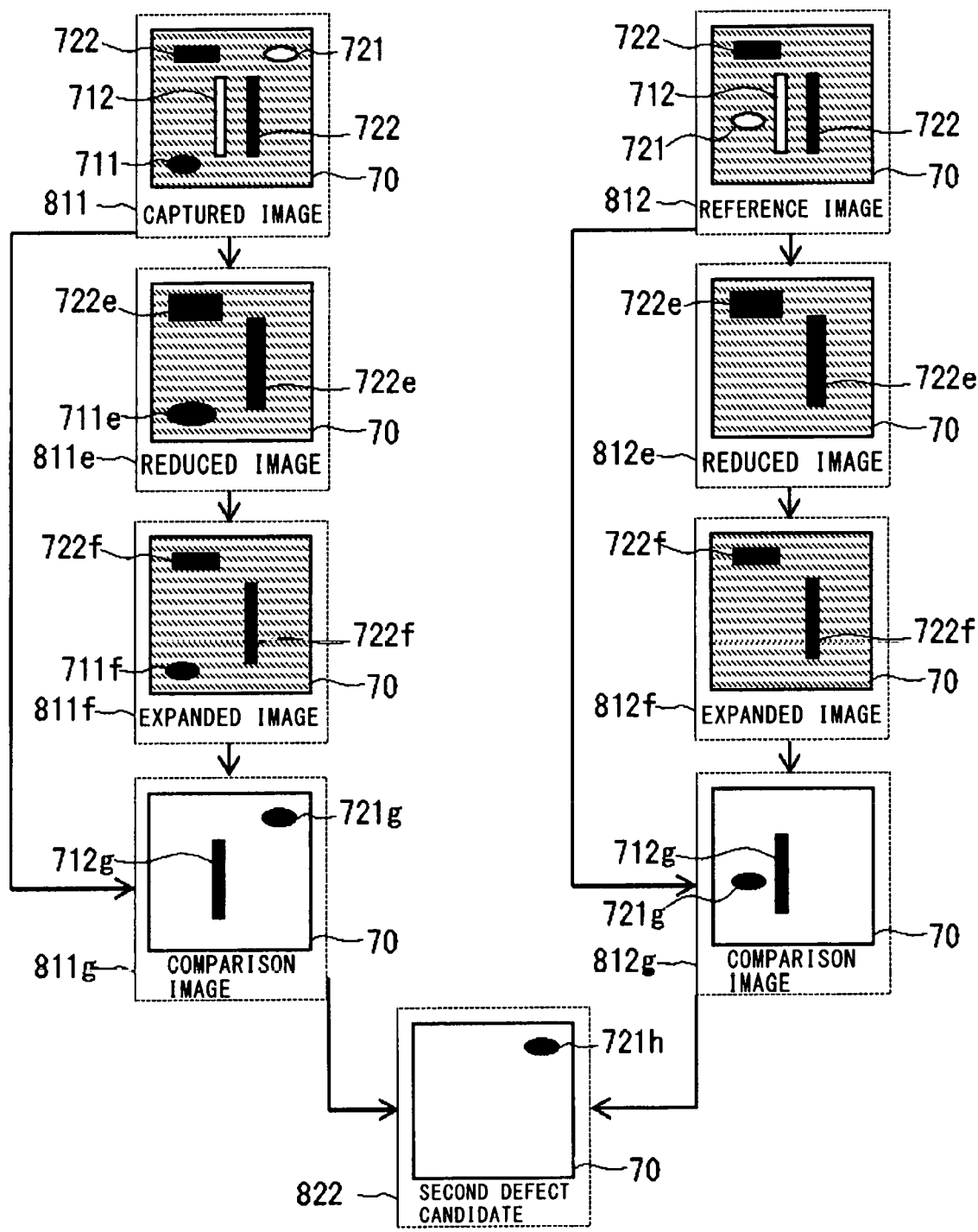
FIG. 21 illustrates an example of images for describing the content of processing in FIG. 17.

FIG. 21 illustrates an example of images that indicate the content of processing in the second defect candidate acquisition step S151, and a captured image 811 and a reference image 812 that are input are the same as those in FIG. 18.

Through the reduction processing, a reduced image 811*e* and a reduced image 812*e* in FIG. 21 are generated. In the reduced image 811*e* and the reduced image 812*e*, a first defect 711*e* and pattern portions 722*e* that are dark regions can be recognized as having been expanded, whereas small light regions disappear.

Note that the kernel size of the minimum value filter for the implementation of the present invention is not limited to 3 by 3 pixels, and various other sizes may be employed.

Refer to FIG. 17. Next, the expansion processing part 565 executes expansion processing steps S304 and S314 of performing expansion processing on the captured image and the reference image that have undergone the reduction processing.

As illustrated in FIG. 10, data of the captured image and the reference image that have undergone the reduction processing is input to the expansion processing part 565, and expansion processing is performed on the captured image and the reference image. The expansion processing as used herein refers to processing for expanding light regions in a multilevel image. The expansion processing uses, for example, a maximum value filter of the same size as the size of the minimum value filter used in the reduction processing and restores the expanded dark regions to almost their original sizes.

In this way, an expanded image 811*f* and an expanded image 812*f* illustrated in FIG. 21 are generated. In the expanded image 811*f* and the expanded image 812*f*, the first defect 711*f* and the pattern portions 722*f* that are dark regions can be recognized as having been restored to almost their original sizes. Through the reduction processing and the expansion processing, large light regions in the original captured image and the original reference image are maintained in almost their original states, and small light regions disappear. In the example of images in FIG. 21, light regions are all caused to disappear by the reduction processing.

Refer to FIG. 17. Next, the comparator 566 executes comparison processing steps S305 and S315 of performing comparison processing on the captured image and the reference image that have undergone the expansion processing.

As illustrated in FIG. 10, data of the captured image and the reference image that have undergone the expansion processing is input to the comparator 566. The comparator 566 generates a comparison image on the basis of at least one of the difference and ratio between the captured image and the expanded image obtained by performing the reduction and expansion processing on the captured image (comparison processing step S305), and in parallel with this, generates a comparison image on the basis of at least one of the difference and ratio between the reference image and the expanded image obtained by performing the reduction and expansion processing on the reference image (comparison processing step S315).

The processing performed in the comparison processing steps S305 and S315 and the processing performed in the comparison processing steps S205 and S215 are common, except that different reference values are used as threshold values and a different order of the numerator and the denominator is used when generating a comparison image on the basis of the ratio. Thus, description of common parts has appropriately been omitted.

As one specific example of the comparison processing step S305, a comparison image is acquired by the difference (e.g., subtraction processing). Specifically, a difference image that indicates a difference between the captured image and the expanded image obtained by performing the reduction and expansion processing on the captured image is acquired by subtracting the values of pixels in regions of the expanded image that overlap with the captured image from the values of pixels in the captured image. Then, a comparison image is acquired by extracting, in the difference image, regions where the absolute values of pixels are greater than a predetermined threshold value as second defect candidate regions.

In general terms, in the comparison processing step S305, in the captured image, regions whose lightness is higher than in the expanded image obtained by performing the reduction and expansion processing on the captured image and whose absolute values of differences in lightness are greater than or equal to a third reference value are expressed as second defect candidate regions in the comparison image. The third reference value is a positive value. In yet other words, in the captured image, regions whose lightness is higher by a predetermined value or more than in the expanded image obtained by performing the reduction and expansion processing on the captured image are expressed as second defect candidate regions in the comparison image. In the case of a monochrome image, pixel values may be regarded as lightness, and in the case of a color image, values obtained by performing a predetermined computation on the values of pixels of each color component are treated as lightness.

As another specific example of the comparison processing step S305, the second defect candidate regions may be obtained from the ratio between the value of each pixel in the captured image and the value of the corresponding pixel in the expanded image obtained by performing the reduction and expansion processing on the captured image. Specifically, the values of pixels in a ratio image are obtained by dividing the value of each pixel in the captured image by the value of the corresponding pixel in the expanded image obtained by performing the reduction and expansion processing on the captured image. A third reference value greater than one is prepared in advance, and in the ratio image, regions each composed of pixels having values greater than or equal to the third reference value are extracted as second defect candidate regions, and a comparison image including the second defect candidate regions is acquired.

The values of pixels in the ratio image may, of course, be obtained by dividing the value of each pixel in the expanded image obtained by performing the reduction and expansion processing on the captured image by the value of the corresponding pixel in the captured image. In this case, in the ratio image, regions each composed of pixels having values less than or equal to a third reference value smaller than one are extracted as second defect candidate regions, and a comparison image including the second defect candidate regions is acquired.

The comparison processing step S315 generates a comparison image on the basis of at least one of the difference and ratio between the reference image and the expanded image obtained by performing the reduction and expansion processing on the reference image. In order to acquire a difference image or a ratio image, the same processing as performed in the comparison processing step S305 for the captured image is performed. In the comparison processing step S315, instead of second defect candidate regions, light regions in the reference image are extracted as second mask regions through the same processing as performed in the comparison processing step S305.

As one specific example of the comparison processing step S315, a comparison image is acquired by the difference (subtraction processing, for example). Specifically, a difference image that indicates a difference between the reference image and the expanded image obtained by performing the reduction and expansion processing on the reference image is acquired by subtracting the values of pixels in regions of the expanded image that overlap with the reference image from the values of pixels in the reference image. Then, a comparison image is acquired by extracting, in the difference image, regions where the absolute values of pixels are greater than a predetermined threshold value as second mask regions.

As another specific example of the comparison processing step S315, the second mask regions may be obtained from the ratio between the value of each pixel in the reference image and the value of the corresponding pixel in the expanded image obtained by performing the reduction and expansion processing on the reference image.

Through the processing described above, a comparison image 811g and a comparison image 812g illustrated in FIG. 21 are acquired. In the comparison image 811g, second defect candidate regions 712g and 721g are extracted as regions that are lighter than in the captured image 811. In the comparison image 812g, second mask regions 712g and 721g are extracted as regions that are lighter than in the reference image 812. Note that 721g corresponds to a second defect (true defect) and 712g corresponds to a pattern portion (false defect).

The captured image data input step S301, the pre-processing step S302, the reduction processing step S303, the expansion processing step S304, and the comparison processing step S305 described above constitute the second defect candidate region detection step S1511 according to the present embodiment. Note that the pre-processing step S302 can be omitted depending on the state of the captured image and inspection conditions.

Also, the reference image data input step S311, the pre-processing step S312, the reduction processing step S313, the expansion processing step S314, and the comparison processing step S315 described above constitute the second mask region detection step S1512 according to the present embodiment. Note that the pre-processing step S312 can be omitted depending on the state of the reference image and inspection conditions.

Refer to FIG. 17. Next, the comparator 566 executes a defect candidate excluding step S1513 of performing defect candidate excluding processing on the comparison image based on the captured image.

The defect candidate excluding step S1513 generates a second defect candidate image by excluding some regions of the second defect candidate regions in the comparison image based on the captured image from second defect candidates on the basis of the second mask regions. More specifically, as in the defect candidate excluding step S1413, the second defect candidate image is generated by excluding, among the second defect candidate regions in the comparison image generated based on the captured image by the comparator 566, those that overlap by a prescribed criterion or more with the second mask regions in the comparison image based on the reference image, from second defect candidates.

Next, the binarization part 567 and the area filtering part 568 execute a post-processing step S1514 of performing post-processing on the second defect candidate image and acquire a final second defect candidate image (to be precise, second defect candidate data 922 that is image data indicating second defect candidate regions). The post-processing step S1514 is the same processing as performed in the post-processing step S1414, and therefore description thereof has been omitted.

Through the processing described above, a second defect candidate image 822 illustrated in FIG. 21 is acquired. In the second defect candidate image 822, the second defect candidate region 712g extracted in the comparison image 811g is excluded by obtaining a difference from the comparison image 812g, and only a second defect candidate region 721h remains. Accordingly, it is possible to suppress over-detection due to the pattern portion 712 that is essentially not a defect.

Also, even if the second defect 721 included in the reference image 812 remains as the second mask region 721g in the comparison image 812g, the second defect candidate image 822 is prevented from being affected thereby. The second defect candidate region 721h is extracted from among the second defect candidate regions 712g and 721g in the comparison image 811g, and thus noise (i.e., fault defect) does not occur in the second defect candidate image 822 due to the second defect 721 that occurs only in the reference image 812.

The multiple captured images acquired by the image capturing parts 3 are sequentially selected as an object to be processed, so that the same number of pieces of second defect candidate data 922 as the number of captured images is acquired.

Refer to FIG. 15. Next, the fourth defect candidate acquisition part 571 executes the fourth defect candidate acquisition step S152.

As illustrated in FIG. 11, when the fourth defect candidate acquisition step S152 is started, first, one captured image selected in the second defect candidate acquisition step S151 and the reference image corresponding to that captured image are selected. Then, in the fourth defect candidate acquisition part 571, the captured image data 911 of the captured image is input to one filtering part 572, and the reference image data 912 of the reference image is input to the other filtering part 572.

Next, the filtering parts 572 and the pre-alignment part 573 respectively perform filtering processing and pre-alignment processing on the captured image and the reference image. These processing steps are the same as the pre-processing steps S302 and S312 of the second defect candidate acquisition step S151, and therefore description thereof has been omitted.

Then, the shifting comparator 574 performs shifting comparison processing using the captured image and the reference image that have undergone the pre-processing, and the binarization part 575 performs binarization processing on the images that have undergone the shifting comparison processing so as to generate a fourth defect candidate image. The shifting comparator 574 obtains evaluation values that indicate a difference between the captured image and the reference image while moving the reference image little by little in the up, down, right, and left directions from the pre-aligned position. For example, a sum of the absolute values for (signed) differences of pixel values in a region of overlap between the two images is obtained as an evaluation value. Then, an image that indicates signed differences in pixel value between the two images at a position at which the evaluation value is a minimum is generated. The signed difference image is binarized with a predetermined value by the binarization part 575 so as to generate a fourth defect candidate image indicating fourth defect candidate regions.

In actuality, the signed difference image is not obtained, in order to simplify the processing. Specifically, the values of pixels in a difference image are obtained by subtracting the value of each pixel in the reference image from the value of the corresponding pixel in the captured image, and if the obtained value is negative, setting the value to "0." A positive value is prepared in advance, and in the difference image, regions each composed of pixels having values greater than or equal to the positive value are acquired as fourth defect candidate regions.

In general terms, in the captured image, regions whose lightness is higher than in the reference image and whose absolute values of the differences in lightness are greater than or equal to a fourth reference value are acquired as fourth defect candidate regions. The fourth reference value is a positive value. In yet other words, in the captured image, regions whose lightness is higher by a predetermined value or more than in the reference image are acquired as fourth defect candidate regions. In the case of a monochrome image, the values of pixels may be regarded as lightness, and in the case of a color image, values obtained by performing a predetermined computation on the pixels values of each color component are treated as lightness.

The fourth defect candidate regions may be obtained from the ratio between the value of each pixel in the reference image and the value of the corresponding pixel in the captured image. Specifically, the values of pixels in a ratio image are obtained by dividing the value of each pixel in the captured image by the value of the corresponding pixel in the reference image. A fourth reference value greater than one is prepared in advance, and in the ratio image, regions each composed of pixels having values greater than or equal to the fourth reference value are acquired as fourth defect candidate regions. The values of pixels in the ratio image may, of course, be obtained by dividing the value of each pixel in the reference image by the value of the corresponding pixel in the captured image. In this case, in the ratio image, regions each composed of pixels having values less than or equal to a fourth reference value smaller than one are acquired as fourth defect candidate regions.

The fourth reference value does not necessarily have to be a constant. The fourth reference value may be a function of the lightness or pixel values of the reference image and/or the captured image. The fourth reference value may be determined using the difference and ratio in lightness or pixel value between the reference image and the captured image, or may be determined using other computations.

Figure 22:
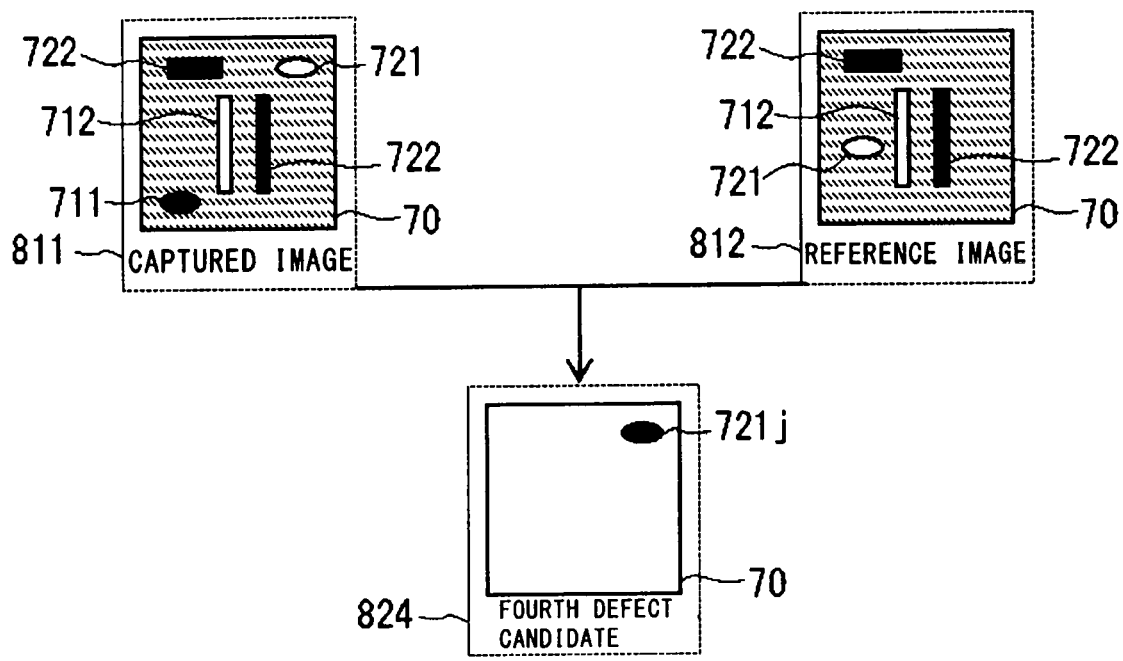
FIG. 22 illustrates an example of images for describing the content of processing in the fourth defect candidate acquisition step in FIG. 15.

FIG. 22 illustrates an example of images that indicate the content of processing in the fourth defect candidate acquisition step S152. A captured image 811 and a reference image 812 that are input are the same as the images illustrated in FIG. 21. A fourth defect candidate image generated as a result of execution of the shifting comparison processing by the shifting comparator 574 and the binarization processing by the binarization part 575 is illustrated as a fourth defect candidate image 824.

In the fourth defect candidate image 824, a region where the captured image 811 is lighter than the reference image 812 is extracted as a fourth defect candidate region 721*j* by the shifting comparison processing.

Refer to FIG. 10. When the fourth defect candidate region 721*j* has been acquired through the shifting comparison processing and the binarization processing, the area filtering part 576 deletes fourth defect candidate regions whose areas are smaller than a predetermined value, so that an image that indicates the remaining fourth defect candidate regions is acquired as a final fourth defect candidate image (to be precise, fourth defect candidate data 924 that is image data indicating fourth defect candidate regions).

The multiple captured images acquired by the image capturing parts 3 are sequentially selected as an object to be processed, so that the same number of pieces of fourth defect candidate data 924 as the number of captured images is acquired.

Refer to FIG. 15. When the second defect candidate data 922 and the fourth defect candidate data 924 have been acquired, then the defect candidate narrowing step S153 is executed so as to acquire the second defect data 932 on the basis of the second defect candidate data 922 and the fourth defect candidate data 924.

As illustrated in FIG. 12, when the defect candidate narrowing step S153 is started, the second defect candidate data 922 and the fourth defect candidate data 924 are input to the AND operation parts 592 and 593. The relationship between the second defect candidate data 922 and the fourth defect candidate data 924 that are input and the AND operation parts 592 and 593 (i.e., relationship between the image capturing parts and the illumination conditions) is the same as the relationship in the defect candidate narrowing step S143, and therefore description thereof has been omitted.

The region selection part 594 receives input of data of AND images that are obtained from each combination of the second defect candidate data 922 and the fourth defect candidate data 924.

Figure 23:
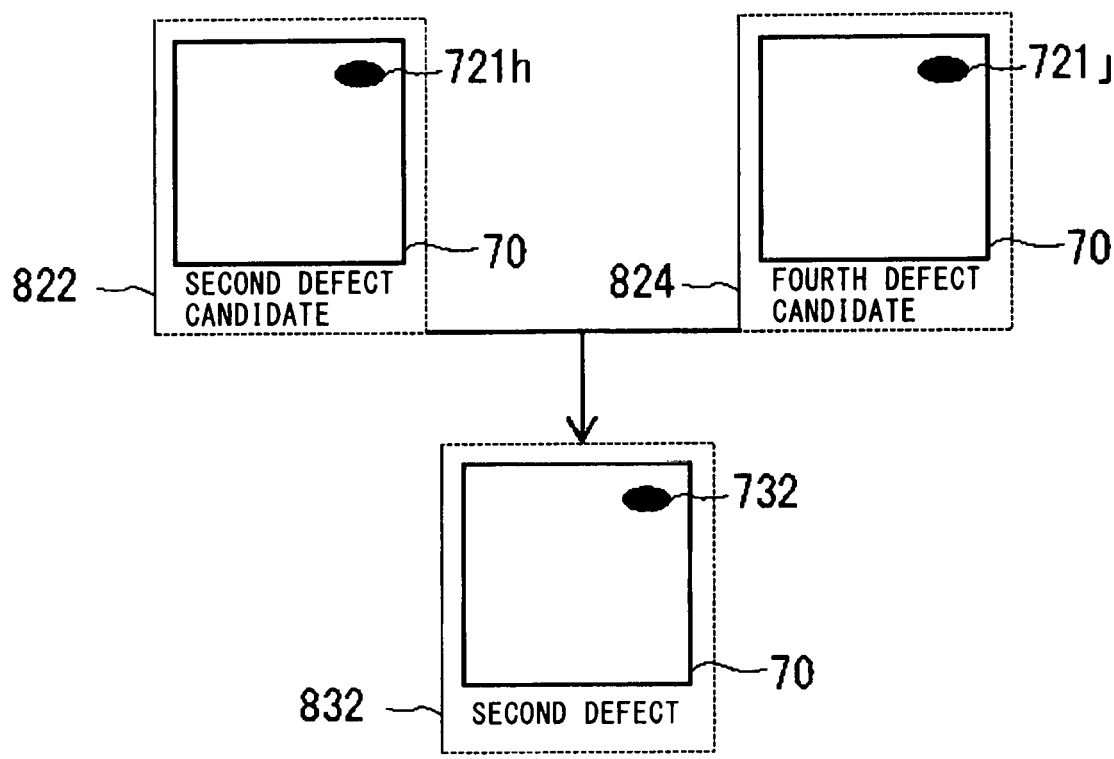
FIG. 23 illustrates an example of images for describing the content of processing in the defect candidate narrowing step in FIG. 15.

FIG. 23 illustrates an example of a second defect image 832 that indicates a second defect region 732 generated from the second defect candidate region 721h in FIG. 21 and the fourth defect candidate region 721j in FIG. 22

In the defect candidate excluding step S1513, an AND image of the second defect candidate image 822 and the fourth defect candidate image 824 is obtained so as to acquire the second defect image 832 that indicates the more reliable second defect region 732.

In the case of overlaying a plurality of second defect images 832, the region selection part 594 maintains overlapping regions where a predetermined number or more of second defect regions overlap as second defect regions, and excludes regions where the number of second defect regions that overlap is less than the predetermined number from the second defect regions. The "overlapping region" as used herein may be a logical OR of a plurality of regions that overlap, or may be a logical AND thereof. In the present embodiment, regions where the number of regions that overlap is two or more are maintained as second defect regions. The region selection part 594 acquires one second defect image that indicates narrowed second defect regions from a plurality of second defect images 832 that indicate the second defect regions 732, so that the second defect data 932 corresponding to this second defect image is output from the region selection part 594. Accordingly, regions that are lighter than in the reference image are extracted as second defect regions from a plurality of captured images acquired in a plurality of illumination states while referencing the corresponding reference images.

The second defect data 932 that is output from the region selection part 594 is output from the defect acquisition part 52 to the storage 53 and stored in the storage 53.

The second defect acquisition step S15 of acquiring the presence of second defects in captured images is thereby completed.

In the case where there is a defect in the target region 70 viewed from one image capturing part 3, the position of the defect is detected through the processing described above.

On the display of the computer 12, one captured image is displayed, and first defect regions and second defect regions are also displayed as regions colored in different colors on the target region 70. Note that the implementation of the present invention is not limited to this example, and either one of the first defect regions and the second defect regions may be displayed on the display and may be displayed switchable to the other defect regions in accordance with the user input.

A minimum number of captured images acquired by one image capturing part 3 is two, but preferably three or more. That is, the light emission part 4 can provide three or more illumination states that are different from one another, and for example, can irradiate the object 9 with light from three or more directions, and the image capturing parts 3 acquire images during the three or more illumination states under the control of the image capture controller 51. In the case where a preferable illumination state is commonly known, at least one of three or more captured images acquired on the basis of that information may be selected as a captured image to be processed. More appropriate defect detection can easily be conducted by preparing three or more captured images.

Generally, the first defect candidates and the second defect candidates in the above description can be expressed as "defect candidates," the first defect candidate regions and the second defect candidate regions can be expressed as "defect candidate regions," the first mask regions and the second mask regions can be expressed as "mask regions," and the first defect candidate image and the second defect candidate image can be expressed as "defect candidate images."

In the above description, at least one of the first defect candidate acquisition part 541 and the second defect candidate acquisition part 561 corresponds to a "self-comparison defect candidate acquisition part" according to the present invention. In the above description, if the first defect candidate acquisition part 541 corresponds to the "self-comparison defect candidate acquisition part" according to the present invention, the third defect candidate acquisition part 551 corresponds to an "other-image-related comparison defect candidate acquisition part" according to the present invention, and the defect candidate narrowing part 581 corresponds to a "defect candidate narrowing part" according to the present invention. In the above description, if the second defect candidate acquisition part 561 corresponds to the "self-comparison defect candidate acquisition part" according to the present invention, the fourth defect candidate acquisition part 571 corresponds to the "other-image-related comparison defect candidate acquisition part" according to the present invention, and the defect candidate narrowing part 591 corresponds to the "defect candidate narrowing part" according to the present invention.

In the above description, the image capturing step S13 corresponds to an "image capturing step" according to the present invention, and at least one of the first defect candidate acquisition step S141 and the second defect candidate acquisition step S151 corresponds to a "self-comparison defect candidate acquisition step" according to the present invention. In the above description, if the first defect candidate acquisition step S141 corresponds to the "self-comparison defect candidate acquisition step" according to the present invention, the third defect candidate acquisition step 142 corresponds to an "other-image-related comparison defect candidate acquisition step" according to the present invention, and the defect candidate narrowing step S143 corresponds to a "defect candidate narrowing step" according to the present invention. In the above description, if the second defect candidate acquisition step S151 corresponds to the "self-comparison defect candidate acquisition part" according to the present invention, the fourth defect candidate acquisition step S152 corresponds to the "other-image-related comparison defect candidate acquisition step" according to the present invention, and the defect candidate narrowing step S153 corresponds to the "defect candidate narrowing step" according to the present invention.

In the defect detection method, the third defect candidate acquisition step S142 and the defect candidate narrowing step S143 in the first defect acquisition step S14 may be omitted, and the first defect candidate regions acquired in the first defect candidate acquisition step S141 may be acquired as first defect regions. Even in this case, over-detection can be suppressed because, among the first defect candidate regions in the first defect candidate acquisition step S141, those that overlap by a prescribed criterion or more with the first mask regions are excluded from first defect candidates and then the presence of defects in the captured image is acquired on the basis of the first defect candidate regions.

Similarly, the fourth defect candidate acquisition step S152 and the defect candidate narrowing step S153 in the second defect acquisition step S15 may be omitted, and the second defect candidate regions acquired in the second defect candidate acquisition step S151 may be acquired as second defect regions. Even in this case, over-detection can be suppressed because, among the second defect candidate regions in the second defect candidate acquisition step S151, those that overlap by a prescribed criterion or more with the second mask regions are excluded from second defect candidates and then the presence of defects in the captured image is acquired on the basis of the second defect candidate regions.

In this case, the defect detection device 1 may acquire the first defect candidate data 921 output from the first defect candidate acquisition part 541 as the first defect data 931 and acquire the second defect candidate data 922 output from the second defect candidate acquisition part 561 as the second defect data 932, without particularly including the third defect candidate acquisition part 551, the fourth defect candidate acquisition part 571, and the defect candidate narrowing parts 581 and 591.

In the defect detection method, the first mask region detection step S1412 and the defect candidate excluding step S1413 in the first defect acquisition step S14 may be omitted, and the first defect candidate regions acquired in the first defect candidate region detection step S1411 may be acquired as first defect candidate regions. That is, the first defect candidate data 921 may be acquired without narrowing down the first defect candidate regions by the first mask regions. Even in this case, over-detection can be suppressed because, among the first defect candidate regions detected in the first defect candidate acquisition step S141, regions that overlap by a prescribed criterion or more with the third defect candidate regions are maintained as the first defect candidate regions, ° and the presence of defects in the captured image is acquired on the basis of the first defect candidate regions.

Similarly, the second mask region detection step S1512 and the defect candidate excluding step S1513 in the second defect acquisition step S15 may be omitted, and the second defect candidate regions acquired in the second defect candidate region detection step S1511 may be acquired as second defect regions. That is, the second defect candidate data 922 may be acquired without narrowing down the second defect candidate regions by the second mask regions. Even in this case, over-detection can be suppressed because, among the second defect candidate regions in the second defect candidate acquisition step S151, those that overlap by a prescribed criterion or more with a fourth defect candidate regions are maintained as the second defect candidate regions, and the presence of defects in the captured image is acquired on the basis of the second defect candidate regions.

Figure 24:
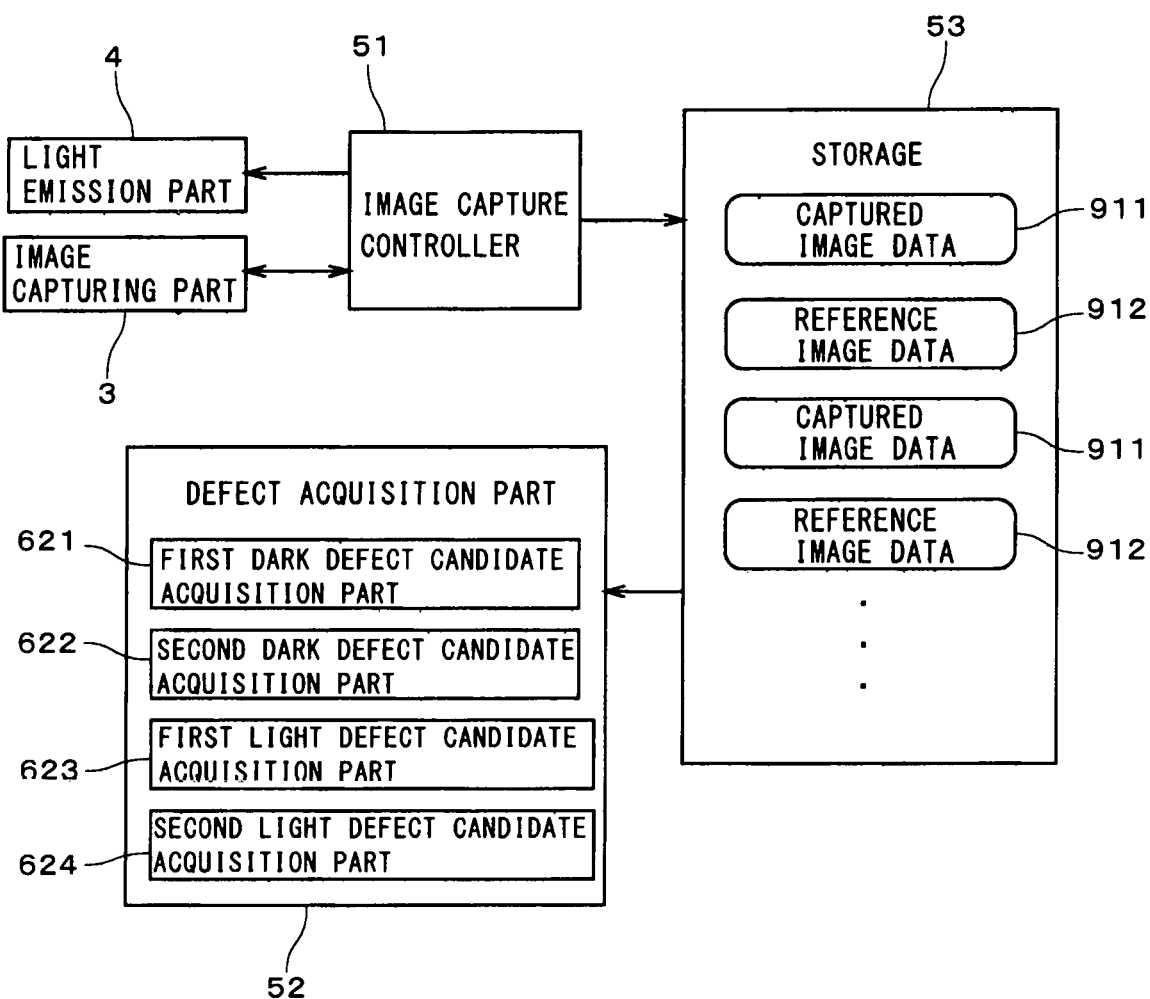
FIG. 24 is a block diagram illustrating a functional configuration implemented by the computer.

FIG. 24 illustrates another example of functions implemented by the computer 12 executing arithmetic processing in accordance with the program 80. In FIG. 24, the image capture controller 51, the defect acquisition part 52, and the storage 53 correspond to the functions implemented by the computer 12. All or some of these functions may be implemented by a dedicated electric circuit. Alternatively, these functions may be implemented by a plurality of computers.

Figure 25:
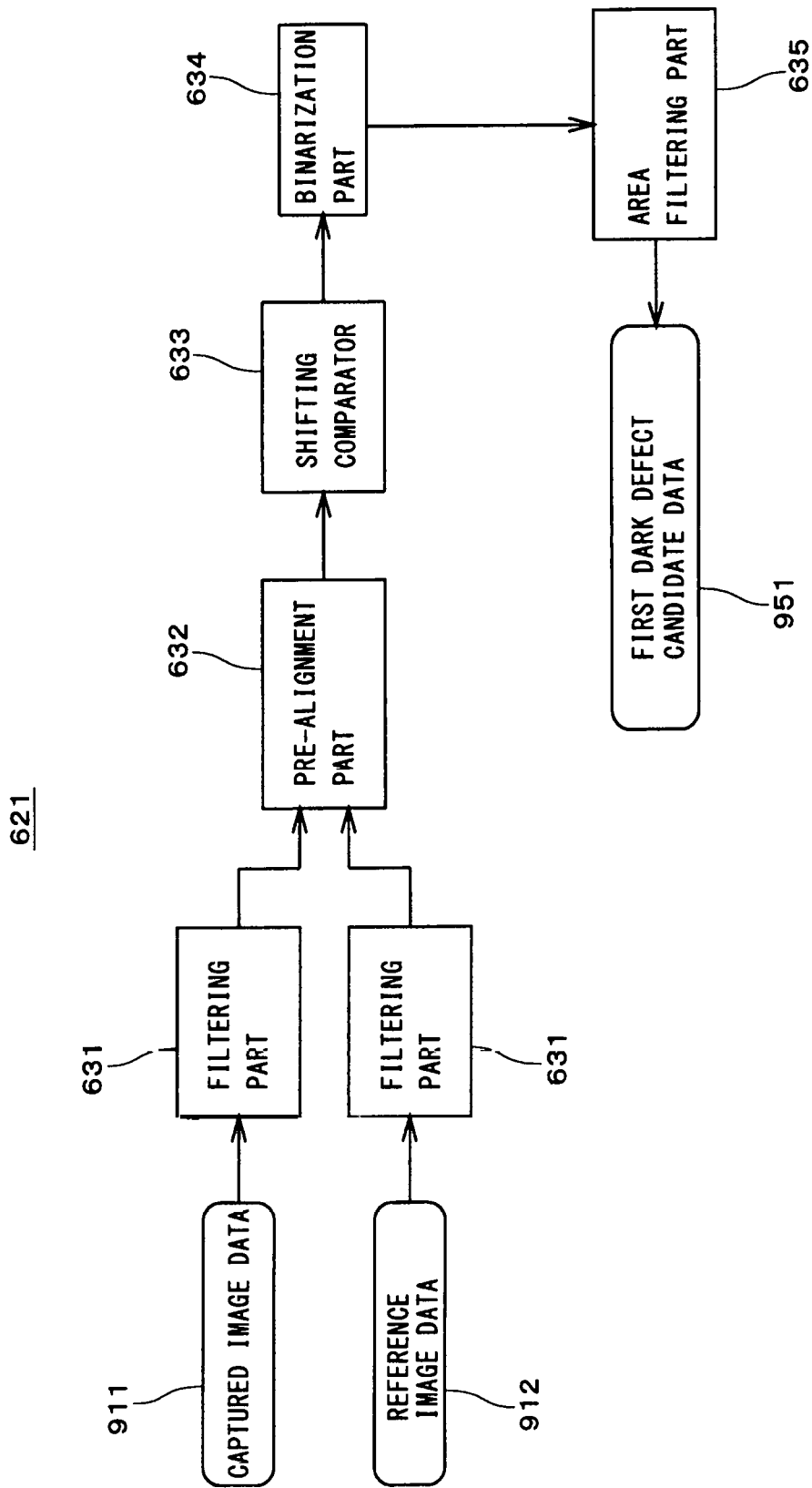
FIG. 25 illustrates a configuration of a first dark defect candidate acquisition part.

Each constituent element in the example in FIG. 24 is the same as that in FIG. 4, except for the defect acquisition part 52. The defect acquisition part 52 includes a first dark defect candidate acquisition part 621, a second dark defect candidate acquisition part 622, a first light defect candidate acquisition part 623, and a second light defect candidate acquisition part 624. Note that "dark defects" mean defects that appear dark in images. "Light defects" mean defects that appear light in images. FIG. 25 illustrates a configuration of the first dark defect candidate acquisition part 621. The first dark defect candidate acquisition part 621 includes two filtering parts 631, a pre-alignment part 632, a shifting comparator 633, a binarization part 634, and an area filtering part 635. The first dark defect candidate acquisition part 621 acquires first dark defect candidate data 951 that is image data indicating first dark defect candidate regions. The first dark defect candidate regions are regions where the captured image is darker than the reference image.

Figure 26:
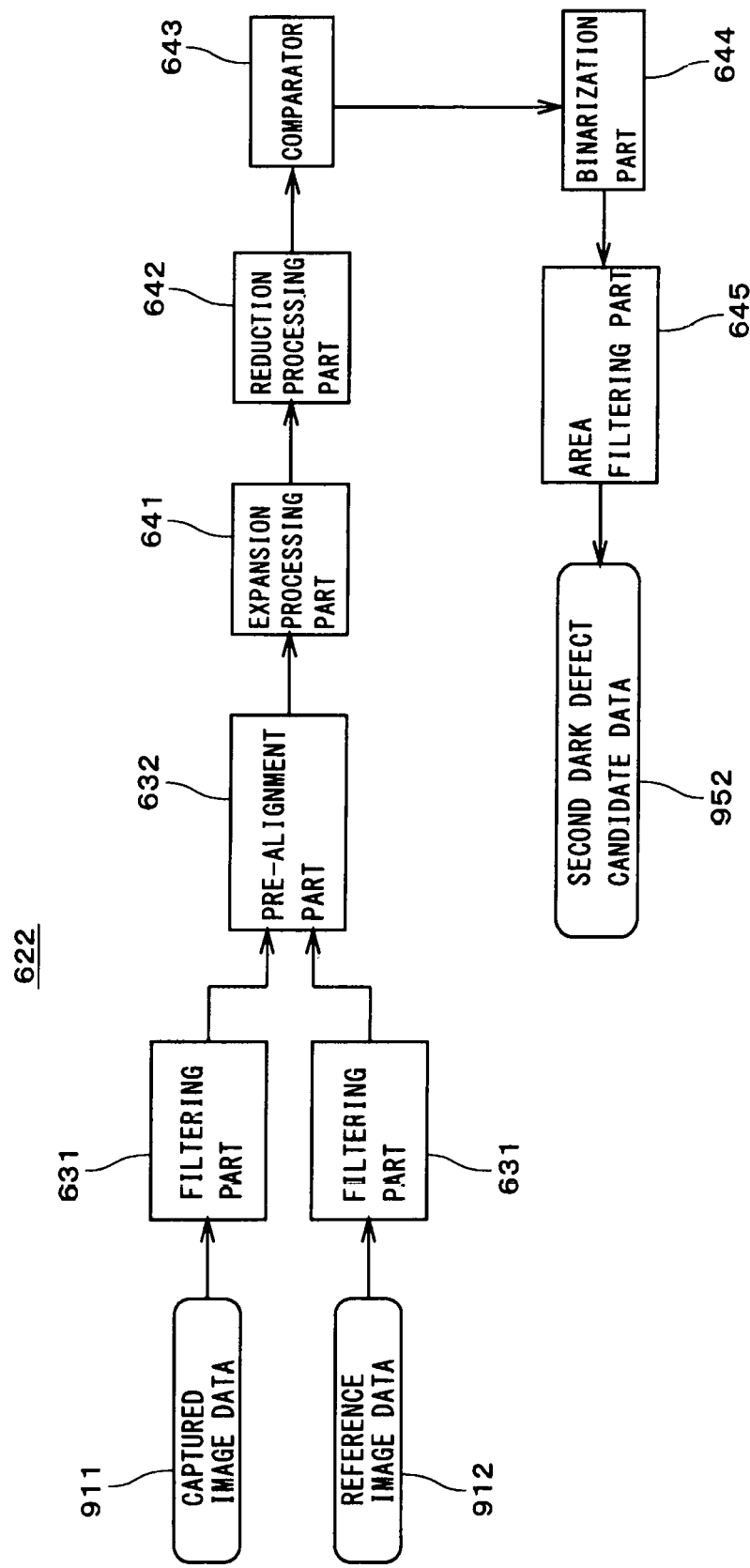
FIG. 26 illustrates a configuration of a second dark defect candidate acquisition part.

FIG. 26 illustrates a configuration of the second dark defect candidate acquisition part 622. In FIG. 26, the upstream side of the pre-alignment part 632 is common to the first dark defect candidate acquisition part 621. Following the pre-alignment part 632, the second dark defect candidate acquisition part 622 includes an expansion processing part 641, a reduction processing part 642, a comparator 643, a binarization part 644, and an area filtering part 645. The second dark defect candidate acquisition part 622 acquires second dark defect candidate data 952 that is image data indicating second dark defect candidate regions. The second dark defect candidate regions are regions where the captured image is darker than the reference image. As will be described later, the method of acquiring first dark defect candidate regions differs from the method of acquiring second dark defect candidate regions.

Figure 27:
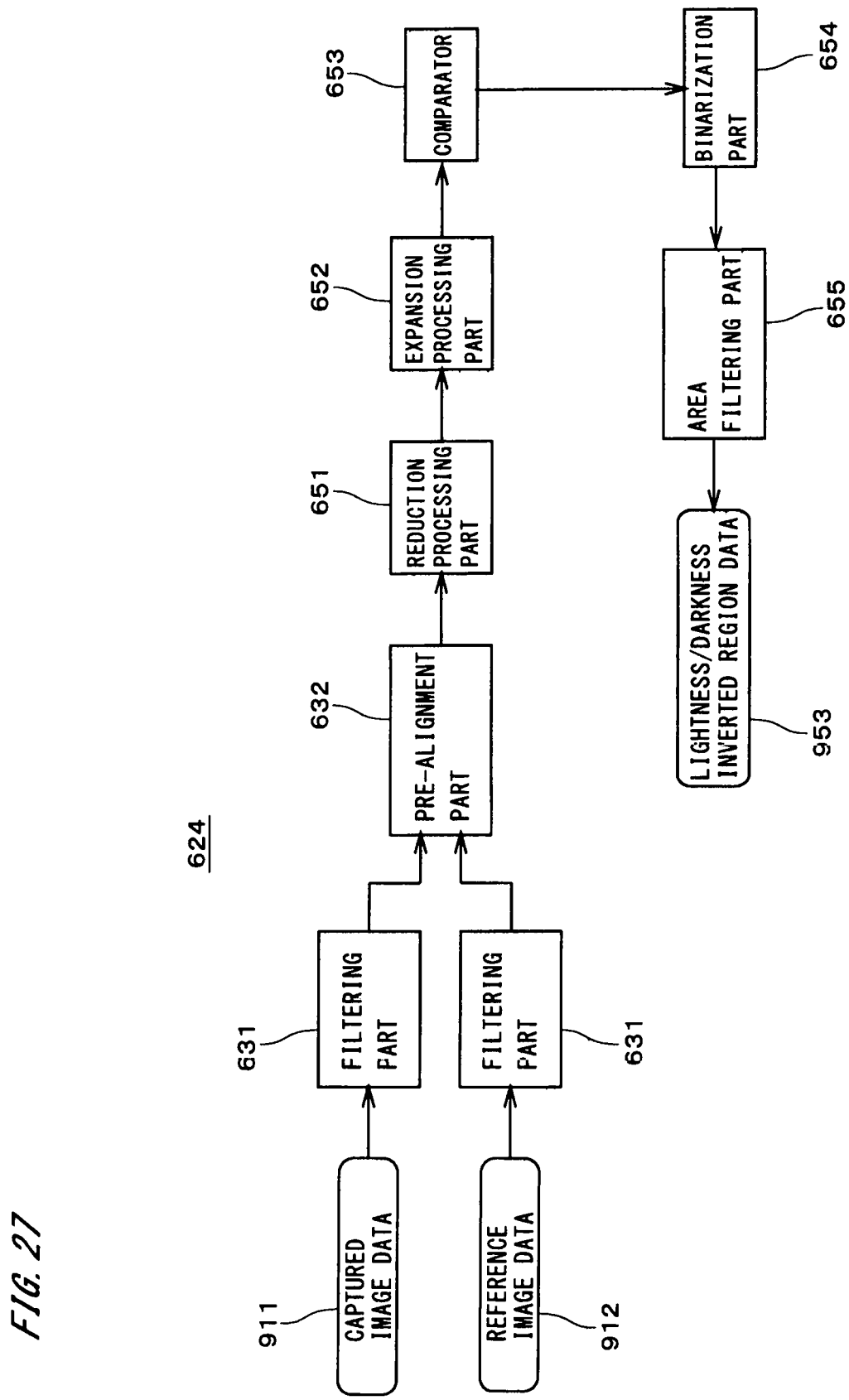
FIG. 27 illustrates a configuration of a second light defect candidate acquisition part.

FIG. 27 illustrates a configuration of the second light defect candidate acquisition part 624. In FIG. 27, the upstream side of the pre-alignment part 632 is common to the first dark defect candidate acquisition part 621. Following the pre-alignment part 632, the second light defect candidate acquisition part 624 includes a reduction processing part 651, an expansion processing part 652, a comparator 653, a binarization part 654, and an area filtering part 655. The second light defect candidate acquisition part 624 acquires lightness/darkness inverted region data 953 that is image data indicating lightness/darkness inverted regions, which will be described later.

In the case where processing is performed at high speed, a large number of first dark defect candidate acquisition parts 621, second dark defect candidate acquisition parts 622, first light defect candidate acquisition parts 623, and second light defect candidate acquisition parts 624 are provided in the defect acquisition part 52, so that processing is performed in parallel on a plurality of captured images.

Figure 28:
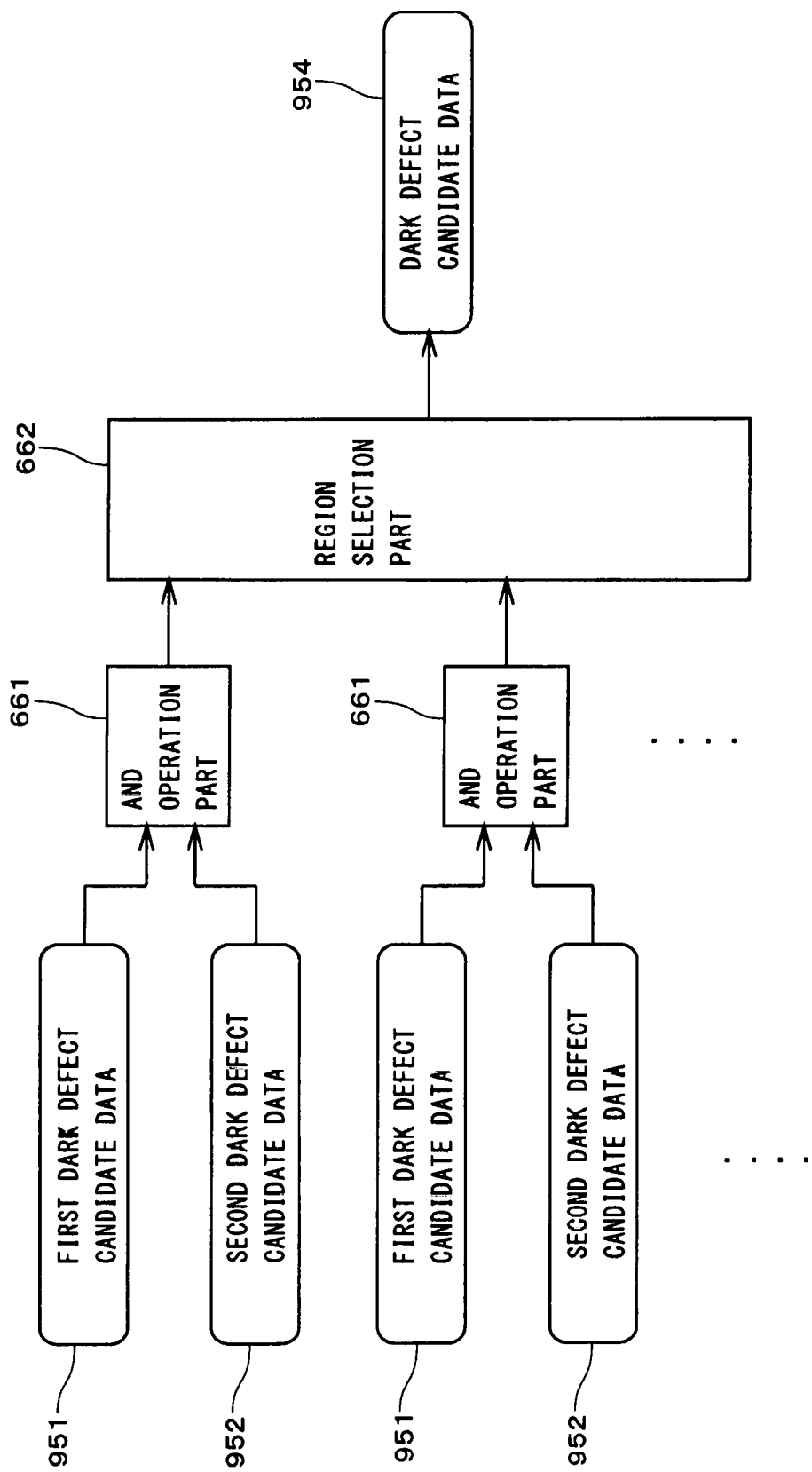
FIG. 28 illustrates a configuration of acquiring dark defect candidate data.
Figure 29:
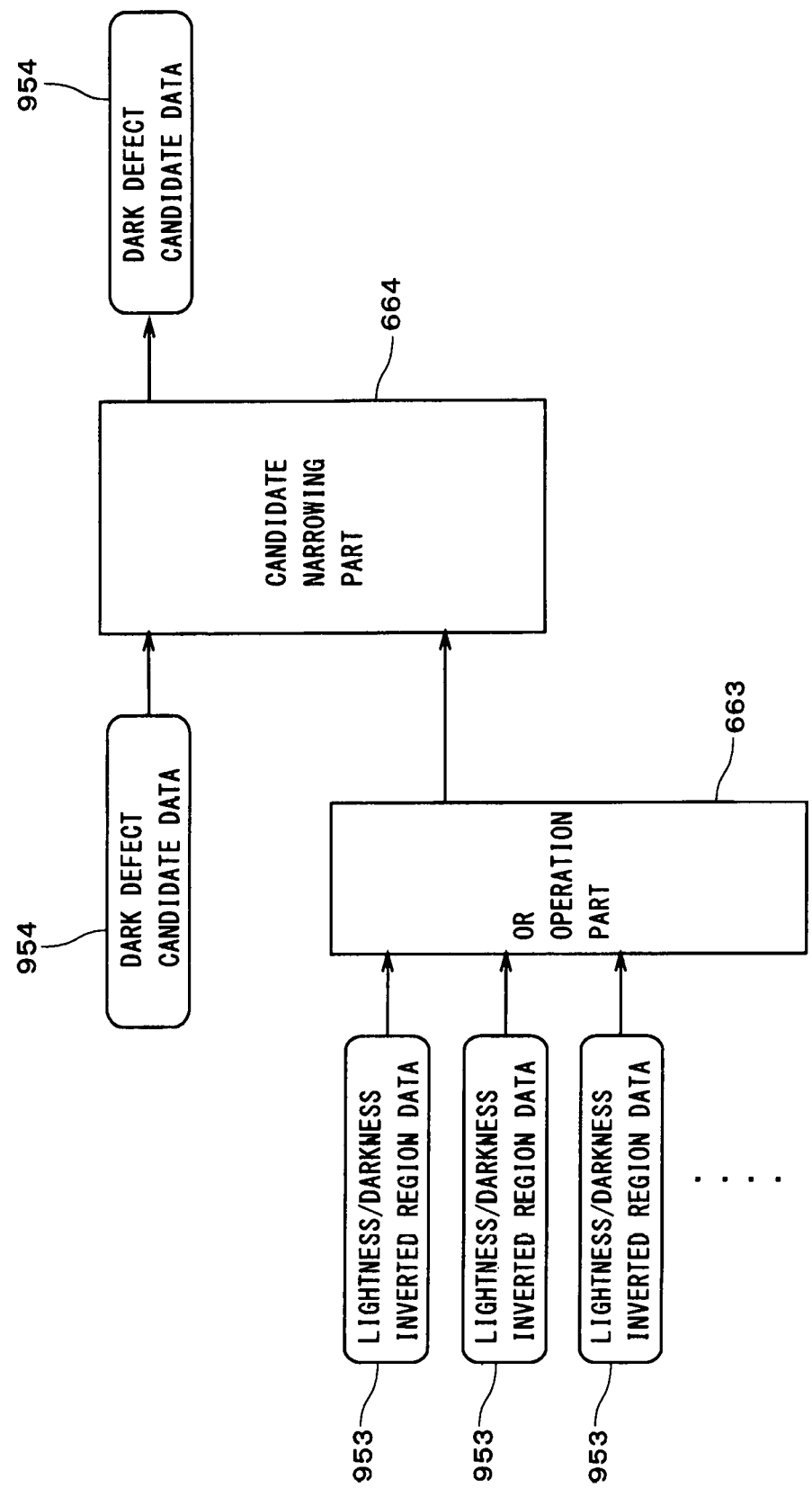
FIG. 29 illustrates a configuration of narrowing the dark defect candidate data.

FIG. 28 illustrates a configuration in the defect acquisition part 52 in which dark defect candidate data 954 that is image data indicating dark defect candidate regions is acquired from the first dark defect candidate data 951 and the second dark defect candidate data 952. This configuration includes a plurality of AND operation parts 661 and a region selection part 662. FIG. 29 illustrates a configuration in the defect acquisition part 52 in which the dark defect candidate regions indicated by the dark defect candidate data 954 are narrowed down by using the lightness/darkness inverted region data 953. This configuration includes an OR operation part 663 and a candidate narrowing part 664.

Figure 30:
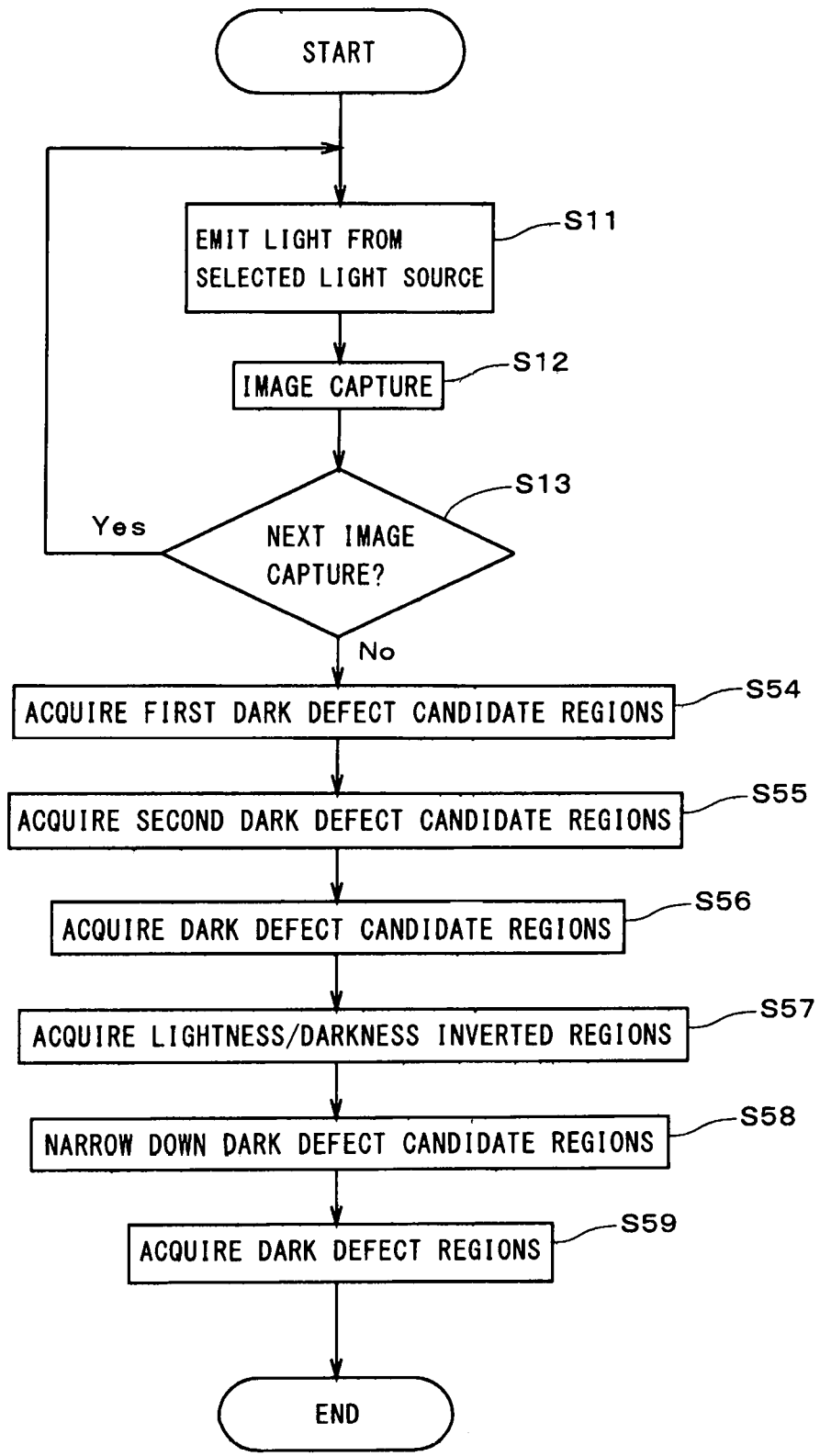
FIG. 30 illustrates a flow of operations of the defect detection device.

FIG. 30 illustrates a flow of operations of the defect detection device 1. Steps S11 to S13 in FIG. 30 are the same as steps S11 to S13 in FIG. 13.

In order to simplify the expression, processing that is performed on image data may hereinafter simply be expressed as processing that is performed on images. Description is given on only processing that focuses on one of the image capturing parts 3. The same processing is also performed for the other image capturing parts 3. Although the defect detection device 1 is capable of detecting the presence of dark defects and the presence of light defects, the following description focuses on only dark defects. The "dark defect candidate regions" as used herein refer to regions of an image that appear dark as candidates indicating the presence of defects.

After the execution of steps S11 to S13, first, one captured image is selected, and a reference image corresponding to that captured image is selected. As illustrated in FIG. 25, in the first dark defect candidate acquisition part 621, captured image data 911 of the captured image and reference image data 912 of the reference image are respectively input to the filtering parts 631.

The two filtering parts 631 perform filtering processing for reducing noise such as median filtering or Gaussian filtering respectively on the captured image and the reference image. The captured image and the reference image that have undergone the filtering processing are output to the pre-alignment part 632. The pre-alignment part 632 specifies the amounts of positional and angular displacements of the reference image relative to the captured image through pattern matching using a predetermined pattern. Then, the reference image is moved in parallel and rotated relative to the captured image by the amounts of positional and angular displacements between the two images, so that the position and angle of the reference image are approximately aligned with those of the captured image. In this way, the two images are pre-aligned.

The shifting comparator 633 obtains evaluation values that indicate a difference between the captured image and the reference image while moving the reference image little by little in the top, bottom, right, and left directions from the pre-aligned position. For example, a sum of the absolute values for (signed) differences of pixel values in a region of overlap between the two images is obtained as an evaluation value. Then, an image that indicates signed differences in pixel value between the two images at a position at which the evaluation value is a minimum is acquired. The signed difference image is binarized with a predetermined value so as to acquire a first dark defect candidate image indicating first dark defect candidate regions.

In actuality, the signed difference image is not obtained, in order to simplify the processing. Specifically, the values of pixels in a difference image are obtained by subtracting the value of each pixel in the captured image from the value of the corresponding pixel in the reference image, and if the obtained value is negative, setting the value to "0." A positive value is prepared in advance, and in the difference image, regions each composed of pixels having values greater than or equal to the positive value are acquired as first dark defect candidate regions. In general terms, in the first captured image, regions whose lightness is lower than in the first reference image and whose absolute values of the differences in lightness are greater than or equal to a first reference value are acquired as first dark defect candidate regions. The first reference value is a positive value. In yet other words, in the captured image, regions whose lightness is lower by a predetermined value or more than in the reference image are acquired as first dark defect candidate regions. In the case of a monochrome image, pixel values may be regarded as lightness, and in the case of a color image, values obtained by performing a predetermined computation on the values of pixels of each color component are treated as lightness.

The first dark defect candidate regions may be obtained from the ratio between the value of each pixel in the reference image and the value of the corresponding pixel in the captured image. Specifically, the values of pixels in a ratio image are obtained by dividing the value of each pixel in the reference image by the value of the corresponding pixel in the captured image. A first reference value greater than one is prepared in advance, and in the ratio image, regions each composed of pixels having values greater than or equal to the first reference value are acquired as first dark defect candidate regions. The values of pixels in the ratio image may, of course, be obtained by dividing the value of each pixel in the captured image by the value of the corresponding pixel in the reference image. In this case, in the ratio image, regions each composed of pixels having values less than or equal to a first reference value smaller than one are acquired as first dark defect candidate regions.

The first reference value does not necessarily have to be a constant. The first reference value may be a function of the lightness or pixel values of the reference image and/or the captured image. The first reference value may be determined using the difference and ratio in lightness or pixel value between the reference image and the captured image, or may be determined using other computations. The fact that the first reference value may be determined in various ways applies also to second and third reference values, which will be described later. The first to third reference values do not necessarily have to be the same value, and may be calculated in different ways. In general terms, in the captured image, regions whose lightness is lower than the lightness of the reference image and lower than a value that satisfies a predetermined condition are acquired as first dark defect candidate regions. The "predetermined condition" may be set individually for each captured image. Also, a plurality of "predetermined conditions" may be used for one captured image. For example, the first reference value may be set such that defect candidate regions are unlikely to be detected at positions at which pixel values tend to change for every image capture, such as edges in the captured image. The above description applies also to second dark defect candidate regions, first light defect candidate regions, and second light defect candidate regions, which will be described later.

Figure 31A:
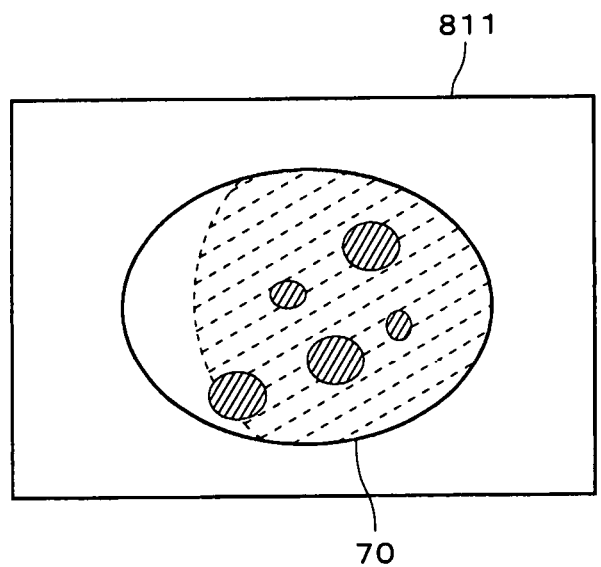
FIG. 31A illustrates an exemplary captured image.
Figure 31B:
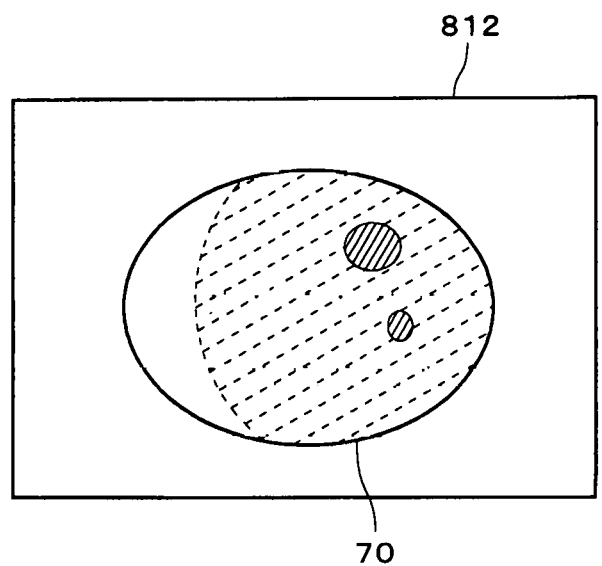
FIG. 31B illustrates an exemplary reference image.
Figure 31C:
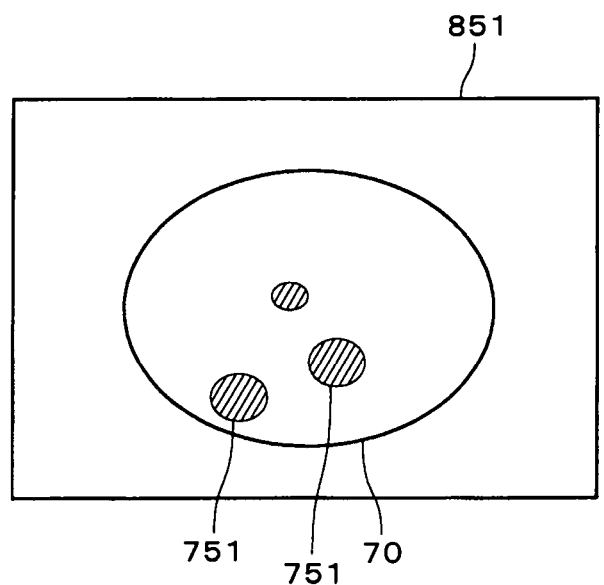
FIG. 31C illustrates a first dark defect candidate image.

FIG. 31A illustrates an exemplary captured image 811. FIG. 31B illustrates an exemplary reference image 812. Out of the surface of the object 9, a region that appears in the captured image is hereinafter referred to as a "target region 70." The image capturing parts 3 and the target regions 70 are in one-to-one correspondence, and each image capturing part 3 always acquires an image of the same target region 70. In FIGS. 31A and 31B, the target region 70 is illustrated in an abstract oval shape. A difference image between the two images (or a ratio image; the same applies below) is binarized so as to acquire a first dark defect candidate image 851 indicating first dark defect candidate regions 751 illustrated in FIG. 31C. Through the above-described processing, in the target region 70, regions where the captured image 811 is darker than the reference image 812 and that satisfy a predetermined condition are acquired as the first dark defect candidate regions 751. In the present embodiment, the values of pixels in the first dark defect candidate regions 751 are "1," and the values of pixels in the other region are "0."

When the first dark defect candidate regions 751 have been acquired, the area filtering part 635 deletes first dark defect candidate regions 751 whose areas are smaller than a predetermined value, so that an image that indicates the remaining first dark defect candidate regions 751 is acquired as a final first dark defect candidate image 851 (to be precise, first dark defect candidate data 951 that is image data indicating the first dark defect candidate regions 751).

The multiple captured images acquired by the image capturing parts 3 are sequentially selected as an object to be processed, so that the same number of first dark defect candidate images 851 as the number of captured images are acquired (step S54).

As illustrated in FIG. 26, in the second dark defect candidate acquisition part 622, the captured image data 911 and the reference image data 912 are input from the pre-alignment part 632 to the expansion processing part 641, and expansion processing is performed on the captured image and the reference image. The expansion processing as used herein refers to processing for expanding light regions in a multilevel image. Accordingly, small dark regions disappear. Data of the captured image and the reference image is further input to the reduction processing part 642, and reduction processing is performed on the captured image and the reference image. The reduction processing as used herein refers to processing for reducing light regions in a multilevel image. Accordingly, light regions are restored to almost their original sizes. As a result, large dark regions in the original captured image and the original reference image are maintained in almost their original states, and small dark regions disappear.

Figure 32A:
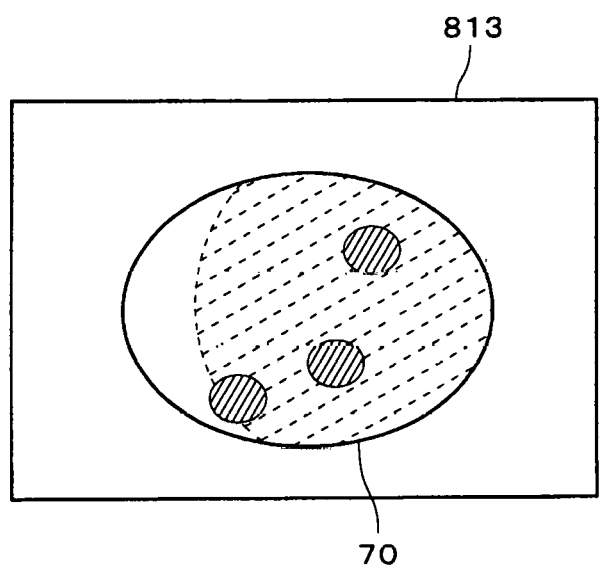
FIG. 32A illustrates a captured image that has undergone expansion and reduction processing.
Figure 32B:
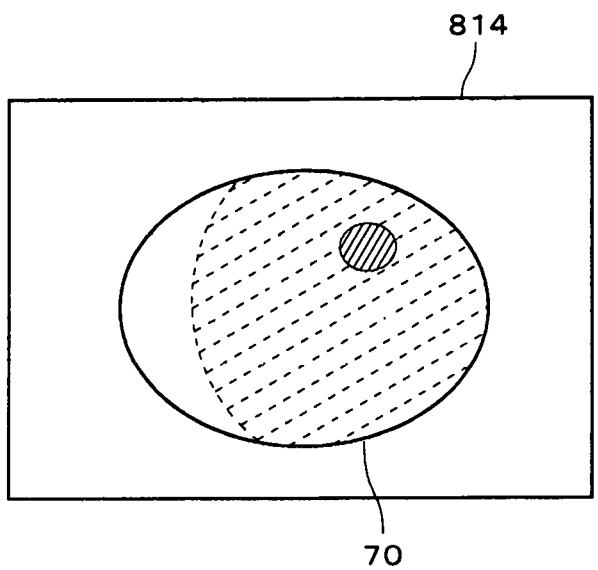
FIG. 32B illustrates a reference image that has undergone expansion and reduction processing.
Figure 32C:
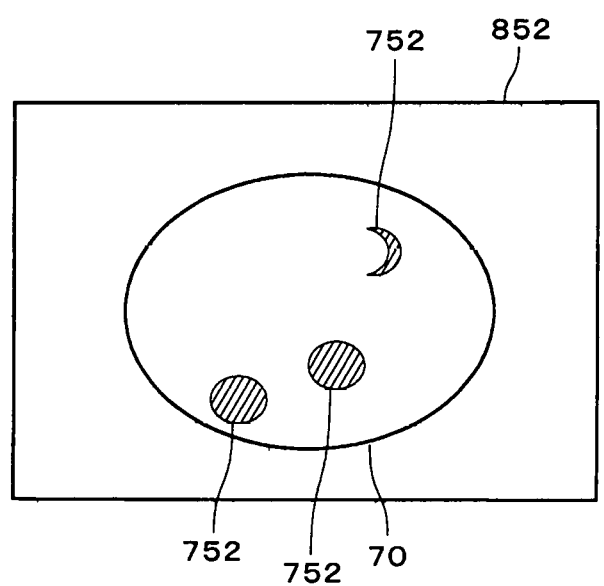
FIG. 32C illustrates a second dark defect candidate image.

FIG. 32A illustrates an exemplary image 813 obtained by performing the expansion and reduction processing on the captured image 811 in FIG. 31A. FIG. 32B illustrates an exemplary image 814 obtained by performing the expansion and reduction processing on the reference image 812 in FIG. 31B. In both of the images, small dark regions in the original images disappear. The comparator 643 generates difference image data for these images. The difference image is binarized with a second reference value by the binarization part 644. The processing for generating and binarizing the difference image is the same as the processing performed by the shifting comparator 633 and the binarization part 634 in FIG. 25, except that shifting is not performed. This processing is also the same in that a ratio image may be used, instead of the difference image. In this way, in the target region 70, regions where the captured image 811 is darker than the reference image 812 and that satisfy a predetermined condition are acquired as second dark defect candidate regions 752 as illustrated in FIG. 32C. In the present embodiment, the values of pixels in the second dark defect candidate regions 752 are "1" and the values of pixels in the other region are "0."

When the second dark defect candidate regions 752 have been acquired, the area filtering part 645 deletes second dark defect candidate regions 752 whose areas are smaller than a predetermined value, so that an image that indicates the remaining second dark defect candidate regions 752 is acquired as a final second dark defect candidate image 852 (to be precise, second dark defect candidate data 952 that is image data indicating the second dark defect candidate regions 752).

The multiple captured images acquired by the image capturing parts 3 are sequentially selected as an object to be processed, so that the same number of second dark defect candidate images 852 as the number of captured images are acquired (step S55).

Figure 33:
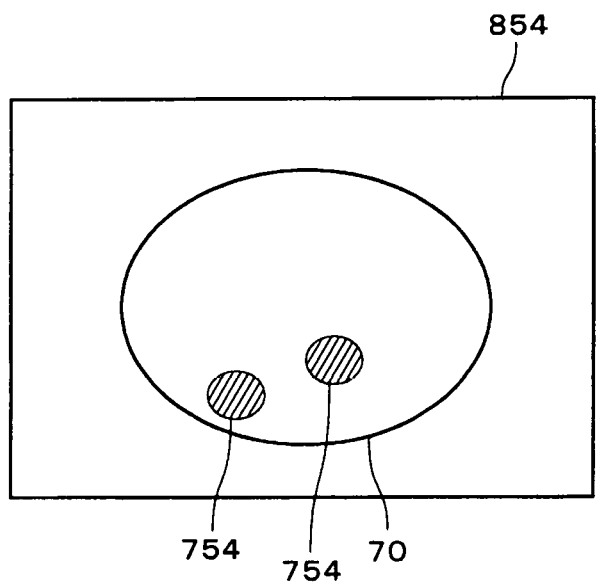
FIG. 33 illustrates a dark defect candidate image.

As illustrated in FIG. 28, the first dark defect candidate data 951 and the second dark defect candidate data 952 that are generated from the same captured image and the corresponding reference image are input to one AND operation part 661. The region selection part 662 receives input of data of AND images that are obtained from each combination of the first dark defect candidate image 851 and the second dark defect candidate image 852. Each AND image is an image that indicates dark defect candidate regions generated from first dark defect candidate regions and second dark defect candidate regions. FIG. 33 illustrates an exemplary dark defect candidate image 854 that indicates dark defect candidate regions 754 generated from the first dark defect candidate regions 751 in FIG. 31C and the second dark defect candidate regions 752 in FIG. 32C.

The first dark defect candidate regions are obtained from the difference image between the captured image and the reference image after alignment of these images, so that the reliability of indication of the presence of defects is high. However, small first dark defect candidate regions may have been generated due to some causes such as noise. On the other hand, the second dark defect candidate regions 752 are obtained from the difference image between the captured image and the reference image after minute-region removal processing for deleting small dark regions has been performed on these images, so that small false defects are less likely to be detected. However, false defects may be detected due to inaccurate alignment resulting from limited processing time. In view of this, in the present embodiment, an AND image between the first dark defect candidate image and the second dark defect candidate image is obtained so as to acquire a dark defect candidate image that indicates more reliable dark defect candidate regions.

In the case of overlaying a plurality of dark defect candidate images, the region selection part 662 maintains overlapping regions where a predetermined number or more of dark defect candidate regions overlap as dark defect candidate regions. The "overlapping region" as used herein may be a logical OR of a plurality of regions that overlap, or a logical AND thereof. In the present embodiment, regions where the number of regions that overlap is two or more are maintained as dark defect candidate regions. The region selection part 662 acquires one dark defect candidate image that indicates narrowed dark defect candidate regions from a plurality of dark defect candidate images that indicate dark defect candidate regions (step S56). Through the above-described processing, regions that are darker than in the reference image are acquired as dark defect candidate regions from a plurality of captured images acquired in a plurality of illumination states while referencing the corresponding reference images.

Since the dark defect candidate regions are narrowed down by the region selection part 662, in actuality OR operation parts may be used, instead of the AND operation parts 661. In either case, the reliability of dark defect candidate regions can be improved by acquiring the dark defect candidate regions on the basis of the first dark defect candidate regions and the second dark defect candidate regions. The number of regions that overlap, used to determine dark defect candidate regions to be maintained, may be three or more, or may be one or more. In the case where the number of regions that overlap is set to one or more, all dark defect candidate regions are maintained, and the region selection part 662 simply generates an OR image of a plurality of dark defect candidate images as one dark defect candidate image.

On the other hand, as illustrated in FIG. 27, the second light defect candidate acquisition part 624 acquires data of a lightness/darkness inverted region image indicating lightness/darkness inverted regions through processing for inverting lightness and darkness from those in the case of the second dark defect candidate acquisition part 622.

Specifically, in the second light defect candidate acquisition part 624, the captured image data 911 and the reference image data 912 are input from the pre-alignment part 632 to the reduction processing part 651, and reduction processing is performed on the captured image and the reference image.

The reduction processing as used herein refers to processing for reducing light regions in a multilevel image, and also refers to expansion processing for dark regions. Accordingly, small light regions disappear. Data of the captured image and the reference image is further input to the expansion processing part 652, and expansion processing is performed on the captured image and the reference image. The expansion processing as used herein refers to processing for expanding light regions in a multilevel image, and also refers to reduction processing for dark regions. Accordingly, dark regions are restored to almost their original sizes. As a result, large light regions in the original captured image and the original reference image are maintained in almost their original states, and small light regions disappear.

The comparator 653 generates difference image data for these images. The difference image is binarized with a third reference value by the binarization part 654. Instead of the difference image, a ratio image may be used. In the present embodiment, the values of pixels in the lightness/darkness inverted regions are "1" and the values of pixels in the other region are "0."

When the lightness/darkness inverted regions have been acquired, the area filtering part 655 deletes lightness/darkness inverted regions whose areas are smaller than a predetermined value, so that an image that indicates the remaining lightness/darkness inverted regions is acquired as a final lightness/darkness inverted region image (to be precise, lightness/darkness inverted region data 953 that is image data indicating lightness/darkness inverted regions).

The multiple captured images acquired by the image capturing parts 3 are sequentially selected as an object to be processed, so that the same number of lightness/darkness inverted region images as the number of captured images are acquired (step S57). Through the processing described above, a region that is lighter than in the reference image is acquired as a lightness/darkness inverted region from each of a plurality of captured images acquired in a plurality of illumination states while referencing the corresponding reference image.

Figure 34A:
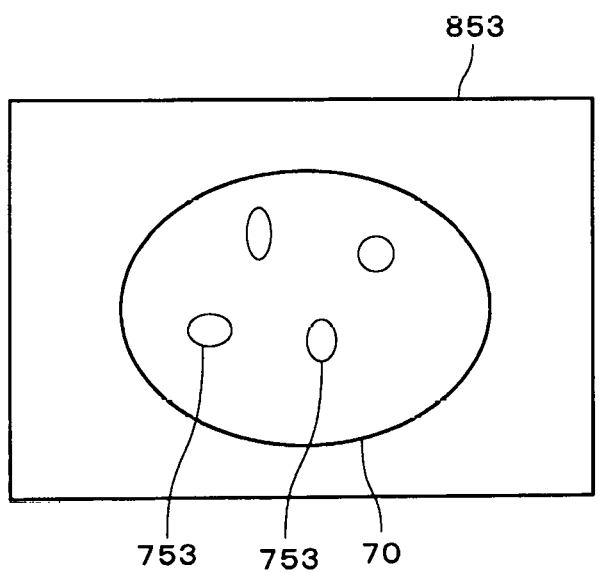
FIG. 34A illustrates an exemplary lightness/darkness inverted region image.
Figure 34B:
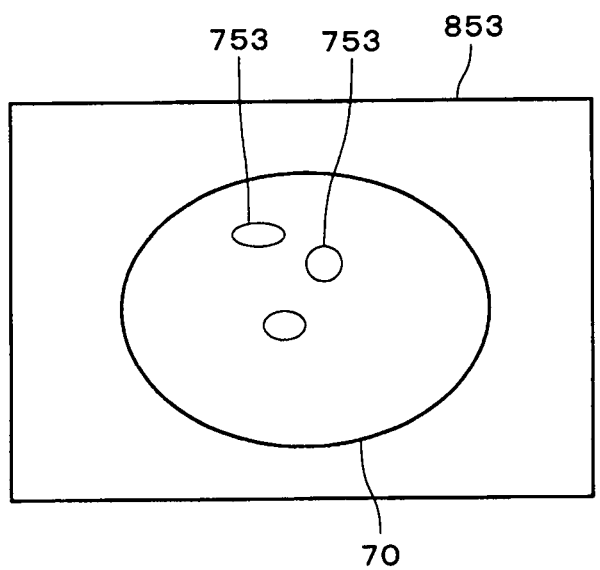
FIG. 34B illustrates another exemplary lightness/darkness inverted region image.
Figure 34C:
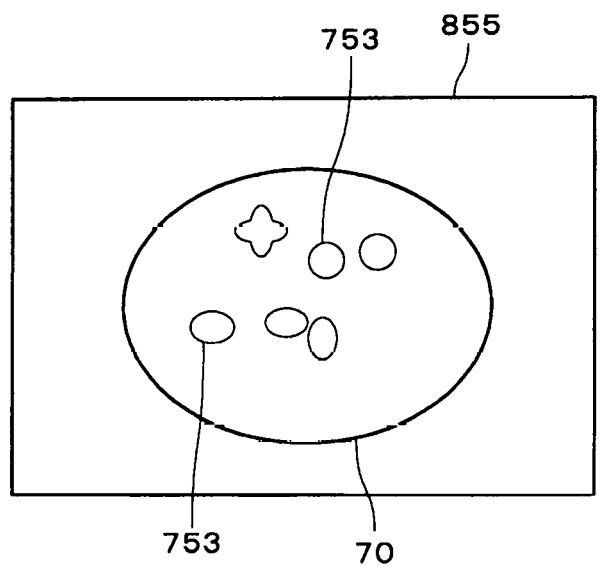
FIG. 34C illustrates an OR image.

As illustrated in FIG. 29, a plurality of pieces of lightness/darkness inverted region data 953 is input to the OR operation part 663, and data of an OR image of the lightness/darkness inverted region images is generated. FIGS. 34A and 34B illustrate exemplary lightness/darkness inverted region images 853 that indicate lightness/darkness inverted regions 753. FIG. 34C illustrates an OR image 855 of these images. The actual number of lightness/darkness inverted region images is less than or equal to the number of captured images acquired by one image capturing part 3, and preferably two or more.

Figure 35:
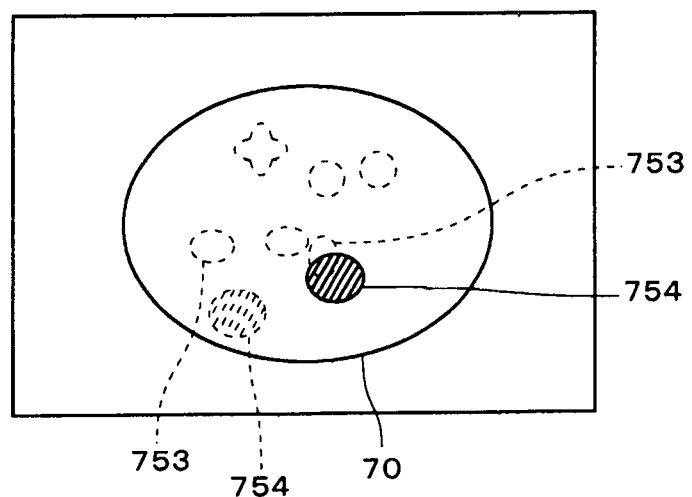
FIG. 35 illustrates a dark defect candidate image and an OR image that are overlaid on each other.

Data of the OR image is input to the candidate narrowing part 664. The candidate narrowing part 664 excludes, among the dark defect candidate regions, dark defect candidate regions that do not overlap with any of the lightness/darkness inverted regions in the OR image from defect candidates. This further narrows down the dark defect candidate regions. FIG. 35 illustrates the dark defect candidate image 854 in FIG. 33 and the OR image 855 in FIG. 34C that are overlaid. The dark defect candidate region 754 on the right side overlaps with a lightness/darkness inverted region 753 and is thus maintained as a defect candidate. The dark defect candidate region 754 on the left side does not overlap with any of the lightness/darkness inverted regions 753 and is thus excluded from defect candidates (step S58).

Note that the presence or absence of overlaps between the dark defect candidate regions 754 and the lightness/darkness inverted regions 753 may be determined by sequentially overlaying the dark defect candidate image 854 on each lightness/darkness inverted region image 853 without obtaining an OR image.

Alternatively, only if the area of overlap between the dark defect candidate regions 754 and the lightness/darkness inverted regions 753 is larger than or equal to a predetermined area, that overlap may be detected as existing. In this case, dark defect candidate regions 754 whose areas of overlaps with the lightness/darkness inverted regions 753 are smaller than the predetermined area are excluded from defect candidates. As another alternative, if the ratio of the area of overlap between a dark defect candidate region 754 and a lightness/darkness inverted region 753 to the area of the dark defect candidate region 754 is less than a predetermined ratio, that dark defect candidate region 754 may be excluded from defect candidates. In this way, among the dark defect candidate regions, those that do not overlap by a prescribed criterion or more with any of the lightness/darkness inverted regions are excluded from defect candidates. In other words, among the dark defect candidate regions, those that overlap by a prescribed criterion or more with any of the lightness/darkness inverted regions are maintained as dark defect candidates.

Thereafter, processing such as deleting dark defect candidate regions whose areas are smaller than or equal to a predetermined area is performed as necessary, and final dark defect regions are acquired on the basis of the dark defect candidate regions. That is, the presence of dark defects is acquired (step S59). In the case where there is a defect in the target region 70 viewed from one image capturing part 3, the position of the defect is detected through the processing described above.

On the display of the computer 12, one captured image is displayed, and dark defect regions is displayed on the target region 70.

In the case where the surface of the object 9 has depressed or projecting defects, those defects may appear light or dark in captured images if directional light is applied to the surface. However, if defects are to be detected using only dark regions, even surface grime transferred from unnecessarily oil or a coating will be detected as defects. In view of this, the lightness/darkness inverted region images are used so as to remove dark regions arising from the surface color as noise. This suppresses over-detection of defects. In particular, the emergence of lightness and darkness due to the presence of defects is complicated, and therefore it is possible to exclude, from defect candidates, those that arise from surface color with high accuracy by using a plurality of lightness/darkness inverted region images.

A minimum number of captured images acquired by one image capturing part 3 is two, but preferably three or more. That is, the light emission part 4 can provide three or more illumination states that are different from one another, and for example, can irradiate the object 9 with light from three or more directions, and the image capturing parts 3 acquire images during the three or more illumination states under the control of the image capture controller 51. In the case where a preferable illumination state is commonly known, at least one of three or more captured images acquired on the basis of that information may be selected as a captured image to be processed. More appropriate defect detection can easily be conducted by preparing three or more captured images.

As described previously, the defect detection device 1 also has a function of detecting light defects. The detection of light defects is conducted in the same manner as in steps S54 to S59, except that lightness and darkness are inverted from those in the detection of dark defects. The configuration of the first light defect candidate acquisition part 623 is the same as that of the first dark defect candidate acquisition part 621 in FIG. 25, except that a different order of computations and different values are used. That is, the first light defect candidate acquisition part 623 obtains a difference image between the captured image and the reference image after aligning these images and then binarizes the difference image. Accordingly, a first light defect candidate image that indicates first light defect candidate regions is acquired. The second light defect candidate acquisition part 624 acquires a difference image between the captured image and the reference image by performing reduction and expansion processing thereon and then binarizes the difference image. Accordingly, a second light defect candidate image that indicates second light defect candidate regions is acquired.

With the configuration illustrated in FIG. 28, a light defect candidate image that indicates light defect candidate regions is generated from a plurality of combinations of the first light defect candidate image and the second light defect candidate image. On the other hand, the second dark defect candidate acquisition part 622 functions as a lightness/darkness inverted region acquisition part and acquires a second dark defect candidate image as a lightness/darkness inverted region image. Then, an OR image of a plurality of lightness/darkness inverted region images is generated.

Among the light defect candidate regions, those that do not overlap by a prescribed criterion or more with any of the lightness/darkness inverted regions are excluded from defect candidates so as to narrow down the light defect candidate regions. Thereafter, a light defect image that indicates the presence or absence of light defects is generated using the light defect candidate image. Through the processing described above, over-detection of light defects arising from such as light-colored grime is suppressed.

The dark defect regions and the light defect regions are, for example, displayed as regions colored in different colors in one captured image on the display.

In the case of conducting the detection of dark defects and the detection of light defects, from the viewpoint of reducing the amount of information and thereby increasing the processing speed, it is preferable for the second light defect candidate regions used in the detection of light defects to be used as lightness/darkness inverted regions in order to narrow down the defect candidate regions. In order to narrow down the light defect candidate regions, it is preferable for the second dark defect candidate regions used in the detection of dark defects to be used as lightness/darkness inverted regions. That is, the step of acquiring lightness/darkness inverted regions, performed at the time of acquiring one of the dark defect candidate regions and the light defect candidate regions, is preferably included in the step of acquiring the other of the dark defect candidate regions and the light defect candidate regions. However, if the operation time is acceptable, it is conceivable to use more preferable regions as lightness/darkness inverted regions.

The reference value serving as a threshold value in binarization when obtaining dark defect candidate regions or light defect candidate regions is set to an optimum value at which even omissions in detection can be suppressed while suppressing over-detection. On the other hand, the lightness/darkness inverted regions are used to suppress detection of false defects arising from, for example, surface color such as grime or noise. Thus, if the reference value serving as a threshold value in binarization when obtaining lightness/darkness inverted regions is set to a value at which even doubtful lightness/darkness inverted regions are detected as lightness/darkness inverted regions, it is possible to reduce the possibility that true defects are excluded as, for example, grime.

Accordingly, if the reference value (third reference value in the above description) used by the second light defect candidate acquisition part 624 when acquiring dark defect candidate regions is made smaller than the reference value used by the second light defect candidate acquisition part 624 when acquiring light defect candidate regions, more accurate dark defect candidate regions can be obtained. Also, if the reference value used by the second dark defect candidate acquisition part 622 when acquiring light defect candidate regions is made smaller than the reference value (second reference value in the above description) used by the second dark defect candidate acquisition part 622 when acquiring dark defect candidate regions, more preferable light defect candidate regions can be obtained.

In this way, the reference value used in binarization when acquiring lightness/darkness inverted regions may differ from the reference value that is used in binarization when acquiring second dark defect candidate regions or second light defect candidate regions. Preferably, the reference value used in binarization when acquiring lightness/darkness inverted regions is more lenient than the reference value used in binarization when acquiring second dark defect candidate regions or second light defect candidate regions. The area of lightness/darkness inverted regions is larger than the area of second dark defect candidate regions or second light defect candidate regions.

Although the above description is given while drawing a distinction between the detection of dark defects and the detection of light defects, the defect candidates as used in the defect detection device 1 mean either or both of the dark defect candidates and the light defect candidates. Generally, in the above description, the dark defect candidates and the light defect candidates can be expressed as "defect candidates," the dark defect candidate regions and the light defect candidate regions can be expressed as "defect candidate regions," and the dark defect candidate images and the light defect candidate images can be expressed as "defect candidate images." The first dark defect candidate regions and the first light defect candidate regions can be expressed as "first defect candidate regions," and the second dark defect candidate regions and the second light defect candidate regions can be expressed as "second defect candidate regions."

In the above-described embodiment, the defect acquisition part 52 acquires one of regions that are darker than in the reference image and regions that are lighter than in the reference image as defect candidate regions from a captured image used for defect detection while referencing the corresponding reference image. The defect acquisition part 52 also acquires the other of the regions that are darker than in the reference image and the regions that are lighter than in the reference image as the other defect candidate regions from the captured image used for defect detection while referencing the corresponding reference image. In order to improve the efficiency of processing, lightness/darkness inverted regions that correspond to the defect candidate regions described above are acquired when acquiring the other defect candidate regions described above. Also, in order to improve the accuracy of defect detection without sticking to the efficiency of processing, lightness/darkness inverted regions that correspond to the defect candidate regions described above are acquired using a reference value that is different from the reference value used to acquire the other defect candidate regions described above.

In the above-described embodiment, if the method of acquiring the first defect candidate regions is expressed as a first method and the method of acquiring the second defect candidate regions is expressed as a second method, various methods are usable as these methods as long as the first method and the second method are different from each other. Accordingly, over-detection or omissions in detection can more efficiently be suppressed.

Alternatively, the defect candidate regions may be obtained by only one method. For example, in the above-described embodiment, the region selection part 662 may acquire, among the first defect candidate regions in a plurality of first defect candidate images, those where a predetermined number or more of first defect candidate regions overlap as defect candidate regions, without obtaining the second defect candidate regions. As another alternative, in the above-described embodiment, the region selection part 662 may acquire, among the second defect candidate regions in a plurality of second defect candidate images, those where a predetermined number or more of second defect candidate regions overlap as defect candidate regions, Without obtaining the first defect candidate regions.

In the above-described embodiment, the number of captured images used for defect detection may be one. The number of captured images used to acquire lightness/darkness inverted region images is preferably two or more. In order to improve the efficiency of image capture, at least one captured image used for defect detection is preferably included in a plurality of captured images acquired in a plurality of illumination states so as to acquire lightness/darkness inverted regions.

The processing order can be appropriately changed if substantially the same processing is performed. The processing order described in the above embodiment is merely one example. For example, the step of acquiring first dark defect candidate regions, the step of acquiring second dark defect candidate regions, and the step of acquiring lightness/darkness inverted regions may be performed in any arbitrary order, or may be performed in parallel. The processing for detecting dark defects and the processing for detecting light defects may be performed in any arbitrary order, or may be performed in parallel. The defect candidate regions may be handled directly as defect regions.

Reference images may be generated from captured images. That is, defect candidate regions may be acquired by so-called self-comparison. For example, a reference image whose dark defects are caused to disappear can be acquired by performing processing for expanding light regions on a captured image and then performing reduction processing thereon. A reference image whose light defects are caused to disappear can be acquired by performing processing for reducing light regions on a captured image and then performing expansion processing thereon.

The defect detection device 1 described above can be modified in various ways.

The arrangement and numbers of the light sources 4a, 4b, and 4c and the image capturing parts 3 may be appropriately changed. The illumination state of the light emission part 4 may be modified in various ways. Among the plurality of light sources, two may be turned on at a time, or three may be turned on at a time. The light emission part 4 may change the illumination state by moving light sources.

The computer 12 may be implemented by dedicated hardware, or part of the computer 12 may be implemented by dedicated hardware. In the case of high-speed external appearance inspection, it is preferable for parallel processing to be performed by a computer or dedicated hardware.

The processing order can be appropriately changed as long as substantially the same processing is performed. The processing order described in the above embodiment is merely one example.

The defect detection device 1 may be used to detect defects on the surfaces of other objects such as various types of substrates having patterns or films. The defect detection device 1 is in particular suitable for the inspection of objects that are likely to cause over-detection due to satin-finish regions of their surfaces (which are not limited to metallic surfaces).

The configurations of the above-described preferred embodiments and variations may be appropriately combined as long as there are no mutual inconsistencies.

While the invention has been shown and described in detail, the foregoing description is in all aspects illustrative and not restrictive. It is therefore to be understood that numerous modifications and variations can be devised without departing from the scope of the invention.

REFERENCE SIGNS LIST

1 Defect detection device
2 Holder
3 Image capturing part (3a: upper image capturing part, 3b: oblique image capturing part, 3c: lateral image capturing part)
4 Light emission part (4a: upper light source, 4b: oblique light source, 4c: lateral light source)
8 Recording medium
9 Object
11 Main body
12 Computer
51 Image capture controller
52 Defect acquisition part
53 Storage
70 Target region
80 Program
124 Fixed disk
125 Display
126 Input part (126a: keyboard, 126b: mouse)
127 Reader
128 Communication part
521 First defect acquisition part
522 Second defect acquisition part
541 First defect candidate acquisition part
544 Expansion processing part
545 Reduction processing part
546 Comparator
551 Third defect candidate acquisition part
554 Comparator
561 Second defect candidate acquisition part
564 Reduction processing part
565 Expansion processing part
566 Comparator
571 Fourth defect candidate acquisition part
571 Comparator
581 Defect candidate narrowing part
582, 583 AND operation part
584 Region selection part
591 Defect candidate narrowing part
592, 593 AND operation part
711 First defect
721 Second defect
751 First dark defect candidate region
752 Second dark defect candidate region
753 Lightness/darkness inverted region 754 Dark defect candidate region
811 Captured image
812 Reference image
S12 Image capturing step
S14 First defect acquisition step
S141 First defect candidate acquisition step
S1411 First defect candidate region detection step
S1412 First mask region detection step
S1413 Defect candidate excluding step
S142 Third defect candidate acquisition step
S143 Defect candidate narrowing step
S15 Second defect acquisition step
S151 Second defect candidate acquisition step
S1511 Second defect candidate region detection step
S1512 Second mask region detection step
S1513 Defect candidate excluding step
S152 Third defect candidate acquisition step
S153 Defect candidate narrowing step
S203, S213, S304, S314 Expansion processing step
S204, S214, S303, S313 Reduction processing step
S205, S215, S305, S315 Comparison processing step
S54 to S59 Step

The invention claimed is:

1. A defect detection device for detecting a surface defect in an object, comprising:
an image capturing part for capturing an image of an object to acquire a captured image;
a storage for storing a reference image that corresponds to said captured image; and
a defect acquisition part configured to:
detect a first defect candidate region on the basis of at least one of a difference and a ratio between pixel values in said captured image and respective pixel values in a first image, wherein the first image is obtained by performing one of expansion processing and reduction processing on said captured image and then performing the other of the expansion processing and the reduction processing on said processed captured image,
detect a first mask region on the basis of at least one of a difference and a ratio between pixel values in said reference image and respective pixel values in a second image, wherein the second image is obtained by performing the one of the expansion processing and the reduction processing on said reference image and then performing the other of the expansion processing and the reduction processing on said processed reference image,
exclude a region of said first defect candidate region that overlaps with said first mask region from a first defect candidate, and
acquire presence of a first defect in said captured image on the basis of said first defect candidate region.

2. The defect detection device according to claim 1, wherein
the defect acquisition part acquires presence of the first defect and a second defect different from said first defect in said captured image, and
the defect acquisition part includes:
a first defect acquisition part configured to:
detect the first defect candidate region on the basis of at least one of the difference and the ratio between pixel values in said captured image and respective pixel values in the first image, wherein the first image is obtained by performing the expansion processing on said captured image and then performing the reduction processing on said expansion-processed captured image,
detect the first mask region on the basis of at least one of the difference and the ratio between pixel values in said reference image and respective pixel values in the second image, wherein the second image is obtained by performing the expansion processing on said reference image and then performing the reduction processing on said expansion-processed reference image,
exclude a region of said first defect candidate region that overlaps with said first mask region from the first defect candidate, and
acquire presence of the first defect in said captured image on the basis of said first defect candidate region; and
a second defect acquisition part configured to:
detect a second defect candidate region on the basis of at least one of a difference and a ratio between pixel values in said captured image and respective pixel values in a third image, wherein the third image is obtained by performing the reduction processing on said captured image and then performing the expansion processing on said reduction-processed captured image,
detect a second mask region on the basis of at least one of a difference and a ratio between pixel values in said reference image and respective pixel values in a fourth image, wherein the fourth image is obtained by performing the reduction processing on said reference image and then performing the expansion processing on said reduction-processed reference image,
exclude a region of said second defect candidate region that overlaps with said second mask region from a second defect candidate, and
acquire presence of a second defect in said captured image on the basis of said second defect candidate region.

3. The defect detection device according to claim 2, wherein
said first defect acquisition part acquires the presence of the first defect in said captured image on the basis of said first defect candidate region by, after aligning said captured image and said reference image, acquiring a region where said captured image is darker than said reference image as a third defect candidate region on the basis of the difference image between said captured image and said reference image and excluding a region of said first defect candidate region that does not overlap with said third defect candidate region from the first defect candidate, and
said second defect acquisition part acquires the presence of the second defect in said captured image on the basis of said second defect candidate region by, after aligning said captured image and said reference image, acquiring a region where said captured image is lighter than said reference image as a fourth defect candidate region on the basis of the difference image between said captured image and said reference image and excluding a region of said second defect candidate region that does not overlap with said fourth defect candidate region from the second defect candidate.

4. A defect detection method of detecting a surface defect in an object, comprising:

a) an image capturing step of capturing an image of an object with an image capturing part to acquire a captured image;
b) a defect candidate region detection step of detecting a defect candidate region on the basis of at least one of a difference and a ratio between pixel values in said captured image and respective pixel values in a first image, wherein the first image is obtained by performing one of expansion processing and reduction processing on said captured image and then performing the other of the expansion processing and the reduction processing on said processed captured image;
c) a mask region detection step of, after a reference image corresponding to said captured image is prepared, detecting a mask region on the basis of at least one of a difference and a ratio between pixel values in said reference image and respective pixel values in a second image, wherein the second image is obtained by performing the one of the expansion processing and the reduction processing on said reference image and then performing the other of the expansion processing and the reduction processing on said processed reference image; and
d) a defect candidate excluding step of excluding a region of said defect candidate region that overlaps with said mask region from a defect candidate and then acquiring presence of a defect in said captured image on the basis of said defect candidate region.

5. A non-transitory computer-readable medium carrying a program for causing a computer to detect a defect in a target region of a surface of an object from a plurality of images of said target region, said computer executing said program to cause said computer to execute:

a) a step of preparing a captured image acquired by capturing an image of said target region, and a corresponding reference image;
b) a defect candidate region detection step of detecting a defect candidate region on the basis of at least one of a difference and a ratio between pixel values in said captured image and respective pixel values in a first image, wherein the first image is obtained by performing one of expansion processing and reduction processing on said captured image and then performing the other of the expansion processing and the reduction processing on said processed captured image;
c) a mask region detection step of, after a reference image corresponding to said captured image is prepared, detecting a mask region on the basis of at least one of a difference and a ratio between pixel values in said reference image and respective pixel values in a second image, wherein the second image is obtained by performing the one of the expansion processing and the reduction processing on said reference image and then performing the other of the expansion processing and the reduction processing on said processed reference image; and
d) a defect candidate excluding step of excluding a region of said defect candidate region that overlaps with said mask region from a defect candidate and then acquiring presence of a defect in said captured image on the basis of said defect candidate region.

6. The defect detection device according to claim 1, wherein
said expansion processing includes applying a maximum value filter on an image, and
said reduction processing includes applying a minimum value filter on an image.

* * * * *